(12) United States Patent
Blander et al.

(10) Patent No.: US 10,588,964 B2
(45) Date of Patent: Mar. 17, 2020

(54) BACTERIAL RNAS AS VACCINE ADJUVANTS

(71) Applicant: ICAHN SCHOOL OF MEDICINE AT MOUNT SINAI, New York, NY (US)

(72) Inventors: Julie Magarian Blander, North Haven, CT (US); Leif Erik Sander, Berlin (DE)

(73) Assignee: Cornell University, Ithaca, NY (US)

( * ) Notice: Subject to any disclaimer, the term of this patent is extended or adjusted under 35 U.S.C. 154(b) by 0 days.

(21) Appl. No.: 15/809,130

(22) Filed: Nov. 10, 2017

(65) Prior Publication Data

US 2018/0326050 A1 Nov. 15, 2018

Related U.S. Application Data

(63) Continuation of application No. 14/233,631, filed as application No. PCT/US2012/047087 on Jul. 17, 2012, now Pat. No. 9,844,592.

(60) Provisional application No. 61/565,733, filed on Dec. 1, 2011, provisional application No. 61/509,028, filed on Jul. 18, 2011.

(51) Int. Cl.
*A61K 39/00* (2006.01)
*A61K 39/39* (2006.01)

(52) U.S. Cl.
CPC .......... *A61K 39/39* (2013.01); *A61K 39/0011* (2013.01); *A61K 2039/522* (2013.01); *A61K 2039/585* (2013.01); *Y02A 50/403* (2018.01); *Y02A 50/478* (2018.01)

(58) Field of Classification Search
CPC .................................................... A61K 39/39
See application file for complete search history.

(56) References Cited

U.S. PATENT DOCUMENTS

| | | | |
|---|---|---|---|
| 4,016,253 A | 4/1977 | Switzer | |
| 4,389,396 A | 6/1983 | Hinterland | |
| 7,579,009 B2 | 8/2009 | McIntyre | |
| 7,858,073 B2 | 12/2010 | Clancy | |
| 8,008,267 B2 | 8/2011 | Kandimalla | |
| 8,106,173 B2 | 1/2012 | Kandimalla | |
| 8,202,974 B2 | 6/2012 | Lan | |
| 9,226,959 B2 | 1/2016 | Kramps | |
| 9,297,008 B2 | 3/2016 | Li | |
| 2005/0123565 A1 | 6/2005 | Subramony | |
| 2005/0220883 A1 | 10/2005 | O'Hagan | |
| 2007/0104733 A1 | 5/2007 | Gunn | |
| 2007/0219149 A1 | 9/2007 | Hasegawa | |
| 2008/0025944 A1 | 1/2008 | Hoerr | |
| 2009/0093433 A1 | 4/2009 | Woolf | |
| 2010/0178272 A1 | 7/2010 | Hartmann | |
| 2011/0250225 A1 | 10/2011 | Fotin-Mleczek | |
| 2012/0213818 A1 | 8/2012 | Hoerr | |

FOREIGN PATENT DOCUMENTS

| | | |
|---|---|---|
| GB | 1109179 | 4/1968 |
| WO | WO-2008017473 | 2/2008 |
| WO | WO-2009022216 | 2/2009 |
| WO | WO-2003070909 | 8/2009 |
| WO | WO-2009095226 | 8/2009 |
| WO | WO-2010037408 | 4/2010 |
| WO | WO-2010037539 | 4/2010 |
| WO | WO-2010135170 | 11/2010 |

OTHER PUBLICATIONS

Belasco, "All things must pass: contrasts and commonalities in eukaryotic and bacterial mRNA decay," Nat Rev Mol Cell Biol, 11:467-478 (2010).
Blander et al., "Regulation of phagosome maturation by signals from toll-like receptors," Science 304:1014-1018 (2004).
Bolstad et al., "A comparison of normalization methods for high density oligonucleotide array data based on variance and bias," Bioinformatics, 19:185-193 (2003).
Brockstedt et al., "Killed but metabolically active microbes: a new vaccine paradigm for eliciting effector T-cell responses and protective immunity," Nat Med, 11:853-860 (2005).
Buchmeier et al., "Induction of *Salmonella* stress proteins upon infection of macrophages," Science 248:730-732 (1990).
Casavant et al., "The adjuvant activity of mycobacterial RNA preparations and synthetic polynucleotides for induction of delayed hypersensitivity to purified protein derivative in guinea pigs," Journal of Immunology, 114(3):1014-1022 (1975).
Causton et al., "mRNA degradation in *Escherichia coli*: a novel factor which impedes the exoribonucleolytic activity of PNPase at stem-loop structures," Mol Microbiol, 14:731-741 (1994).
Cheers et al., "How do macrophages distinguish the living from the dead?" Trends Microbiol, 4: 453-455 (1996).
Coll et al., "New insights into the regulation of signalling by toll-like receptors and nod-like receptors," J Innate Immun, 2:406-421 (2010).
Dai et al., "Evolving gene/transcript definitions significantly alter the interpretation of GeneChip data," Nucleic acids research, 33:e175 (2005).
Davis et al., "Technical advance: Caspase-1 activation and IL-1β release correlate with the degree of lysosome damage, as illustrated by a novel imaging method to quantify phagolysosome damage," J Leukoc Biol, 88:813-822 (2010).
Detmer et al., "Live bacterial vaccines—a review and identification of potential hazards," Microb Cell Fact, 5:23 (2006).
Gentleman et al., Bioconductor: open software development for computational biology and bioinformatics, Genome Biol, 5, R80 (2004).
Gripenland et al., "RNAs: regulators of bacterial virulence," Nat Rev Microbiol, 8:857-866 (2010).
Haraga et al., "Salmonellae interplay with host cells," Nat Rev Microbiol, 6:53-66 (2008).

(Continued)

*Primary Examiner* — Albert M Navarro
(74) *Attorney, Agent, or Firm* — Hodgson Russ LLP

(57) ABSTRACT

The invention features vaccine adjuvants comprising prokaryotic mRNA, and methods of vaccination using the adjuvants.

18 Claims, 45 Drawing Sheets
Specification includes a Sequence Listing.

(56) References Cited

OTHER PUBLICATIONS

Herskovits et al., "Bacterial ligands generated in a phagosome are targets of the cytosolic innate immune system," PLoS Pathog, 3:e51 (2007).
Hornung et al., "5'-Triphosphate RNA is the ligand for RIG-I," Science, 314:994-997 (2006).
Hornung et al., "Silica crystals and aluminum salts activate the NALP3 inflammasome through phagosomal destabilization," Nat Immunol, 9:847-856 (2008).
Irizarry et al., "Summaries of Affymetrix GeneChip probe level data," Nucleic acids research, 31:e15 (2003).
Kanneganti et al., "Bacterial RNA and small antiviral compounds activate caspase-1 through cryopyrin/Nalp3," Nature, 440:233-236 (2006).
Kariko et al., "Suppression of RNA recognition by Toll-like receptors: the impact of nucleoside modification and the evolutionary origin of RNA," Immunity, 23:165-175 (2005).
Kawamura, et al., Antigen provoking gamma interferon production in response to *Mycobacterium bovis* BCG and functional difference in T-cell responses to this antigen between viable and killed BCG-immunized mice Infect. Immun. 62: 4396-4403 (1994).
Kuida et al., "Altered cytokine export and apoptosis in mice deficient in interleukin-1 beta converting enzyme,"Science, 267:2000-2003 (1995).
Lauvau, et al., Priming of memory but not effector CD8 T cells by a killed bacterial vaccine Science 294: 1735-1739 (2001).
Li et al., "Adjuvant effects of plasmid-generated hairpin RNA molecules on DNA vaccination," Vaccine, 25(39-40):6992-7000 (2007).
Mariathasan et al., "Inflammasome adaptors and sensors: intracellular regulators of infection and inflammation," Nat Rev Immunol, 7: 31-40 (2007).
Maurell et al., "Cloning of plasmid DNA sequences involved in invasion of HeLa cells by Shigella flexneri," Infect Immun, 49:164-171 (1985).
Medzhitov, "Approaching the asymptote: 20 years later," Immunity, 30:766-775 (2009).
Monroe et al., "Identification of host cytosolic sensors and bacterial factors regulating the type I interferon response to *Legionella pneumophila*," PLoS Pathog, 5:e1000665 (2009).
Nallagatla et al., "A brilliant disguise for self RNA: 5'-end and internal modifications of primary transcripts suppress elements of innate immunity," RNA Biol, 5:140-144 (2008).
Lim et al Phytol-based novel adjuvants in vaccine formulation: 2, assessment of efficacy in the induction of protective immune responses to lethal bacterial infections in mice, Journal of Immune Based Therapies and Vaccines 4: 5 (2006).
Pahl, "Activators and target genes of Rel/NF-kappaB transcription factors," Oncogene, 18:6853-6866 (1999).
Pang et al., "Inflammasomes as mediators of immunity against influenza virus," Trends Immunol, 32:34-41 (2011).
Piekna-Przybylska et al., "The 3D rRNA modification maps database: with interactive tools for ribosome analysis," Nucleic Acids Res, 36:D178-183 (2008).

Raskin et al., "Bacterial genomics and pathogen evolution," Cell, 124:703-714 (2006).
Rehwinkel et al., "RIGorous detection: exposing virus through RNA sensing," Science, 327:284-286 (2010).
Riedl et al., "Priming Th1 immunity to viral core particles is facilitated by trace amounts of RNA bound to its arginine-rich domain," The Journal of Immunology, 168(10):4951-4959 (2002).
Saeed et al., "TM4 microarray software suite," Methods Enzymol, 411:134-193 (2006).
Saeed et al., "TM4: a free, open-source system for microarray data management and analysis," Biotechniques, 34:374-378 (2003).
Samarajiwa et al., "INTERFEROME: the database of interferon regulated genes," Nucleic Acids Research, 37:D852-857 (2009).
Sander et al., "Sensing prokaryotic mRNA signifies microbial viability and promotes immunity," Nature, 474:385-389 (2012).
Sartor et al., "Intensity-based hierarchical Bayes method improves testing for differentially expressed genes in microarray experiments," BMC Bioinformatics, 7:538 (2006).
Sato et al.," Distinct and essential roles of transcription factors IRF-3 and IRF-7 in response to viruses for IFN-alpha/beta gene induction," Immunity, 13:539-548 (2000).
Scheel et al., "Immunostimulating capacities of stabilized RNA molecules," European Journal of Immunology, 34(2):537-547 (2004).
Schnupf et al., "Listeriolysin O: a phagosome-specific lysin," Microbes Infect, 9:1176-1187 (2007).
Schroder et al., "The inflammasomes," Cell, 140:821-832 (2010).
Shimada et al., "*Staphylococcus aureus* evades lysozyme-based peptidoglycan digestion that links phagocytosis, inflammasome activation, and IL-1beta secretion," Cell Host Microbe, 7:38-49 (2010).
Song et al., "TLR4-mediated expulsion of bacteria from infected bladder epithelial cells," Pro Natl Aced Sci USA, 106:14966-71 (2009).
Storey et al., "Statistical significance for genomewide studies," Proc Natl Acad Sci USA, 100:9440-9445 (2003).
Sutterwala et al., "Critical role for NALP3/CIAS1/Cryopyrin in innate and adaptive immunity through its regulation of caspase-1," Immunity, 24:317-327 (2006).
Sutterwala et al., "The inflammasome in pathogen recognition and inflammation," J. Leukocyte Biol, 82:259-264 (2007) (Print n Scan).
Takeuchi et al., "Pattern recognition receptors and inflammation," Cell, 140:805-820 (2010).
Thulin et al., "Viable group A streptococci in macrophages during acute soft tissue infection," PLoS Med 3:e53 (2006).
Vance et al., Patterns of pathogenesis: discrimination of pathogenic and nonpathogenic microbes by the innate immune system Cell Host Microbe 6: 10-21 (2009).
Von Koenig et al., "Failure of killed Listeria monocytogenes vaccine to produce protective immunity," Nature, 297:233-234 (1982).
Wing et al., "Regulation of IcsP, the outer membrane protease of the Shigella actin tail assembly protein IcsA, by virulence plasmid regulators VirF and VirB," J Bacteriol, 186:699-705 (2004).
Woodward et al., "c-di-AMP secreted by intracellular Listeria monocytogenes activates a host type I interferon response," Science ,328:1703-1705 (2010).
Zhou et al., "A role for mitochondria in NLRP3 inflammasome activation," Nature, 469:221-225 (2011).

US 10,588,964 B2

BACTERIAL RNAS AS VACCINE ADJUVANTS

CROSS REFERENCES TO OTHER APPLICATIONS

This application is a continuation of U.S. patent application Ser. No. 14/233,631, filed Jan. 17, 2014, (allowed), which is a national stage application under 35 U.S.C. § 371 of International Application No. PCT/US2012/047087 (expired), filed Jul. 17, 2012, which claims priority from U.S. Provisional Application 61/509,028, filed Jul. 18, 2011, and U.S. Provisional Application 61/565,733, filed Dec. 1, 2011. The disclosures of those applications are incorporated by reference herein in their entirety.

A Sequence Listing associated with this application is being submitted electronically via EFS-Web in text format, and is hereby incorporated by reference in its entirety into the specification. The name of the text file containing the Sequence Listing is 002257-0012-302-SL.txt. The text file, created on Nov. 10, 2017, is 5,117 bytes in size.

GOVERNMENT INTEREST

This invention was made with government support under Grant Number AI080959 awarded by from the National Institutes of Health. The government has certain rights in the invention.

BACKGROUND OF THE INVENTION

A vaccine is a biological preparation that improves immunity to a particular disease. A vaccine typically contains an agent that resembles a disease-causing pathogen, such as a microorganism in weakened or killed forms or an antigen derived from the microorganism. The agent stimulates the body's immune system to recognize the agent as foreign, destroy it, and "remember" it, so that the immune system can more easily recognize and destroy the pathogen that it later encounters. A successful immune response is characterized by, e.g., eradication of pathogens, tissue repair, and short and long term immune memory. Vaccines can be prophylactic (e.g., to prevent or ameliorate the effects of a future infection by a pathogen), or therapeutic (e.g., vaccines against cancer or passive immunization against established infections, e.g., rabies). A vaccine often contains, or is administered with, an adjuvant. A vaccine adjuvant is an agent that stimulates the immune system and increases the immune system's response to a vaccine. The adjuvant itself typically does not have any specific antigenicity.

Vaccination is the most effective public health measure to prevent infectious disease associated morbidity and mortality. Improving vaccines against bacterial pathogens like Mycobacterium tuberculosis or enteropathogenic bacteria like Shigella flexneri would significantly lower public health costs that result from treating these infections. Generally, there are two types of microbe-based vaccine—live vaccines, which contain live pathogens, and dead vaccines, which contain killed pathogens.

Live vaccines have long been known to trigger far more vigorous immune responses than their killed counterparts (Brockstedt et al., Nat Med 11: 853-860 (2005); Cheers et al., Trends Microbiol 4: 453-455 (1996); Detmer et al., Microb Cell Fact 5: 23 (2006); Kawamura, et al., Infect. Immun. 62: 4396-4403 (1994); Lauvau, et al., Science 294: 1735-1739 (2001); von Koenig et al., Nature 297: 233-234 (1982)). This has been attributed to the ability of live microorganisms to replicate and express specialized virulence factors that facilitate invasion and infection of their hosts (Vance et al., Cell Host Microbe 6: 10-21 (2009)). However, protective immunization can often be achieved with a single injection of live, but not dead, attenuated microorganisms stripped of their virulence factors. Pathogen associated molecular patterns (PAMPs), which serve to alert the immune system (Medzhitov, Immunity 30: 766-775 (2009); Takeuchi et al., Cell 140: 805-820 (2010)) are present in both live and killed vaccines, suggesting that certain poorly characterized aspects of live microorganisms, not incorporated in dead vaccines, are particularly effective at inducing protective immunity.

Attenuated live vaccines are often superior to dead vaccine preparations, but they still have the risk of causing a severe infection, especially in immunocompromised individuals. Attenuated vaccine strains are usually genetically engineered pathogens. There is a significant public concern about the release of such strains. In addition, there is a risk of spontaneous reversion to virulence in attenuated organisms. These risks not only limit the use of attenuated live vaccines, but also cause concern and impede compliance. Further, live vaccines are labile, requiring complicated measures for storing and shipping, and are more costly to handle than dead vaccines. Therefore, it would be advantageous to improve the efficacy of dead vaccines, to minimize the risks associated with immunization with live vaccines, as well as the costs of vaccine storage and handling. Such improvement would promote public health and lower health care costs.

SUMMARY OF THE INVENTION

The present invention is based on our discovery that bacterial mRNA enhanced efficiency of dead vaccine preparations due to its newly discovered capacity to induce immune responses similar to those evoked by viable bacteria. Accordingly, an aspect of this invention is a vaccine composition comprising a nonviable immunogen (e.g., heat-killed bacterium) and an adjuvant, wherein said adjuvant comprises prokaryotic mRNA (e.g., bacterial mRNA). In some embodiments, the prokaryotic mRNA may be delivered to the subject by using the immunogen as a cargo, i.e., the mRNA is contained within, or co-delivered with, the immunogen.

In some embodiments, the immunogen is an extracellular pathogen, or an intracellular pathogen. The immunogen can be a bacterium, and may be of a genus selected from a group consisting of Escherichia, Streptococcus, Staphylococcus, Clostridium, Campylobacter, Enterococcus, Helicobacter, Moraxella, Acinetohacter, Shigella, Salmonella, Listeria, Legionella, Klebsiella, Pseudomonas, Brucella, Haemophilus, Bordetella, Borrelia, Bacteroides, Bacillus, Chlamydia, Neisseria, Francisella, Yersinia, Vibrio, Mycobacterium, Mycoplasma, Corynebacterium, and Rickettsia.

In some embodiments, the invention features a tumor vaccine comprising a tumor antigen and an adjuvant, wherein said adjuvant comprises prokaryotic mRNA. In some embodiments, the tumor antigen is carried by a cell. In some embodiments, the invention features a tumor vaccine comprising an immunogenic peptide of microbial or mammalian origin and an adjuvant, wherein said adjuvant comprises prokaryotic mRNA. In some embodiments, a prokaryotic mRNA is delivered to a subject by optionally using the cell as a cargo.

In some embodiments, the prokaryotic mRNA used in the adjuvants of this invention has a 3' stem-loop structure, has no 5' tri-phosphate group, has no 3' poly(A) tail, intramolecular base-pairing, and/or nucleotide modifications.

In some embodiments, the vaccine compositions of this invention further include a second adjuvant component, such as mineral oil in water emulsions (e.g., MF59, AS3, montanide), aluminium salts, CpG, monophosphory lipid A (a detoxified derivative of endotoxin from, e.g., the *Salmonella minnesota* Re595 strain; "MPLA"), QS21 (a saponin purified from *Quillaja saponaria* tree bark; its oil-in-water emulsion suspension is also known as AS02), lipopolysaccharides ("LPS"), peptidoglycans, and bacterial lipopeptides characterized by their ability to trigger Toll-like receptors residing on the plasma membrane or recycle through early endocytic compartments.

The invention further features an immunization kit comprising a vaccine composition comprising a nonviable immunogen and an adjuvant composition comprising prokaryotic mRNA. The invention also features an immunization kit comprising a vaccine composition comprising a tumor antigen and an adjuvant composition comprising prokaryotic mRNA. Various embodiments of the immunogen, tumor antigen, and prokaryotic mRNA are, for example, as those described above and further below.

The invention also features a method of eliciting an immune response in a subject, comprising administering to the subject the present composition, as well as a method of increasing the immune response to a killed vaccine in a subject, comprising administering the killed vaccine to the subject with an adjuvant comprising prokaryotic mRNA. The subject may be a human, a house pet, or a farm animal. The vaccination methods of this invention may protect the subject from developing an infectious disease; or protect the subject from developing a cancer, or treat a subject in need of cancer immunotherapy. The vaccination methods of this invention may boost the immune response in a subject by increasing IL-1β production, IFN-β production, increased IgG isotype levels, increased primary and secondary (recall or memory) T cell responses, and death of infected cells. Also included in this invention are methods of inducing IFN-β or IL-1β production in immune cells comprising contacting the cells with the present composition, and methods of preparing a vaccine composition comprising mixing a target immunogen with prokaryotic mRNA.

BRIEF DESCRIPTION OF THE DRAWINGS

FIG. 22. Bacterial RNA alone or in combination with LPS is insufficient to induce inflammasome activation unless delivered directly into the cytosol. BMM were stimulated with total RNA isolated from ThyA$^-$ E. coli for 24 hours at the indicated concentrations in the presence or absence of LPS and/or Lipofectamine (LF) transfection reagent (Invitrogen). Lipofectamine treatment encapsulates nucleic acids allowing them to cross the plasma membrane and to be released into the cytosol. A combination of LPS and RNA was used to mimic an E. coli derived PAMP and RNA. LDH (top) and IL-1β release (bottom) were measured in the supernatants. Note that the LDH and IL-1β levels detected after LF+LPS+RNA treatment are lower than after HK E. coli+RNA treatment (FIG. 3c). LPS alone had no effect (data not shown). #; 'not detected'.

DETAILED DESCRIPTION OF THE INVENTION

Figure 1:
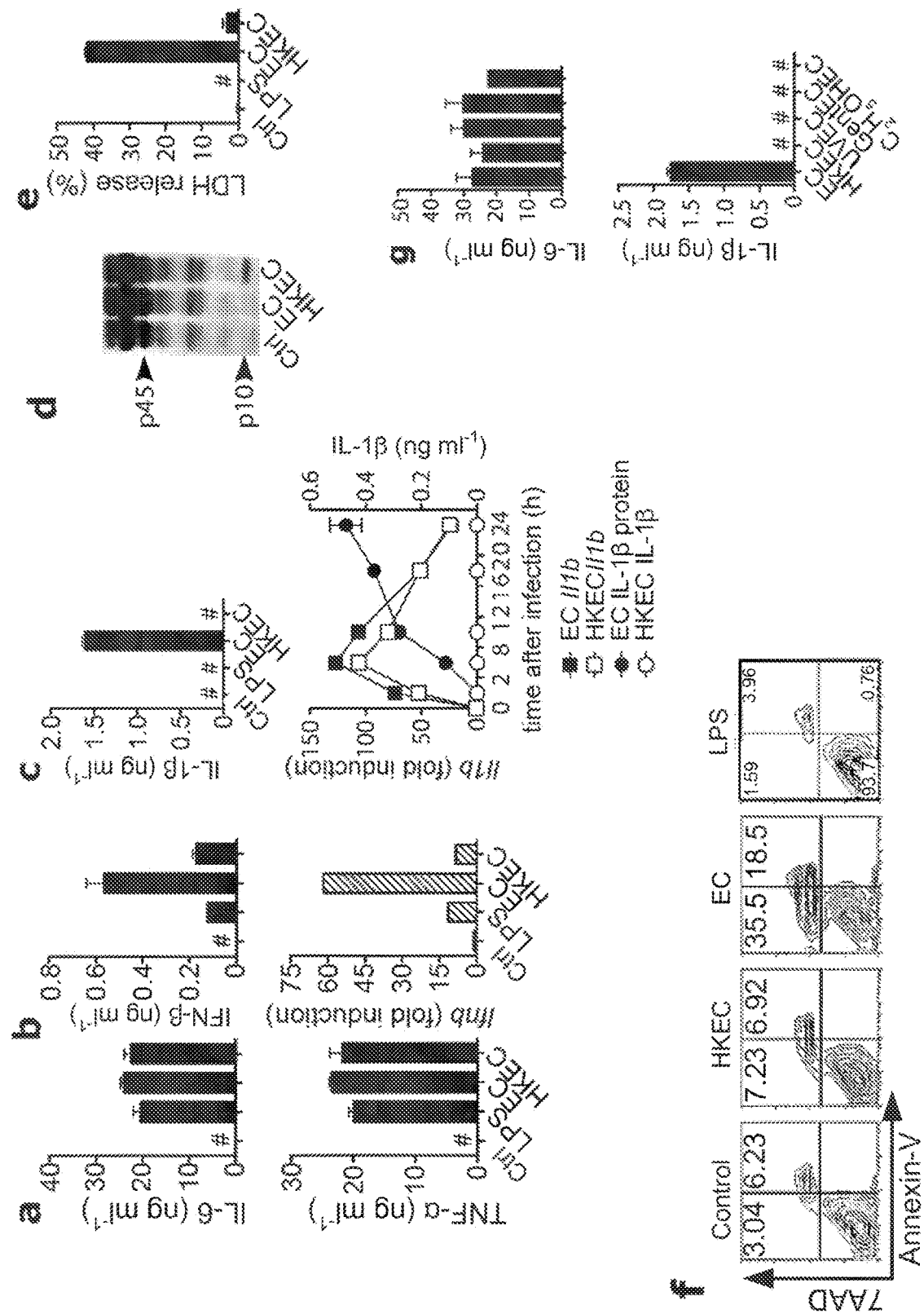
FIG. 1. Sensing bacterial viability induces IFN-β and activates the NLRP3 inflammasome in the absence of virulence factors. (a) IL-6, TNF-α, (b) IFN-β protein, mRNA (at 2 h) in bone marrow derived macrophages (BMM) stimulated with medium (contr), 100 ng/ml Lipopolysaccharide (LPS), ThyA$^-$ *E. coli* (EC), and heat-killed EC (HKEC), MOI=20. (c) IL-1β (top), and Il1b mRNA (left y-axis), secreted IL-1β (right y-axis) at indicated times (bottom). (d), (i) Caspase-1 immunoblots at 18 h. Pyroptosis by lactate dehydrogenase (LDH) release (e), and Fluorescence-Activated Cell Sorter (FACS) analysis through detection of Annexin-V and 7-AAD staining (f) at 18 h. IL-6 and IL-1β in response to EC, viable or killed by different means (g, bone marrow derived DC (BMDC)), or viable or HK: EC, attenuated *Shigella* (BS103), *Salmonella* (ΔSpi1/2), and *Listeria* (ΔHlyΔFliC), or virulent *Salmonella* (SL1344) (h). (j) LDH, IL-1β, and IL-6. All responses by BMM and measured at 24 h unless indicated otherwise. #, 'Not detected'. Data represent ≥5 experiments. All bars represent mean±s.e.m.
Figure 1:
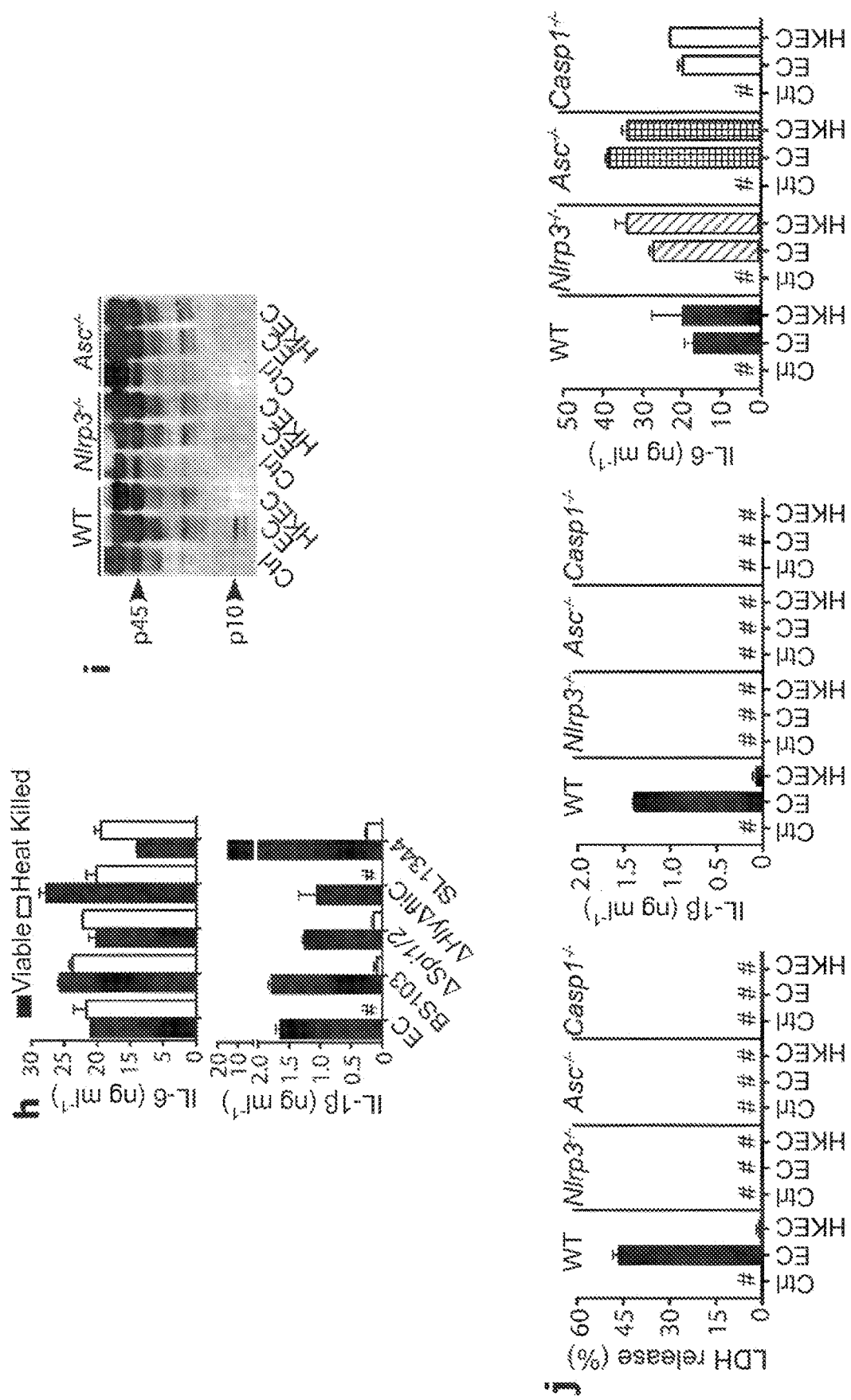

The present invention is based on our discovery of the molecular mechanisms underlying the different efficacies of live and dead vaccines. Our studies described below show for the first time that antigen-presenting cells can sense microbial viability through recognition of prokaryotic mRNA. Optimal activation of antigen-presenting cells is a basic prerequisite for the generation of protective adaptive immunity, which is the ultimate goal of vaccination. We have discovered that addition of purified bacterial mRNA to heat inactivated bacteria elicited the same immune response in antigen-presenting cells as did viable bacteria. By prokaryotic RNA (e.g., bacterial mRNA) as vaccine adjuvants, we have developed improved dead vaccines that combine their higher safety profile with the efficacies of live vaccines.

Most adjuvants in existing vaccination technologies are unspecific and trigger a broad range of immune responses. It is not entirely clear which responses are actually required to generate robust immunity, and which responses may even inhibit the generation of immunological memory. So far, mostly empiric data serve as the basis for adjuvant use. Due to their unspecific nature, many vaccine adjuvants are known to cause significant local and systemic side effects.

We have discovered that prokaryotic RNA, e.g., bacterial mRNA, significantly enhances the desired immune response and thus can be used as an adjuvant in a vaccine composition. The enhanced immune response is specific to the target immunogen in the vaccine composition, rather than nonspecific as often seen with conventional adjuvants. In other words, prokaryotic RNA can be used as an adjuvant to augment the effects of a vaccine with fewer side effects. Specifically, the invention features the use of purified prokaryotic RNA (e.g., bacterial mRNA or similar synthetic RNA) as vaccine adjuvant to mimic infection with live microbes and thereby improve dead vaccine efficiency and adjuvant specificity. The improved dead vaccines of this invention avoid the risks associated with handling and administration of live vaccines, especially in infants, elderly and immunocompromised patients.

Prokaryotic RNA Adjuvants

The adjuvant of the present invention comprises an effective amount of prokaryotic RNA, i.e., an amount of prokaryotic RNA sufficient to stimulate the anti-target immune response to a desired level, such that protective immunity is generated in a recipient. As used herein, "prokaryotic RNA" refers to RNA isolated from prokaryotic microorganisms such as archaca and bacteria, and to RNA having structural features characteristics of RNA obtained from prokaryotic microorganisms. In the latter case, the RNA may or may not have significant sequence homology to naturally occurring prokaryotic RNA, despite having the same structural features. The immune-enhancing property of the prokaryotic RNA is not sequence-specific. That is, a prokaryotic RNA would have immune-enhancing effects, regardless of its particular nucleotide composition, as long as the requisite structural features are present.

In some preferred embodiments, the prokaryotic RNA in the adjuvant comprises bacterial messenger RNA (mRNA) and/or RNA having structural features of bacterial mRNA. Such structural features include, for example, absence of 3' polyadenylation (poly(A) tail), presence of a double-stranded secondary structure such as a 3' stem-loop structure, lack of eukaryotic modifications (e.g., certain nucleoside modifications), lack of 7 m$^7$G capping at the 5' end, and special nucleoside modifications that exist in bacterial mRNA but not in other bacterial RNAs or in eukaryotic RNAs. These structural features can be introduced to the RNA molecule during synthesis. Further structure features may also be introduced to enhance the RNA molecules' adjuvant and immunostimulatory activities. For example, unique conformations may be important in imparting immunogenicity on an RNA molecule, and thus, modifications can be made in the synthetic RNA molecule such that the RNA molecule assumes a linear noncircular conformation of bacterial mRNA.

In some embodiments, the prokaryotic RNA has a length ranging, for example, from about 50 nucleotides to about 2000 nucleotides, e.g., from about 800 nucleotides to about 2000 nucleotides. In some embodiments, the RNA has a length ranging from about 2000 nucleotides to more than 8000 nucleotides; for example, the mRNA encoding the *Clostridium difficile* toxin A subunit is 8130 nucleotides long. In some embodiments, the prokaryotic RNA does not have any 5' triphosphate group.

In some embodiments, the prokaryotic RNA is modified to increase stability. Exemplary stabilized RNA molecules include, inter alia, RNA molecules having a CpG, C*pG, C*pG*, or CpG* sequence where C* may be 2'-deoxythymidine, 1-(2'-deoxy-.beta.-D-ribofuranosyl)-2-oxo-7-deaza-8-methyl-purine, 2'-dideoxy-5-halocytosine, 2'-didcoxy-5-nitrocytosine, arabinocytidine, 2'-deoxy-2'-substituted arabinocytidine, 2'-O-substituted arabinocytidine, 2'-deoxy-5-hydroxycytidine, 2'-deoxy-N4-alkyl-cytidine, 2'-deoxy-4-thiouridine, or other non-natural pyrimidine nucleosides, G* is 2'deoxy-7-deazaguanosine, 2'-deoxy-6-thioguanosine, arabinoguanosine, 2'-deoxy-2' substituted-arabinoguanosine, 2'-O-substituted-arabinoguanosine, 2'-deoxyinosine, or another non-natural purine nucleoside, and p may be an internucleoside linkage such as phosphodiester, and phosphorothioate (see, e.g., U.S. Pat. No. 8,008,267 to Kandimalla et al.); and RNA molecules having protected 3' and/or 5' ends (see, e.g., U.S. Patent Application Publication No. 2008/0171712 by Kandimalla et al.).

The prokaryotic RNA useful in this invention can be isolated from, e.g., bacterial cells by well known methods. For example, bacteria cells are homogenized or disrupted using a combination of denaturants and RNase inhibitors, including, e.g., TRIzol® (Life Technologies). This step is followed by the addition of chloroform to the lysate, and the mixture is separated into three phases by centrifugation. The RNA is then precipitated from the aqueous phase with isopropanol. Alternatively, whole RNA can be extracted using silica-gel column based approaches. Messenger RNA can be purified by negative selection, for example, by removal of rRNA using immobilized rRNA-specific probes (e.g., immobilized on magnetic bead), followed by chromatography to exclude non-rRNA species of smaller size (e.g., tRNA). RNA can be stabilized by various commercially available stabilizers, e.g., RNAlater® (Life Technologies), an aqueous storage reagent that stabilizes and protects RNA, and various widely available RNase inhibitors.

Cellular sources for the prokaryotic RNA can be, for example, *E. coli, Salmonella, Shigella, Pseudomonas, Acinetobacter*, or other gram-negative bacteria. In some embodiments, the prokaryotic RNA in the adjuvant is total RNA extracted from one or more prokaryotic sources (e.g., more than one type of bacteria). In some embodiments, the prokaryotic RNA in the adjuvant is mRNA isolated from its prokaryotic source(s). In other embodiments, the prokaryotic RNA in the adjuvant is transcribed or synthesized in vitro. RNA used in the adjuvant can be a mix of multiple RNA species, each with a different nucleotide sequence, or contains a single species of RNA molecules, each having or originating from the same nucleotide sequence.

The RNA in the adjuvant may be presented in a format that facilitates delivery into a cell by, e.g., phagocytosis or receptor-mediated endocytosis. For example, the RNA may be encapsulated in liposomes, polylactide microspheres, or poly(lactic-co-glycolic acid) microspheres, or linked or conjugated to the surface of a cargo (such as beads, and micro- or nano-particles). The RNA may also be co-administered with, or coupled to a molecule, such as an antibody or a specific ligand, that targets an endocytic receptor on the surface of antigen-presenting cells, such as Fc-receptors or C-type-lectins (DC-SIGN, DEC-205), or to a protective antigen component of, e.g., anthrax toxin. The RNA may also be tagged (e.g., by incorporation of biotin molecules such as biotinylated nucleotides, or through Click-chemistry), and linked directly to an antigen-complex, a dead microbe, or a vaccine vector. The RNA in the adjuvant may also be complexed with other delivery agents, including, without limitation, polyethylenimine, collagen derivatives, virosomes, SNALPs (stable nucleic acid lipid particles), ISCOMATRIX®, and polyethylene glycol (PEG). The RNA may also be delivered with other PAMPs such as CpG, lipopolysaccharide (LPS), flagellin, or MPLA.

In addition to prokaryotic RNA, the adjuvant of this invention can also include a pharmaceutically acceptable excipient, and optionally other adjuvant ingredients. For example, the adjuvant of this invention may contain mineral oil, certain bacterial toxins, aluminium salts such as aluminium hydroxide and aluminium phosphate, squalene, virosomes, mineral oil in water emulsions (e.g., MF59, AS3, and montanide), CpG, LPS, MPLA, QS21 or AS02, flagellin, peptidoglycans, and/or whole killed or otherwise inactivated bacterial pathogens. The adjuvant may also contain agents that help stabilize the immunogen and/or the RNA component, e.g., RNAse inhibitors.

The present prokaryotic RNA adjuvants are different from existing adjuvants in that the former use a specific pathogen-associated molecular pattern (PAMP) that is strictly associated with microbial viability. In contrast, currently available adjuvants contain PAMPs found in both live and dead microbes (such as peptidoglycans, CpG, flagellin, LPS, MPLA, AS04 (a mixture of MPL and aluminium salt), or virion particles), or even synthetic or chemical compounds not associated with infectious disease at all (such as alum, imiquimod, MF59, montanide, AS02 and QS21.

The vaccine compositions of this invention will provoke an immune response that closely mimics a productive infection tailored to clear infection and establish protective immunity. Thus, the prokaryotic RNA adjuvant of this invention is particularly useful when used in conjunction with a killed vaccine, because it can greatly enhance the immune response to the killed vaccine in a recipient, rendering the killed vaccine as effective as, if not more than, a live vaccine. The prokaryotic RNA adjuvant of this invention can also reduce the amount of immunogen, killed or live, required for vaccination, thereby increasing the safety and comfort of vaccination. Furthermore, prokaryotic RNA is safe to be used in vertebrate subjects because it is inert in vertebrates and does not cause any disease or undesirable conditions: once endocytosed, RNA is easily degradable by the host, and there is no hazard of genotoxicity because the prokaryotic origin and characteristics of the RNA prevent its integration or translation by host enzymes.

Vaccine Compositions

A vaccine composition of the present invention contains a target immunogen, the RNA adjuvant of this invention, and a pharmaceutically acceptable carrier such as saline. The target immunogen and the RNA adjuvant can be packaged separately and administered simultaneously, or they can be pre-mixed during manufacture of the vaccine composition. The vaccine composition may additionally contain other adjuvants such as mineral oil, certain bacterial toxins, aluminium salts, squalene, virosomes, mineral oil in water emulsions (e.g., MF59, MF50, AS3, and montanide), LPS, CpG, R848, MPLA, flagellin, peptidoglycans, saponin-based adjuvants (e.g., QS21), combination adjuvants (e.g., AS02 and AS04), and/or whole killed or otherwise inactivated bacterial pathogens and virion particles. An exemplary adjuvant combination is prokaryotic mRNA and MPL. The vaccine composition may additionally contain RNA stabilizers, other preservatives, mineral oils for prolonged half life and release, carrier molecules like antibodies, biodegradable particles, and encapsulating agents such as liposomes. Subjects that can be vaccinated by the vaccine compositions of this invention include, without limitations, humans, pets (e.g., dogs and cats), and livestock (e.g., cattle, horses, sheep, goats, swine, and chickens).

The present invention provides vaccine compositions for infectious diseases such as those caused by bacteria and viruses. In some embodiments, the vaccine compositions comprise nonviable immunogens, e.g., pathogens that have been inactivated (e.g., killed by heat or other means) such that they cannot grow, spread, and cause disease in the vaccinated subject. The immunogens can be microbes such as bacteria that cause the particular disease for which the vaccine is intended. The immunogens may be viruses, parasites and fungi. The immunogens can be inactivated by, inter alia, heat, UV (e.g., long wavelength UV), beta- or gamma-radiation, ethanol, fixation (e.g., by the fixative paraformaldehyde), and/or psoralen.

The immunogens can be, for example, exogenous pathogens such as those from the genera *Escherichia, Streptococcus, Staphylococcus, Clostridium, Campylobacter, Enterococcus, Helicobacter, Moraxella, Acinetobacter* or obligate or facultative intracellular pathogens such as those from the genera *Acinetobacter, Shigella, Salmonella, Listeria, Legionella, Klebsiella, Pseudomonas, Brucella, Haemophilus, Bordetella, Borrelia, Bacteroides, Bacillus, Chlamydia, Neisseria, Francisella, Yersinia, Vibrio, Mycobacterium, Mycoplasma, Corynebacterium*, and *Rickettsia*.

In some embodiments, the vaccine compositions comprise a tumor antigen and an adjuvant comprising prokaryotic mRNA. In some embodiments, the vaccine compositions comprise an immunogenic peptide of microbial or mammalian origin and an adjuvant comprising prokaryotic mRNA. An immunogenic peptide is a peptide that produces an immunogenic response. Immunogenic peptides of microbial origin can be peptides that are isolated from a microbe, e.g., a bacterium, virus, fungus, protist, or protozoan. In some embodiments, the microbe can be a pathogen, such as an exogenous pathogen. Exemplary exogenous pathogens are described above. Immunogenic peptides of mammalian origin can be peptides that are isolated from a mammal or a mammalian cell. In some embodiments, a peptide of mammalian origin can be a recombinant protein that naturally occurs in mammals. For example, the mammal can be a human, primate, mouse, rat, dog, cat, pig, cow, or horse.

The vaccine compositions of this invention will help combat various infectious diseases that have caused significant health problems worldwide. For example, Legionellosis (Legionnaire's disease, caused by *Legionella*), tuberculosis (caused by *Mycobacteria*), shigellosis (caused by *Shigella*), and *Clostridium difficile*-associated colitis represent some of the most dangerous infectious diseases worldwide, with high morbidity and mortality rates, and rising prevalence. They cause huge costs to the public health system. Yet no efficient vaccines are available to date for these diseases. Vaccine compositions comprising dead microbes and the RNA adjuvants of the invention will be effective in treating such diseases. Likewise, nosocomial infections with multidrug resistant strains of *Pseudomonas aeruginosa, Klebsiella pneumoniae, Acinetobacter baumannii, Moraxella,* or *Escherichia coli* represent a growing problem in hospitals worldwide. Prophylactic vaccination of risk patients (immunocompromised and elderly patients) using the vaccines of this invention can significantly lower complications and mortality, as well as reducing the need for expensive reserve antibiotics.

This invention also provides vaccine compositions for preventing or treating conditions other than infectious diseases, e.g., cancers, and immune disorders such as allergies and autoimmune diseases. In some embodiments, the immunogens are tumor cells that are inactivated so that they are not viable in the recipient. In other embodiments, the immunogens are autologous or allogeneic cells engineered ex vivo to express a tumor antigen; in this case, the immunogens need not be rendered nonviable. The prokaryotic RNA adjuvant can potentiate the immune response to these immunogens. Such vaccine compositions can be used to prevent cancer in a subject that is at risk of developing cancer (e.g., due to genetic predisposition or exposure to carcinogens) or to treat cancer in a subject. The cancer can be, e.g., cancer of the blood or cancer of solid tissues, such as leukemia, lymphoma, thymoma, skin cancer (e.g., melanoma), throat or neck cancer, thyroid cancer, gastrointestinal cancers (e.g., esophageal, gastric, intestinal, colonic, rectal, and anal cancers), liver cancer (hepatocellular carcinoma or cholangio-carcinoma), pancreatic cancer, renal cancer, adrenocortical carcinoma, urinary tract cancer (e.g., bladder cancer), prostate cancer, testicular cancer, breast cancer, lung cancer (e.g., non-small cell lung cancer), mesothelioma, ovarian cancer, cervical cancer, vaginal cancer, brain cancer, retinoblastoma, sarcomas (e.g., Ewing's sarcomas), glioma, etc. In some embodiments, the prokaryotic RNA can be introduced into the tumor immunogen cells (e.g., by transfection, electroporation, and nucleofection) for delivery.

Unless otherwise defined, all technical and scientific terms used herein have the same meaning as commonly understood by one of ordinary skill in the art to which this invention belongs. Exemplary methods and materials are described below, although methods and materials similar or equivalent to those described herein can also be used in the practice or testing of the present invention. All publications and other references mentioned herein are incorporated by reference in their entirety. In case of conflict, the present specification, including definitions, will control. Although a number of documents are cited herein, this citation does not constitute an admission that any of these documents forms part of the common general knowledge in the art. Throughout this specification and claims, the word "comprise," or variations such as "comprises" or "comprising" will be understood to imply the inclusion of a stated integer or group of integers but not the exclusion of any other integer or group of integers. The materials, methods, and examples are illustrative only and not intended to be limiting.

EXAMPLES

The following examples describe our studies that show that the mammalian innate immune system can directly sense microbial viability through detection of a special class of viability-associated PAMPs (vita-PAMPs). These examples are meant to illustrate the methods and materials of the present invention. Suitable modifications and adaptations of the described conditions and parameters normally encountered in the art that are obvious to those skilled in the art are within the spirit and scope of the present invention.

In the following examples, we identified prokaryotic messenger RNA (mRNA) as a vita-PAMP present only in viable bacteria. Recognition of vita-PAMPs elicits a unique innate response and a robust adaptive antibody response. Notably, the innate response evoked by viability and prokaryotic mRNA had previously been considered to be reserved for pathogenic bacteria (Sutterwala et al., *J. Leukocyte Biol.* 82: 259-264 (2007), but we show that even non-pathogenic bacteria in sterile tissues can trigger similar responses, provided that they are alive. Thus, the immune system actively gauges the infectious risk by scouring PAMPs for signatures of microbial life and thus infectivity. Detection of vita-PAMPs triggers an alert mode not warranted for dead bacteria. Vaccine formulations that incorporate vita-PAMPs can thus combine the superior protection of live vaccines with the safety of dead vaccines.

Methods Summary

Cells were infected with *E. coli* DH5α ThyA$^-$ at MOI of 20 for 24 h unless stated otherwise. Supernatants were assayed for cytokines by ELISA. Genome wide transcriptional analysis of murine bone-marrow-derived macrophages (BMM) at 0, 1, 3 and 6 h post infection was carried out on Affymetrix GeneChip Mouse Gene 1.1 ST 24-array plates. Phagosomal leakage in BMMs was detected by measuring Fdx release using a modified method previously described (Davis et al., *J Leukoc Biol* 88: 813-822 (2010)). In brief, BMMs were treated with ThyA⁻ *E. coli* in the presence of 0.167 mg/ml Fdx and imaged with excitation at 440 nm (pH insensitive) and 485 nm (pH sensitive). Fluorescence intensity ratios at 485 nm/440 nm were converted into pH maps and % Fdx release calculated (total intensity of pixels containing released Fdx/total Fdx intensity). Bacterial RNA was extracted from *E. coli* using the e.z.n.a RNA kit (Omega) and in vitro transcription of bacterial genes carried out using the MEGAscript kit (Ambion) followed by DNase digestion and RNA purification using MEGAclear kit (Ambion). RNA polyadenylation was performed with the poly(A)-tailing kit (Ambion). Vaccinations were performed as a prime-boost regimen (see full Methods). C57BL/6J and P2rx7$^{-/-}$ mice were purchased from the Jackson Laboratory. MyD88$^{-/-}$ and Trif$^{-/-}$ mice were provided by S. Akira, Myd88$^{-/-}$×Trif$^{-/-}$ by R. Medzhitov, Nlrp3$^{-/-}$, Asc$^{-/-}$ and Nlrc4$^{-/-}$ by Millenium, and Caspase-1$^{-/-}$ by R. Flavell. Animal care and experimentation were performed in accordance with approved MSSM Institutional Animal Care and Use Committee protocols.

Cells

Bone marrow (BM)-derived dendritic cell (DC) cultures were grown as previously described (Torchinsky et al., *Nature* 458: 78-82 (2009)) in RPMI 1640 supplemented with GM-CSF and 5% fetal bovine serum (FBS), plus 100 µg/ml penicillin, 100 µg/ml streptomycin, 2 mM L-glutamine, 10 mM HEPES, 1 nM sodium pyruvate, 1% MEM non-essential amino acids, and 2.5 µM β-mercaptoethanol (all SIGMA). Semi-adherent cells were harvested on ice on day 5 and re-plated immediately in fresh RPMI 1640 medium containing 10% FBS at 1×10⁶ cells/well in 24-well tissue culture-treated plates. Stimuli were added immediately after re-plating in the same medium and the cells were centrifuged for 2' at 2000 rpm. Murine macrophages were derived from the BM (BMM) of either C57BL/6J, Myd88$^{-/-}$, Trif$^{-/-}$, Trif$^{-/-}$×Myd88$^{-/-}$, Nlrp3$^{-/-}$, Asc$^{-/-}$ or Casp1$^{-/-}$ mice, as described previously (Blander et al., *Science* 304: 1014-1018 (2004)), in RPMI 1640 supplemented with M-CSF and 10% FBS, plus 100 µg/ml penicillin, 100 µg/ml streptomycin, 10 mM HEPES and 1 nM sodium pyruvate (all SIGMA). For some experiments macrophages were derived from BM of Irf3$^{-/-}$ or P2rx7$^{-/-}$ mice. Peritoneal macrophages were harvested 72 h after intra-peritoneal injection of 1 ml thioglycollate (BD Bioscience), grown overnight in RPMI 1640 medium supplemented with 10% FBS and 100 µg/ml penicillin and 100 µg/ml streptomycin, hereafter referred to as "complete medium." Mouse embryonic fibroblasts (MEFs) deficient for RIG-I (RIG-I$^{-/-}$) were kindly provided by A. Ting with permission from S. Akira, and grown in DMEM medium containing 10% FBS and 100 µg/ml penicillin, 100 µg/ml streptomycin.

Mice

C57BL/6J and P2rx7$^{-/-}$ mice were purchased from Jackson Laboratories. Myd88$^{-/-}$ and Trif$^{-/-}$ mice were originally provided by S. Akira, Myd88-1 and Trif$^{-/-}$ mice were interbred to homozygosity to generate TrifxMyd88$^{-/-}$ mice, and were provided by R. Medzhitov.

Nlrp3$^{-/-}$, Asc$^{-/-}$ or Casp1$^{-/-}$ bone marrow was provided by B. Ryffel and mice for in vivo studies were acquired from R. Flavell (through Millenium) and have been described previously (Sutterwala et al., *Immunity* 24: 317-327 (2006); Kuida et al., *Science* 267: 2000-2003 (1995)). Irf3_$^{-/-}$ mice were provided by C. B. Lopez and were previously described (Sato et al., *Immunity* 13: 539-548 (2000)). We used 8-10 week old animals for all experiments. All experiments were approved by the institutional ethics committee and carried out in agreement with the "Guide for the Care and Use of Laboratory Animals" (NIH publication 86-23, revised 1985).

Bacteria

*E. coli* K12, strain DH5α cells were purchased from Invitrogen. Naturally occurring Thymidine auxotrophs (ThyA⁻) were selected on Luria-Bertani (LB) agar plates containing 50 µg/ml trimethoprim and 500 µg/ml thymidine (both SIGMA). Auxotrophy was confirmed by inoculation and overnight culture of single colonies in LB medium. ThyA⁻ *E. coli* cells grew only in the presence of thymidine and were resistant to trimethoprim. For phagocytosis experiments, ThyA⁻ *E. coli* cells were grown to mid-log phase, washed 3 times in phosphate buffered saline (PBS) to remove thymidine and LB salts prior to addition to cells. For heat killing, ThyA⁻ *E. coli* cells were grown to log phase, washed and resuspended in PBS at an OD600 of 0.6, and subsequently incubated at 60° C. for 60 minutes. ThyA⁻ heat killed (HK) *E. coli* cells were stored up to 18 hours at 4° C. or used immediately after cooling. Efficient killing was confirmed by overnight plating on thymidine/trimethoprim supplemented LB-agar plates. For gentamicin killing, ThyA⁻ *E. coli* cells were grown to mid-log phase, washed and resuspended in LB medium containing thymidine, trimethoprim and 50 µg/ml gentamicin sulfate and incubated in a shaking incubator at 37° C. overnight. Ethanol killing was carried out by resuspending log phase ThyA⁻ *E. coli* in 70% Ethanol for 10 minutes, followed by extensive washing in PBS. For UV killing, log phase ThyA⁻ *E. coli* cells were resuspended in PBS at an OD600 of 0.6, UV-irradiated with 1000 mJ/cm² in a Petri dish followed by washing with PBS. Paraformaldehyde (PFA) fixation was performed by resuspending log phase ThyA⁻ *E. coli* in 4% PFA in PBS for 10 minutes followed by extensive washing and resuspension in PBS. *Shigella flexneri* virulence plasmid-cured strain BS103 was kindly provided by M. B. Goldberg. Wing et al., *J Bacteriol* 186: 699-705 (2004); Maurell et al., *Infect Immun* 49: 164-171 (1985). ThyA⁻ *S. flexneri* cells were selected similarly to *E. coli* ThyA⁻. D. M. Monack kindly provided *Salmonella typhimurium*, strain SL1344 ΔSpi1ΔSpi2, lacking the *Salmonella* pathogenicity island SPI-1 and SPI-2 Type-III secretion systems (Haraga et al., *Nat Rev Microbiol* 6: 53-66 (2008)). SL1344 ΔSpi1ΔSpi2 was grown in LB medium containing 25 µg/ml kanamycin and 12 µg/ml tetracycline. *Listeria monocytogenes* ΔHlyΔfliC lacking listeriolysin O (LLO) and flagellin expression were kindly provided by D. Portnoy (Schnupf et al., *Microbes Infect* 9: 1176-1187 (2007)).

Treatment of Macrophages and Dendritic Cells with Viable and Killed Bacteria

Macrophages were detached and re-plated 4 hours prior to the experiment. BMDC were re-plated immediately before addition of bacteria or soluble ligands. Unless stated otherwise, bacteria were used at a multiplicity of infection (MOI) of 20. All experiments were carried out in antibiotic-free "complete medium." One hour after addition of bacteria, penicillin (100 µg/ml) and streptomycin (100 µg/ml) were added to the medium in order to kill any remaining extracellular bacteria. Alternatively, gentamicin sulfate (50 µg/ml) was used. We also compared this approach to washing the cells and replacing the antibiotic-free medium with penicillin/streptomycin containing medium after one hour and found no differences with regards to the cellular responses measured. Supernatants were collected 24 hours after addition of the bacteria unless stated otherwise in the figure legends.

Cytokine Enzyme-Linked Immunoabsorbent Assays (ELISA)

Supernatants from cultured BMM or BMDC were collected at 24 hours after stimulation or at the times indicated. ELISA antibody (Ab) pairs used for IL-6, IL-1β and TNF-α were as listed below. All ELISA Abs were used at 2 µg/ml capture and 0.5 µg/ml detection, with the exception of IL-6 capture, which was used at 1 µg/ml. Detection antibodies were biotinylated and labeled by streptavidin-conjugated horseradish peroxidase (HRP), and visualized by addition of o-phenylenediamine dihydrochloride (SIGMA) (from tablets) or 3,3',5,5'-tetramethylbenzidine solution (TMB, KPL). Color development was stopped with 3 M $H_2SO_4$ or TMB-Stop Solution (KPL), respectively. Recombinant cytokines served as standards and were purchased from Peprotech. Absorbances at 492 or 450 nm were measured, respectively, on a tunable microplate reader (VersaMax, Molecular Devices). Cytokine supernatant concentrations were calculated by extrapolating absorbance values from standard curves where known concentrations were plotted against absorbance using SoftMax Pro 5 software. Capture/detection Ab pairs were as follows: IL-6, MP5-20F3/MP5-32C11 (BDPharmingen); IL-1β, B12/rabbit polyclonal Ab (eBioscience); TNF-α, TN3-19/rabbit polyclonal Ab (eBioscience). IFN-β production was measured from supernatants using the VeriKine™ Mouse IFN-Beta ELISA Kit (PBL Interferon source) following manufacturer's instructions.

Anti-E. coli Antibody ELISA 96-well microtiter plates were coated overnight with E. coli lysates (3 µg/ml) that we generated from log-phase cultures of ThyA⁻ E. coli. Serum samples from immunized mice were serially diluted (12 dilutions) and incubated in the pre-coated plates for 12 hours at 4° C. followed by washing and incubation with rabbit anti-mouse isotype specific Ig-HRP (Southern Biotech) for 1 hour. Bound rabbit anti-mouse Ig-HRP was visualized by addition of o-phenylenediamine dihydrochloride (SIGMA) from tablets, and the anti-E. coli antibody titers for each mouse were determined by absorbance readings at 490 nm.

Measurement of Inflammatory Cell Death

Cell death of macrophages or BMDC was measured using the Cytotox96 cytotoxicity assay (Promega) following manufacturer's instructions. The assay measures release of lactate dehydrogenase (LDH) into the supernatant calculated as percent of total LDH content, measured from cellular lysates (100%). LDH released by unstimulated cells was used for background correction.

Flow Cytometric Assessment of Cell Death

Cells were stimulated overnight, stained for Annexin V/7AAD using the Annexin V-PE/7AAD Apoptosis Detection kit (BD Pharmingen), and analyzed by flow cytometry (FACSCalibur, BD).

Flow Cytometric Measurement of Reactive Oxygen Species (ROS)-Production

BMMs were loaded with the ROS indicator dye H2DCFDA (Molecular Probes/Invitrogen, 10 mM in PBS) for 30 min followed by a recovery time of 30 min in fresh pre-warmed "complete medium." BMMs were then stimulated with viable or HK E. coli for 60 min, washed and analyzed by flow cytometry (FACSCalibur, BD).

Western Blots

For detection of Caspase-1, protein extracts were separated on 4-12% SDS-gradient gels (Invitrogen). For detection of all other proteins, samples were run on 10% SDS-polyacrylamide gels. Proteins were transferred to PVDF membranes (Millipore). Membranes were blocked with 5% milk in PBS and probed with the following Abs: Caspase-1 p10 (M-20)/rabbit polyclonal Ab, IκB-α (C-21)/rabbit polyclonal Ab (both from Santa Cruz Biotechnologies), Phospho-IRF3 (Ser396)/rabbit polyclonal Ab, IRF3/rabbit polyclonal Ab, Phospho-p38 MAPK (Thr180/Tyr182)/rabbit polyclonal Ab, p38 MAPK/rabbit polyclonal Ab (all from Cell Signalling Technology), α-tubulin (DM1A)/rabbit monoclonal Ab (Novus Biologicals).

Real Time PCR

Total RNA was isolated from macrophages using the RNeasy kit (QIAGEN). Contaminating genomic DNA was removed by DNase digestion (DNase I, Promega). Reverse transcription was performed using Superscript III (Invitrogen) and cDNA was used for subsequent real time PCR reactions. Quantitative real-time RT-PCR was conducted on an ABI Prism 7900 instrument using the Maxima™ SYBR green qPCR Master Mix (Fermentas) with the following primer pairs. β-Actin: FW 5'-GAAGTCCCTCACCCTC-CCAA-3' (SEQ ID NO:1), RV 5'-GGCATGGACGC-GACCA-3' (SEQ ID NO:2); Il1b: FW 5' AAAGACGGCA-CACCCACCCTGC-3' (SEQ ID NO:3), RV 5' TGTCCTGACCACTGTTGTTTCCCAG-3' (SEQ ID NO:4); Ifnb: FW 5' GCACTGGGTGGAAT 3' (SEQ ID NO:5), RV 5' TTCTGAGGCATCAA 3' (SEQ ID NO:6); Nlrp3: FW 5' CGAGACCTCTGGGAAAAAGCT 3' (SEQ ID NO:7), RV 5' GCATACCATAGAGGAATGTGATG-TACA 3' (SEQ ID NO:8). All reactions were performed in duplicates and the samples were normalized to β-actin. "Fold inductions" were calculated using the $\Delta\Delta C^t$ method relative to unstimulated BMMs.

Transcriptome Analysis

BMMs derived from wild type (wt) or Trif⁻/⁻ mice were stimulated with viable E. coli for 0, 1, 3 or 6 hours and total RNA was extracted using the RNeasy kit (QIAGEN). RNA from three independent experiments was used for transcriptional analysis. RNA integrity was checked on an Agilent 2100 Bioanalyzer (Agilent Technologies, Amsterdam, The Netherlands) with 6000 Nano Chips. RNA was judged as suitable only if samples showed intact bands of 18S and 28S ribosomal RNA subunits, displayed no chromosomal peaks or RNA degradation products, and had a RNA integrity number (RIN) above 8.0.

One hundred nanograms of RNA were used for whole transcript cDNA synthesis with the Ambion WT expression kit (Applied Biosystems, Nieuwekerk a/d IJssel, The Netherlands). Hybridization, washing and scanning of an Affymetrix GeneChip Mouse Gene 1.1 ST 24-array plate was carried out according to standard Affymetrix protocols on a GeneTitan instrument (Affymetrix, Santa Clara, Calif.).

Packages from the Bioconductor project, integrated in an in-house developed management and analysis database for microarray experiments, were used for analysis of the scanned arrays (Gentleman et al., *Genome Biol* 5, R80 (2004)). Arrays were normalized using the Robust Multi-array Average method (Bolstad et al., *Bioinformatics* 19: 185-193 (2003); Irizarry et al., *Nucleic acids research* 31: e15 (2003)). Probe sets were defined according to Dai et al., *Nucleic acids research* 33: e175 (2005). With this method probes are assigned to unique gene identifiers, in this case Entrez IDs. The probes on the Gene 1.1 ST arrays represent 19,807 genes that have at least 10 probes per identifier. For the analysis, only genes that had an intensity value of ≥20 on at least two arrays were taken into account. In addition, the interquartile range of log 2 intensities had to be at least 0.25. These criteria were met by 9,921 genes. Changes in gene expression are represented as signal log ratios between treatment and control. Multiple Experiment Viewer software (MeV 4.6.1) was used to create heatmaps (Saeed et al. *Biotechniques* 34, 374-378 (2003); Saeed, A. I., et al. *Methods Enzymol* 411, 134-193 (2006)). Genes were clustered by average linkage hierarchical clustering using Pearson correlation. Significantly regulated genes were identified by Intensity-based moderated t-statistics (Sartor et al., *BMC Bioinformatics* 7: 538 (2006)). Obtained p-values were corrected for multiple testing by a false discovery rate method (Storey et al., *Proc Natl Acad Sci USA* 100: 9440-9445 (2003)).

IFN-regulated genes were identified using the Interferome database (interferome.org) (Samarajiwa et al., *Nucleic acids research* 37: D852-857 (2009)) and grouped in a heat map. Rel/NF-κB target genes were identified using another online database (bioinfo.lifl.fr/NF-κB/) which compiles Rel/NF-κB target genes identified by various groups (Pahl, *Oncogene* 18: 6853-6866 (1999)). Inflammasome-related genes were compiled based on the current literature (Schroder et al., *Cell* 140: 821-832 (2010); Coll et al., *J Innate Immun* 2: 406-421 (2010)).

Measuring Release from Bacterial Phagosomes

Measurement of fluorescein-dextran (Fdx) release from macrophage phagosomes was performed using a modified method previously described (Davis et al., *J Leukoc Biol* 88: 813-822 (2010)). BMMs were plated onto Mat-tek coverslip dishes (MatTek Corp. Ashland, Mass., USA) and incubated overnight. BMMs were stimulated with viable or gentamicin-killed red fluorescent protein (RFP)-expressing ThyA$^-$ *E. coli* in the presence of 0.167 mg/mL Fdx in 200 µL of medium. After 120 minutes of co-culture, additional Fdx and gentamicin containing medium was added to the coverslip dishes to prevent drying and to prevent bacterial overgrowth. Cells were imaged after 2, 4 and 8 hours to measure release of Fdx. Microscopic imaging was performed on an IX70 inverted microscope (Olympus, Center Valley, Pa., USA) equipped with an X-cite 120 metal halide light source (EXFO, Mississauga, ON, Canada) and excitation and emission filter wheels. Phase contrast and two fluorescent images were acquired for each field of cells. The fluorescent images used the same emission settings, but used different excitation band-pass filters. Fdx fluorescence intensity using an excitation filter centred at 440 nm is relatively insensitive to pH, while fluorescence intensity using an excitation filter centered at 485 is very sensitive to pH. The ratio of fluorescence intensity at 485 nm divided by 440 nm was converted to into pH maps using calibration curves generated by imaging BMM with Fdx containing compartments at a series of fixed pH conditions. As described previously (Davis et al., *J Leukoc Biol* 88: 813-822 (2010)), pixels with pH above 5.5 were designated as representing Fdx which has been released from endo-lysosomal compartments. Percent of Fdx release was calculated by dividing the total intensity of pixels containing released Fdx by the total Fdx intensity for each cell.

Infections and Vaccinations

For measuring systemic cytokine levels, C57BL/6J wt, Trif$^{-/-}$, Asc$^{-/-}$ or Nlrp3$^{-/-}$ mice were injected with $1 \times 10^9$ viable or $5 \times 10^9$ HK ThyA$^-$ *E. coli*, respectively. Blood samples were drawn 6 hours post infection, and cytokine concentrations were measured by ELISA. For determination of bacterial clearance, we infected mice with $5 \times 10^7$ viable replication-sufficient *E. coli* by intraperitoneal injection. Mice were monitored daily and moribund animals were sacrificed according to humane criteria established and approved by our institutional IACUC committee. After 60 hours, animals were euthanized and the spleens were explanted, homogenized, serially diluted and plated on LB-agar plates overnight followed by colony forming units (cfu) counting.

Figure 28:
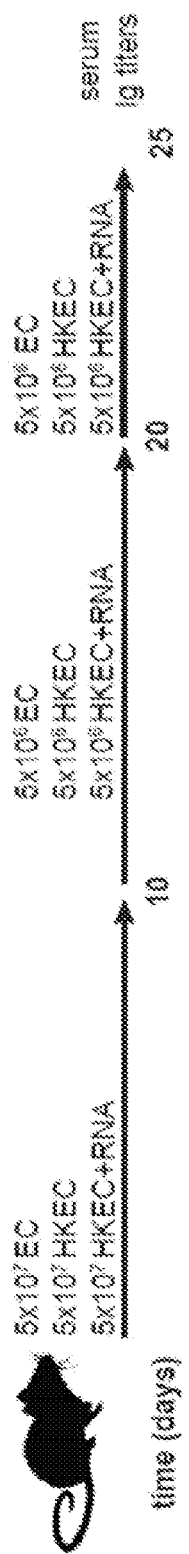
FIG. 28. Schematic of vaccination regimen used for immunizations shown in FIG. 4h.

For vaccinations, we followed a prime-boost regimen as shown in the schematic in FIG. 28 that was adopted from a previous study (Lim et al., *Journal of Immune Based Therapies and Vaccines* 4: 5 (2006)). In brief, mice received an initial vaccination intraperitoneally with $5 \times 10^7$ cfu of viable or HK ThyA$^-$ *E. coli* or a combination of $5 \times 10^7$ cfu HK ThyA$^-$ *E. coli* and 30 µg of purified *E. coli* total RNA, followed by two boosts ($5 \times 10^6$ cfu) after 10 and 20 days. Polyclonal class-specific anti-*E. coli* antibody production was measured in the serum after 25 days by ELISA.

Bacterial RNA

Total bacterial RNA was isolated from ThyA$^-$ *E. coli* using the e.z.n.a. Bacterial RNA Kit (Omega Bio-Tek), following the manufacturer's instructions. Contaminating DNA was removed by DNase digestion (TURBO DNase, Ambion/Applied Biosystems). Alternatively, total purified *E. coli* (DH5α) RNA was purchased from Ambion/Applied Biosystems, and similar results were obtained. Fractionation of bacterial RNA species was performed as follows. First, ribosomal 16S and 23S RNA (rRNA) was removed by a magnetic bead based capture hybridization approach using the MICROBExpress™ kit (Ambion/Applied Biosystems). The enriched RNA was then separated into messenger RNA (mRNA) and small RNA (sRNA, including 5S rRNA) using the MEGAClear™ kit (Ambion/Applied Biosystems). All separated RNA fractions were precipitated with ammonium acetate and resuspended in nuclease free water. RNA concentration and purity were determined by measuring the absorbance at 260/280 and 260/230 nm. RNA preparations were further visualized by 1% agarose gel electrophoresis.

In Vitro RNA Transcription

The *E. coli* Gro-operon encoding the bacterial chaperonins GroEL and GroES, the GTPase Era-operon or the DNA-polymerase-III-operon were PCR amplified from genomic DNA isolated from ThyA$^-$ *E. coli* using primer pairs containing a T7 promotor sequence (T7) in either the FW or both FW and RV primer. The following primers were used.

Gro-FWT7:
(SEQ ID NO: 9)
5'-TAATACGACTCACTATAGGGCACCAGCCGGGAAACCACG-3';

Gro-RVT7:
(SEQ ID NO: 10)
5'-TAATACGACTCACTATAGGAAAAGAAAAACCCCCAGACAT-3';

Gro-RV:
(SEQ ID NO: 11)
5'-AGATGACCAAAAGAAAAACCCCCAGACATT-3';

Era-FWT7:
(SEQ ID NO: 12)
5'-TAATACGACTCACTATAGGGCATATGAGCATCGATAAAAGTTAC-3';

Era-RV:
(SEQ ID NO: 13)
5'-TTTAAAGATCGTCAACGTAACCGAG-3';

DNApol-FWT7:
(SEQ ID NO: 14)
5'-TAATACGACTCACTATAGGGATGTCTGAACCACGTTTCGT-3';
and DNApol-RV:
(SEQ ID NO: 15)
5'-AGTCAAACTCCAGTTCCACCTGCTCCGAA-3'.

PCR fragments were purified using Nucleospin Extract II PCR purification kit (Macherey-Nagel), and used as DNA templates for in vitro transcription. In vitro transcription was performed using MEGAscript kit T7 (Ambion/Applied Biosystems) following the manufacturer's instructions. DNA templates generated with Gro-FWT7 and Gro-RV primers only contained a T7 promotor site in the sense strand and yielded single-stranded RNA, whereas PCR templates generated with Gro-FWT7 and Gro-RVT7 primers contained T7 promotor sequences in both strands, allowing transcription of two complementary strands, yielding double-stranded RNA. For generation of 5'-capped RNA, m7G(5')ppp(5')G cap analog (Ambion/Applied Biosystems) was included in the transcription reaction at a GTP:cap ratio of 1:4.

RNA Digestion, Dephosphorylation and Polyadenylation

In vitro transcribed Gro RNA, total *E. coli* RNA or *E. coli* mRNA were digested using RNase I (Promega) and RNase III (Ambion/Applied Biosystems). To remove 5'-triphosphates, RNA dephosphorylation was performed by incubating 10 µg in vitro transcribed RNA or total *E. coli* RNA or 1 mg of *E. coli* mRNA with 30 U of calf intestinal alkaline phosphatase (CIP, New England Biolabs) for 2 hours at 37° C., as described previously (Hornung et al., *Science* 314: 994-997 (2006)). Polyadenylation of in vitro transcribed and purified bacterial mRNA was performed using the poly(A) Tailing kit (Ambion) following the manufacturer's instructions.

Transfection of Macrophages and MEFs

For direct cytosolic delivery of total purified *E. coli* RNA or in vitro transcribed Gro RNA, $5 \times 10^5$ BMM or $2 \times 10^5$ MEFs were transfected with 1 mg of RNA using 2 µl of Lipofectamine 2000 (Invitrogen) in 24- or 12-well plates, respectively.

Soluble Ligands, Inhibitors and Other Reagents

Lipopolysaccharide (LPS) was purchased from SIGMA (*E. coli* 055:B5, phenol extracted). Caspase inhibitors z-YVAD, z-IEDT, Q-VD-OPH (all SM Biochemicals) were used at 50 µM, and added 30' prior to stimulation of cells.

Poly (I:C)

Poly (I:C) was purchased from Invivogen. Poly(I:C) is composed of a strand of poly(I) annealed to a strand of poly(C). Poly(I:C) (HMW) with a high molecular weight has an average size of 1.5-8 kb. Poly(I:C) (LMW) with a low molecular weight has an average size of 0.2-1 kb.

Statistical Analysis

Statistical significances were tested by ANOVA Kruskall-Wallis test and Bonferroni-Dunn post hoc correction. Significances are represented in the figures as follows: *, p≤0.05; , p≤0.01; *, p≤0.001. "n.s.," not statistically significant; #, "Not detected."

Experimental Results

Figure 7:
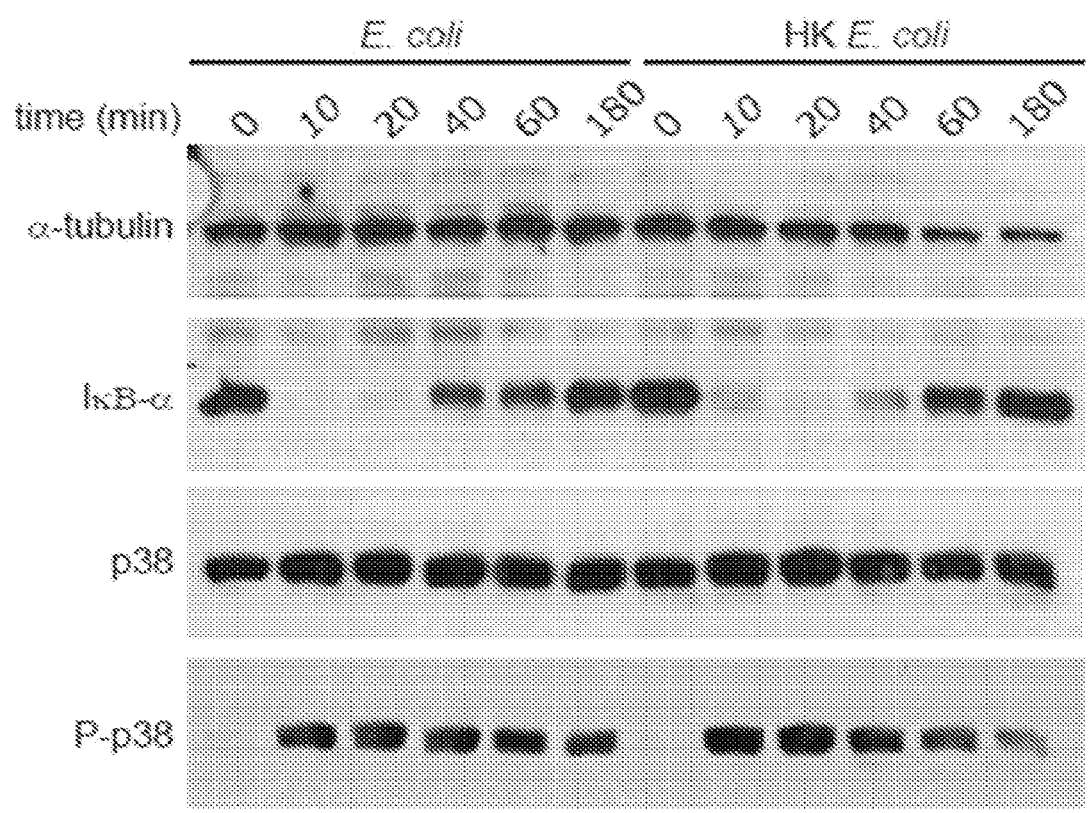
FIG. 7. Viable and heat killed $E.$ $coli$ induce NF-κB and MAPK activation. BMM were stimulated with viable or heat killed (HK) ThyA⁻ $E.$ $coli$ for the indicated times. Cellular lysates were immunoblotted and probed for the indicated proteins. As a readout for NF-κB activation, IκB-α degradation was observed 10 minutes post stimulation with either viable or HK ThyA⁻ $E.$ $coli$, and its re-synthesis restored detection at 40 minutes. MAPK activation was assessed by examining the phosphorylation of p38 (P-p38) which was detected beginning at 10 minutes after stimulation with either viable or HK ThyA⁻ $E.$ $coli$.
Figure 8:
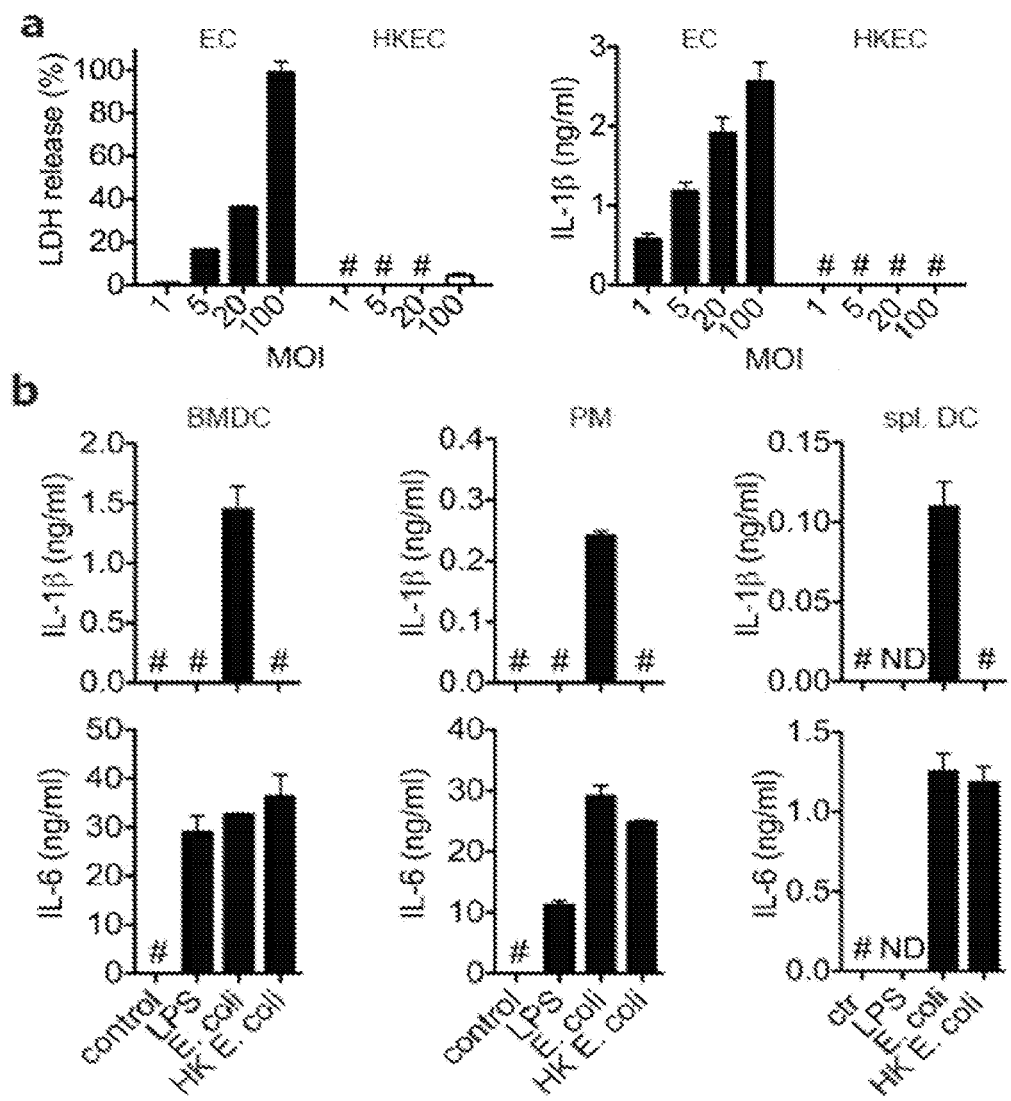
FIG. 8. Viability-induced responses are dose-dependent and not restricted to BMM. (a) BMM were stimulated with viable or heat killed (HK) ThyA⁻ $E.$ $coli$ at the indicated multiplicities of infection (MOI) for 24 hours. (b) BMDC, peritoneal macrophages (PM) and splenic DC (spl. DC) were incubated with LPS (100 ng/ml), viable or heat killed (HK) ThyA⁻ $E.$ $coli$ for 24 hours. Lactate dehydrogenase (LDH), IL-1β and IL-6 production were measured in the supernatants by ELISA. #; 'not detected', ND; not determined. All bars represent mean±s.e.m.
Figure 9:
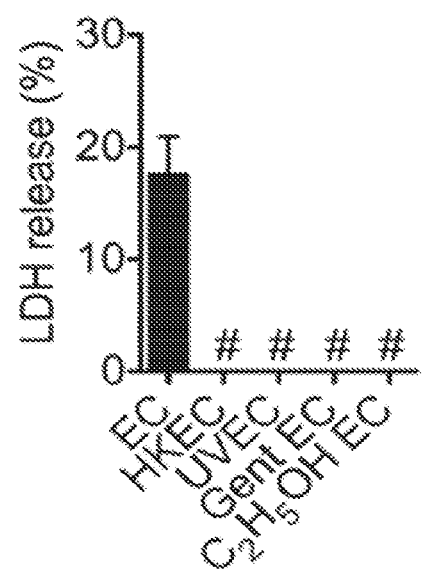
FIG. 9. Viable but not killed bacteria induce pyroptosis irrespective of mode of death. BMM were incubated with viable ThyA⁻ $E.$ $coli$ (EC) or ThyA⁻ $E.$ $coli$ killed by various means prior to addition to BMM. ThyA⁻ $E.$ $coli$ were killed by heat (HKEC), UV irradiation (UVEC), treatment with Gentamicin sulfate (Gent EC), or 70% Ethanol (C2H5OH EC). LDH release was measured in the supernatant 24 hours later. #; 'not detected'.

We hypothesized that the innate immune system may sense the most fundamental characteristic of microbial infectivity, microbial viability itself, and activate a robust immune response regardless of the presence of more specialized factors that regulate microbial virulence (Vance, et al., *Cell Host Microbe* 6: 10-21 (2009)). To study sensing of bacterial viability without compounding effects of replication or virulence factors, we used thymidine auxotrophs of non-pathogenic *Escherichia coli* K12, strain DH5α (ECThyA⁻). Viable and heat-killed (HK) ECThyA⁻ similarly activated nuclear factor-κB (NF-κB) and mitogen-activated protein kinase p38 (FIG. 7) in bone marrow-derived macrophages and elicited production of similar amounts of interleukin-6 (IL-6) and tumor necrosis factor alpha (TNF-α) (FIG. 1a). However, viable ECThyA⁻ induced higher levels of IFN-β than HK ECThyA⁻ or lipopolysaccharide (LPS) (FIG. 1b), and only viable ECThyA⁻ induced IL-1β secretion (FIG. 1c; FIG. 8). Pro-IL-1β transcription was equally induced by both viable and HK ECThyA⁻ (FIG. 1c), suggesting that viable bacteria specifically elicit cleavage of pro-IL-1β. This process is catalyzed by caspase-1 in Nod-like receptor (NLR)-containing inflammasome complexes, assembly of which can be triggered by the activity of bacterial virulence factors (Mariathasan et al., *Nat Rev Immunol* 7:31-40 (2007); Schroder et al., *Cell* 140:821-832 (2010)). Notably, avirulent viable but not HK ECThyA⁻ induced inflammasome activation and pro-caspase-1 cleavage (FIG. 1d). Finally, viable but not HK ECThyA⁻ induced caspase-l-dependent inflammatory cell death, termed pyroptosis (Mariathasan et al., *Nat Rev Immunol* 7: 31-40 (2007); Schroder, et al., *Cell* 140: 821-832 (2010)), resulting in release of lactate dehydrogenase (LDH) (FIG. 1e) and appearance of 7-amino-actinomycin D (7AAD)⁺Annexin-V$^{-/low}$ cells (FIG. 1f). Similar responses were observed in peritoneal macrophages and both splenic and bone marrow-derived dendritic cells (FIG. 8b). Killing ECThyA⁻ by UV irradiation, antibiotics, or ethanol, also selectively abrogated IL-1β secretion and pyroptosis without affecting IL-6 production (FIG. 1g; FIG. 9), suggesting that a general determinant associated with bacterial viability is detected.

Figure 5:
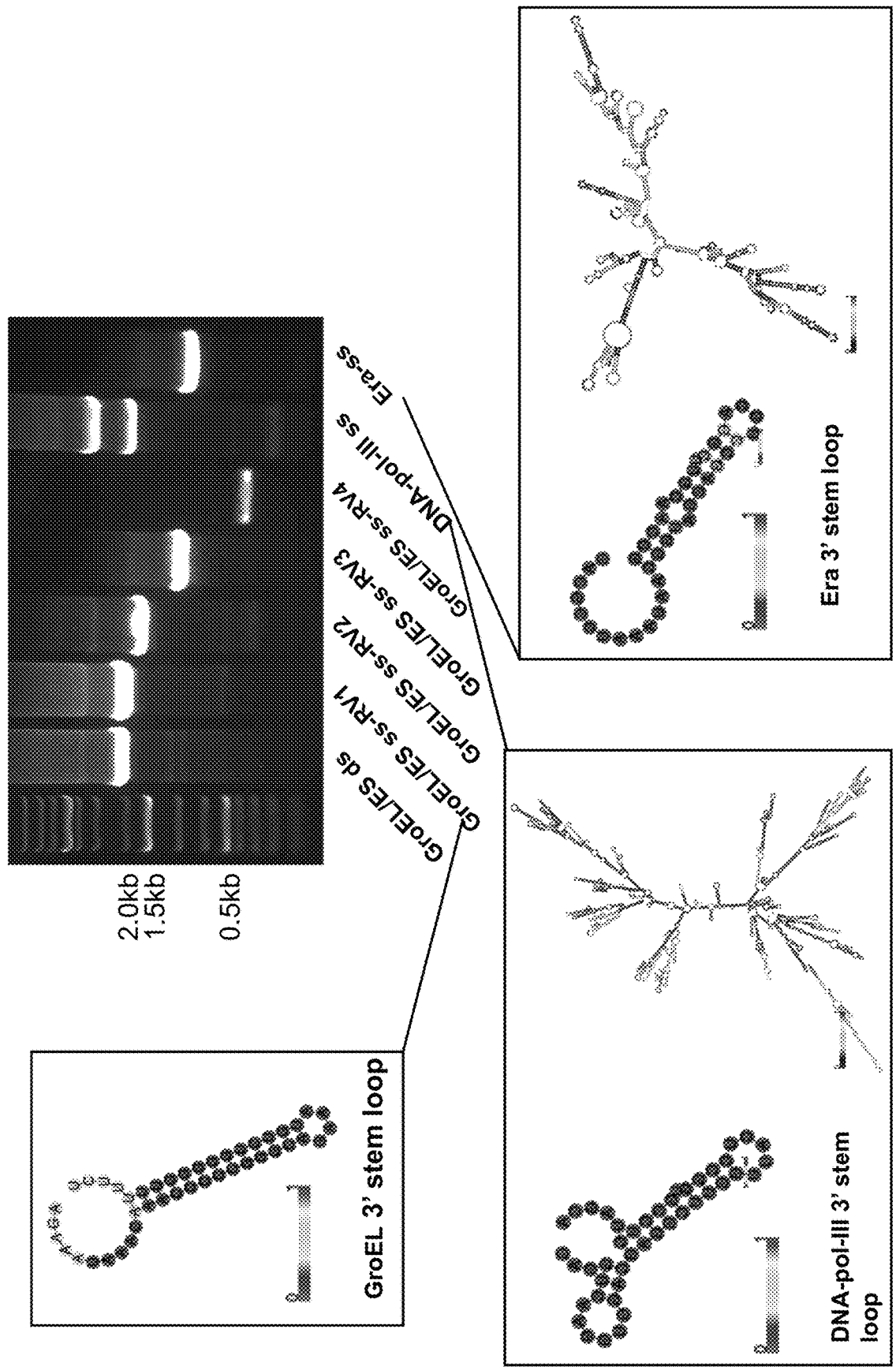
FIG. 5. Various in vitro transcribed RNAs. The photo shows an agarose gel electrophoresis of DNA templates generated by PCR, using genomic *E. coli* DNA as a template. These templates contain T7-polymerase consensus sites in either one strand (GroEL/ES-ssRV1-RV4, DNA-pol III-ss, Era-ss) or both strands (GroEL/ES-ds), which allows in vitro transcription of RNA using recombinant T7 RNA polymerase. The images show predicted secondary structures of the RNA transcripts using the "RNA fold server" at the website rna.tbi.univie.ac.at/cgi-bin/RNAfold.cgi. The entire structure is shown for DNA pol III-ss and Era-ss. In addition, amplifications of the 3'-stem loop structures of GroEL/ES-ss RV1 (full length transcript of the GroEL/ES-operon), DNA pol III-ss, and Era-ss are shown. GroEL/ES-ss-RV2-4 are shorter transcripts, lacking the 3' end of the full length transcript.

To determine whether pathogenic bacteria can also activate the inflammasome in the absence of virulence factors, we studied attenuated strains of selected pathogens: *Shigella flexneri* virulence plasmid-cured strain BS103 (Wing et al., *J Bacteriol* 186: 699-705 (2004)), *Salmonella typhimurium*, SL1344ΔSpi1ΔSpi2, lacking the *Salmonella* pathogenicity islands SPI-1 and SPI-2 (Mariathasan et al., *Nat Rev Immunol* 7: 31-40 (2007)), and *Listeria monocytogenes* ΔHlyΔfliC, lacking listeriolysin O and flagellin (Mariathasan et al., *Nat Rev Immunol* 7: 31-40 (2007)). These mutants induced IL-1β production at levels comparable to those induced by ECThyA⁻ (FIG. 1h; FIG. 5), but lower and with slower kinetics than their pathogenic counterparts (FIG. 10; FIG. 5). IL-1β production was abolished when these bacteria were killed, whereas IL-6 production was similar (FIG. 1h). Thus, immune cells detect universal characteristics of viability different from virulence factors.

Figure 11:
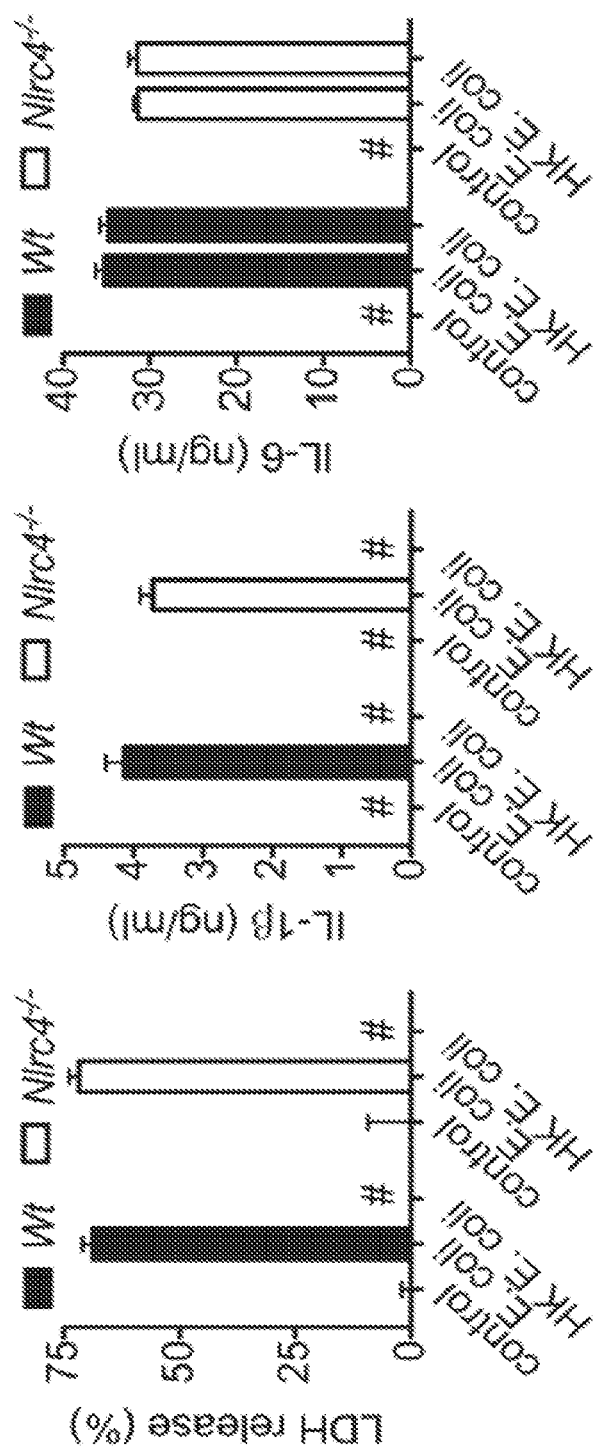
FIG. 11. Pyroptosis and IL-1β secretion induced by viable avirulent $E.$ $coli$ are independent of the Nod-like receptor NLRC4. BMDC derived from wt or Nlrc4$^{-/-}$ mice were incubated with viable or heat killed (HK) ThyA⁻ $E.$ $coli$. Cell culture supernatants were harvested after 24 hours and pyroptosis was determined by measurement of LDH release. IL-1β and IL-6 secretion was measured by ELISA. #; 'not detected'.
Figure 12:
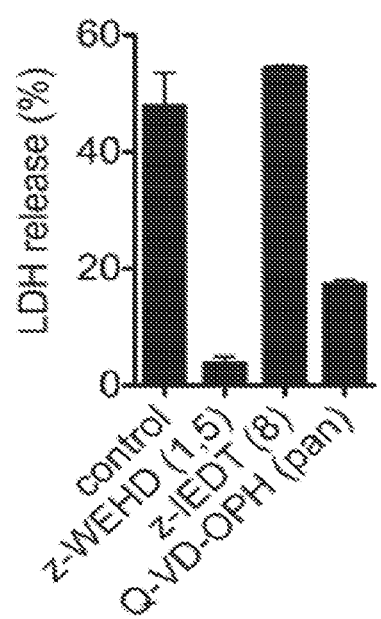
FIG. 12. Pyroptosis induced by $E.$ $coli$ is mediated by caspase-1 and is independent of caspase-8. BMM were incubated with viable ThyA⁻ $E.$ $coli$ and the indicated caspase inhibitors. The specificitics of inhibitors z-WEHD, z-IEDT and Q-VD-OPH to various caspases are indicated in parentheses. Pyroptosis was determined by measurement of LDH release at 24 hours.

Caspase-1 activation, pyroptosis and IL-10 production in response to ECThyA⁻ were abrogated in macrophages deficient for NLRP3 or for the inflammasome adaptor Apoptosis Speck protein with Caspase recruitment (ASC or PYCARD) (Schroder et al., *Cell* 140: 821-832 (2010)) (FIGS. 1i and 1j), while NLRC4 was dispensable (FIG. 11). Pyroptosis and IL-1β production induced by viable ECThyA⁻ were abrogated in Casp1⁻/⁻ macrophages (FIG. 1j) and suppressed by inhibitors for caspase-1, but not caspase-8 (FIG. 12).

Figure 2:
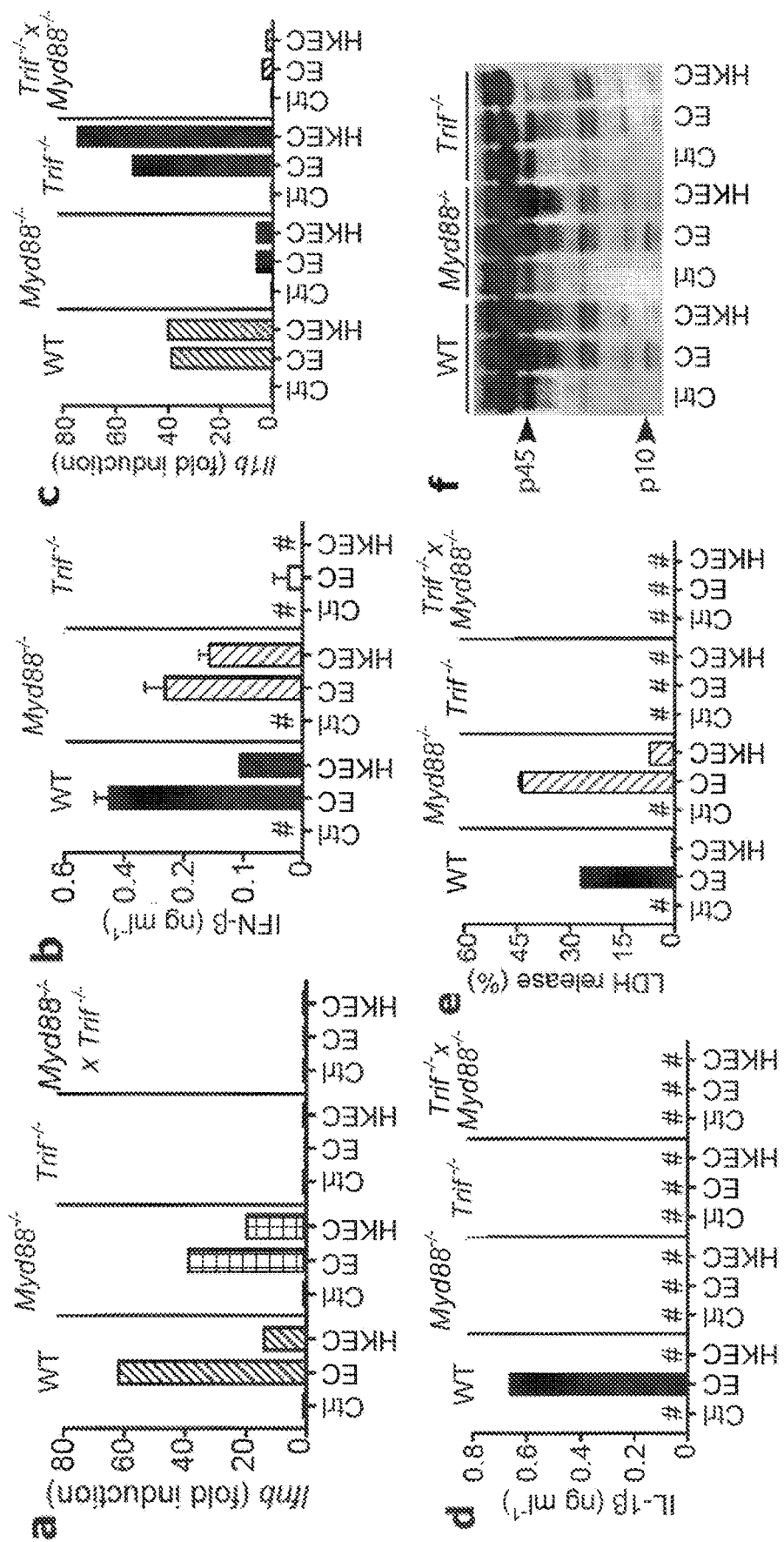
FIG. 2. The TLR signalling adaptor TRIF controls 'viability-induced' responses. Ifnb transcription at 2 h (a), IFN-β secretion at 24 h (b), Il1b transcription at 2 h (c), IL-1β secretion (d), and LDH (e) 24 h after phagocytosis of viable or HKEC. f. Caspase-1 immunoblot at 18 h. a-f, data by BMM and represent ≥5 experiments. g. Gene microarray analysis of wt and Trif$^{-/-}$ BMM treated with viable EC for 1, 3 or 6 h (three biological replicates #1-3). Heat map of positive regulators/essential components ('+') and negative regulators ('−') of inflammasomes. h. Nlrp3 transcription at 1 h in BMM. Serum IL-6 and IL-1β 6 h after injection of $1\times10^9$ viable EC or $5\times10^9$ HKEC (i), and splenic bacterial burdens 72 h after injection of $1\times10^8$ non-auxotroph EC (j) into wt, Trif$^{-/-}$ Asc$^{-/-}$ and Nlrp3$^{-/-}$ mice. Each symbol represents one mouse. *; p≤0.05, ; p≤0.01, *; p≤0.001. n.s., Not statistically significant. #, 'Not detected'. All bars represent mean±s.e.m.
Figure 2:
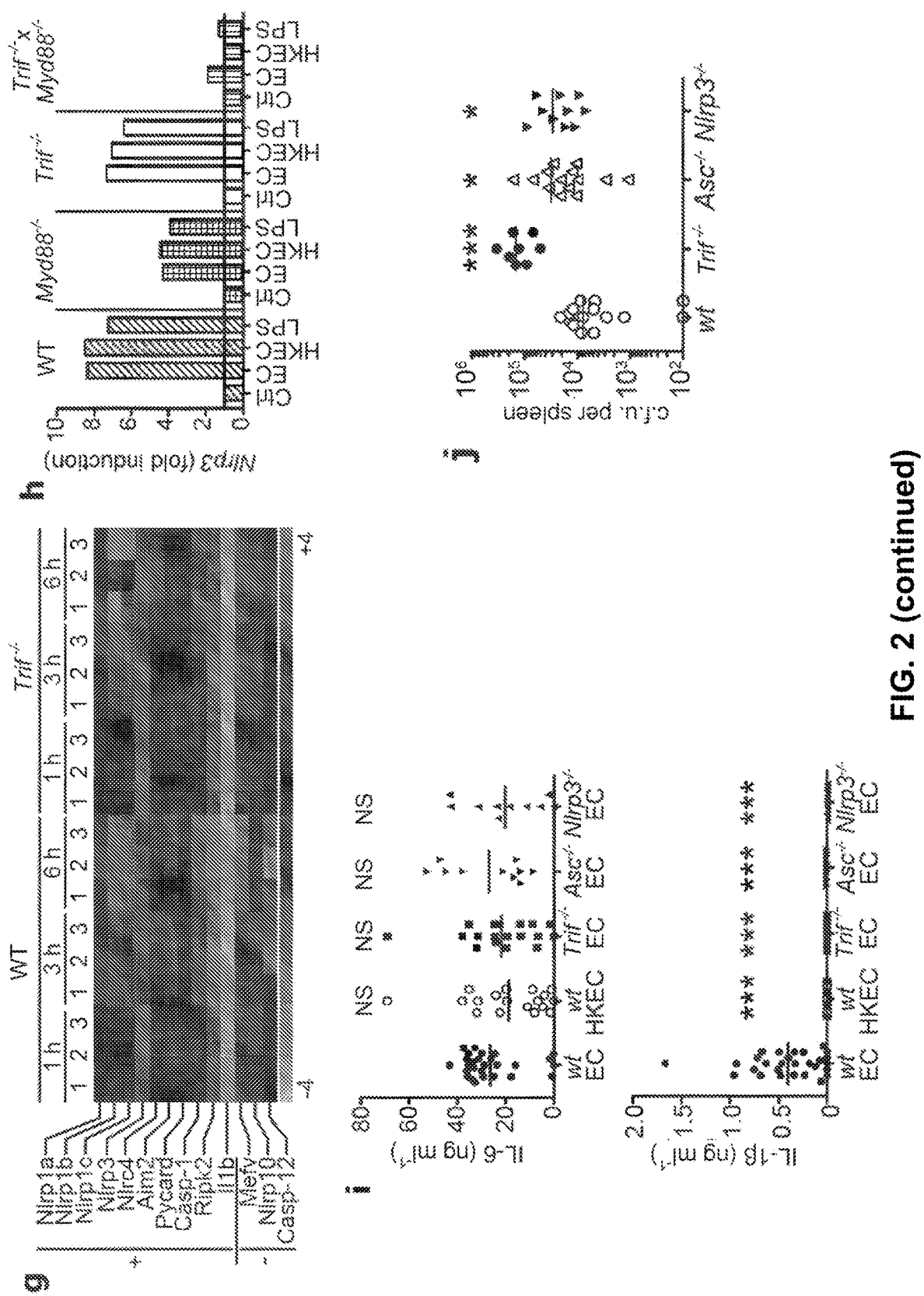
Figure 10:
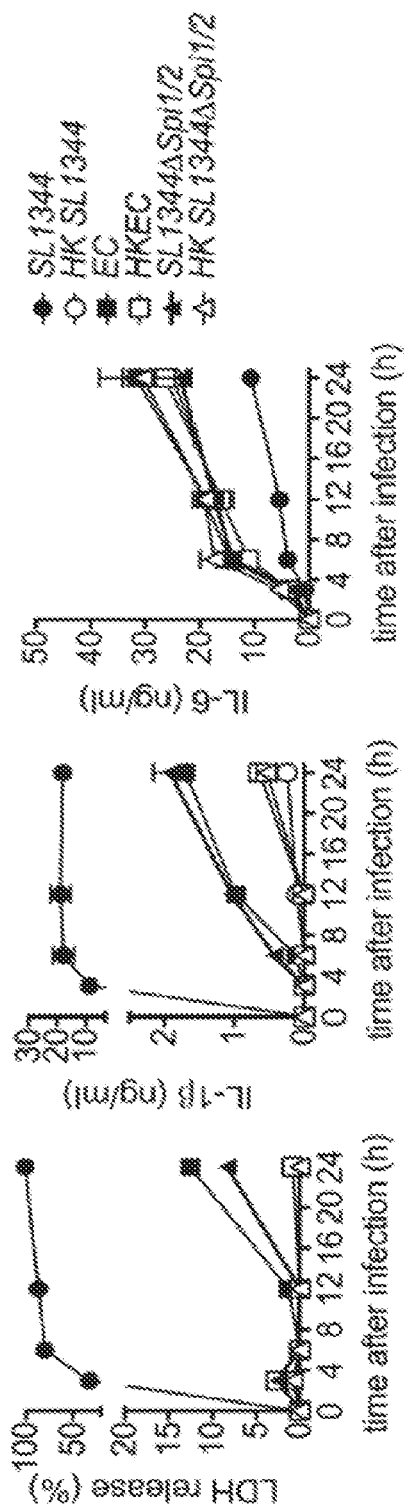
FIG. 10. Different magnitude and kinetics of pyroptosis and IL-1β production in response to viability versus virulence factors. BMM were incubated with the indicated bacteria for the indicated times, and pyroptosis (LDH release, left), IL-1β (middle) and IL-6 production (right) were measured. SL1344 is a wild type (wt) strain of $Salmonella$ $enterica$ serovar $Typhimurium$; SL1344ΔSpi1/2 is a mutant lacking the $Salmonella$ pathogenicity island (SPI) 1 and SPI 2 T3SS. LDH and IL-1β release were observed in response to both avirulent viable ThyA⁻ $E.$ $coli$ and SL1344ΔSpi1/2 indicating a trigger other than virulence factors. On the other hand, wt $Salmonella$ $enterica$ serovar $Typhimurium$ induced high levels of LDH and IL-1β release within 3 hours, known to be T3SS dependent in this case (compare to levels with T3SS mutant SL1344ΔSpi1/2). IL-6 levels were comparable in response to all bacteria except as expected for SL1344, where survival of the BMM was compromised.
Figure 13:
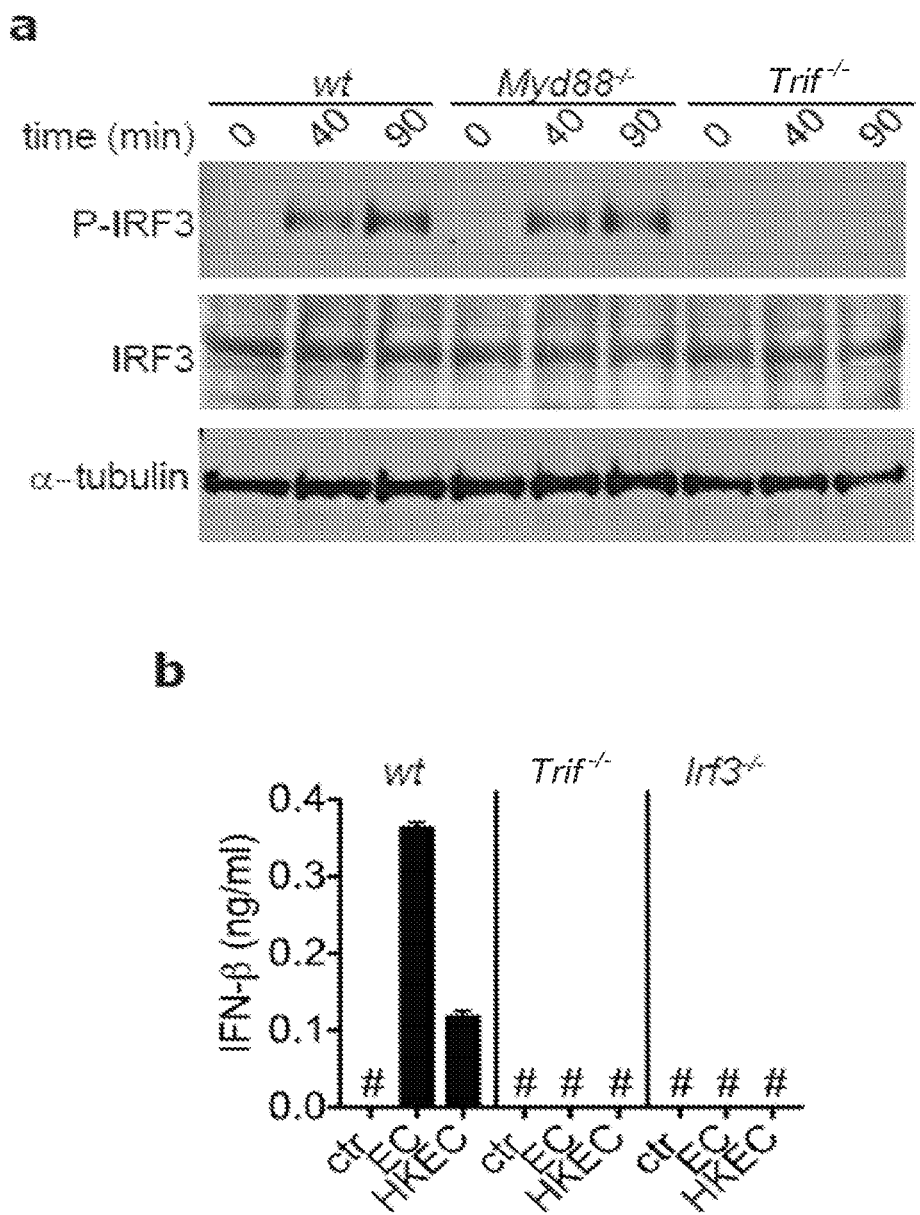
FIG. 13. IFN-β production induced by viable $E.$ $coli$ is dependent on TRIF-IRF3 signalling. (a) BMM derived from wt, Myd88$^{-/-}$ or Trif$^{-/-}$ mice were incubated with viable ThyA⁻ $E.$ $coli$ for the indicated times. Cell lysates were immunoblotted and probed for phosphorylated IRF3 (P-IRF3), total IRF3 and α-tubulin as indicated. (b) BMM derived from wt, Trif$^{-/-}$ or Irf3$^{-/-}$ mice were incubated with viable ThyA⁻ $E.$ $coli$ (EC) or heat killed (HK) ThyA⁻ $E.$ $coli$ (HKEC) or medium alone (ctr). IFN-β production was measured in supernatants after 24 hours by ELISA. #; 'not detected'.
Figure 14:
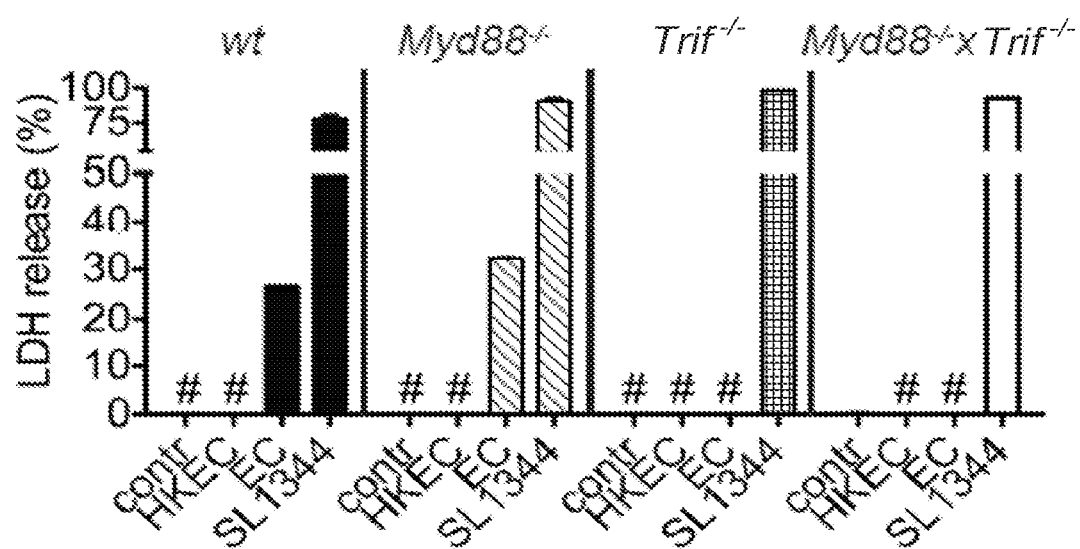
FIG. 14. $Salmonella$ $enterica$ serovar $Typhimurium$ induces pyroptosis in macrophages independently of TLR signalling. BMM derived from wt, Myd88$^{-/-}$, Trif$^{-/-}$ or Myd88$^{-/-}$×Trif$^{-/-}$ mice were incubated with viable ThyA⁻ $E.$ $coli$ (EC), heat killed (HK) ThyA⁻ $E.$ $coli$ (HKEC) or viable $Salmonella$ $enterica$ serovar $Typhimurium$ (SL1344) for 24 hours and LDH release was measured. #; 'not detected'.

Induction of IFN-β mRNA and protein by viable ECThyA⁻ required the Toll-like receptor (TLR) adaptor TRIF (Takeuchi et al., *Cell* 140: 805-820 (2010)) (FIG. 2a,b) and downstream interferon regulatory factor-3 (IRF3) (Takeuchi et al., *Cell* 140: 805-820 (2010)) (FIG. 13), but not MyD88, the main TLR adaptor (Takeuchi et al., *Cell* 140: 805-820 (2010)) (FIG. 2a,b). In contrast, transcription of pro-IL-1β was largely dependent on MyD88. Consequently, Myd88⁻/⁻ cells secreted no IL-1β (FIG. 2c,d), whereas pyroptosis and caspase-1 cleavage were intact (FIG. 2e,f). Notably, while TRIF was dispensable for pro-IL-1β transcription (FIG. 2c), Trif⁻/⁻ cells failed to secrete IL-1β (FIG. 2d), were protected from pyroptosis (FIG. 2c), and did not activate caspase-1 (FIG. 2f). These findings revealed an unexpected role for TRIF in NLRP3 inflammasome activation in response to viable ECThyA⁻. In contrast, pyroptosis induced by pathogenic *S. typhimurium* (Monroe et al., *PLoS Pathog* 5: e1000665 (2009)), proceeded independently of TRIF (FIG. 14). Differential involvement of TRIF, together with differences in magnitude and kinetics of the response (FIG. 1*h*; FIG. 10), indicated that inflammasome activation in response to virulence factors occurs in a manner distinct from that to viability.

Figure 15:
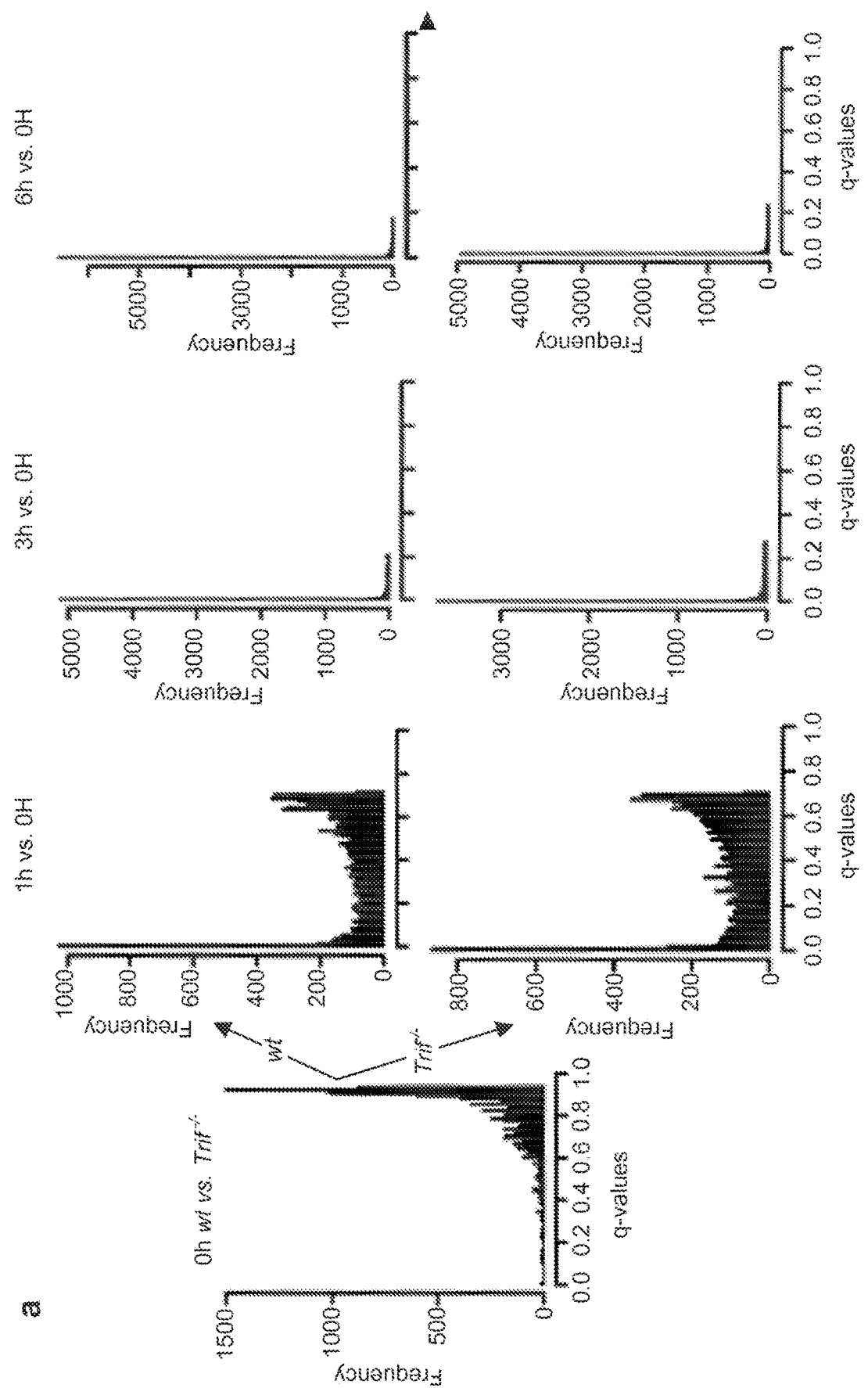
FIG. 15. Genome-wide transcriptional profile of wt and Trif$^{-/-}$ BMM at various time points after phagocytosis of viable avirulent $E.$ $coli$. BMM derived from wt or Trif$^{-/-}$ mice were incubated with viable ThyA⁻ $E.$ $coli$ at a MOI of 20 for the indicated time points. RNA was extracted and subjected to transcriptional analysis by Affymetrix gene microarray. The results of three independent experiments are shown. (a) IBMT q-value distribution comparing gene expression in wt and Trif$^{-/-}$ BMM at steady state (far left '0 h wt vs. Trif$^{-/-}$') and for wt and Trif$^{-/-}$ BMM individually at 1, 3 and 6 hours after phagocytosis of ThyA⁻ $E.$ $coli$. These results illustrate that there are no major differences in gene expression of wt and Trif$^{-/-}$ BMM at steady state, and that both wt and Trif$^{-/-}$ BMM rapidly induce a strong transcriptional response after uptake of $E.$ $coli$ as evidenced by a shift to low q-values in both genotypes. (b) Transcriptional profile of 9922 genes is shown in a heat map.
Figure 15:
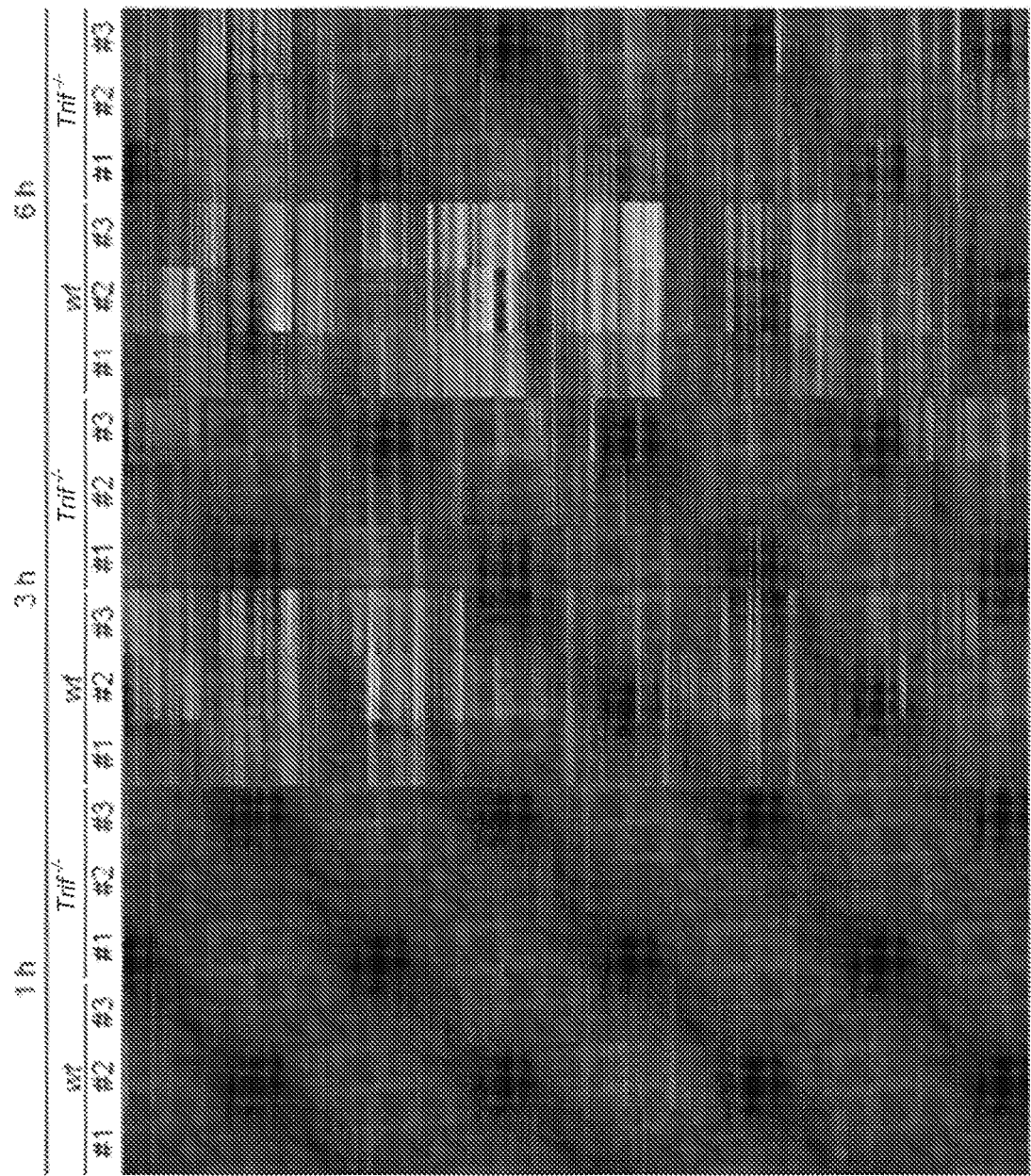
Figure 16:
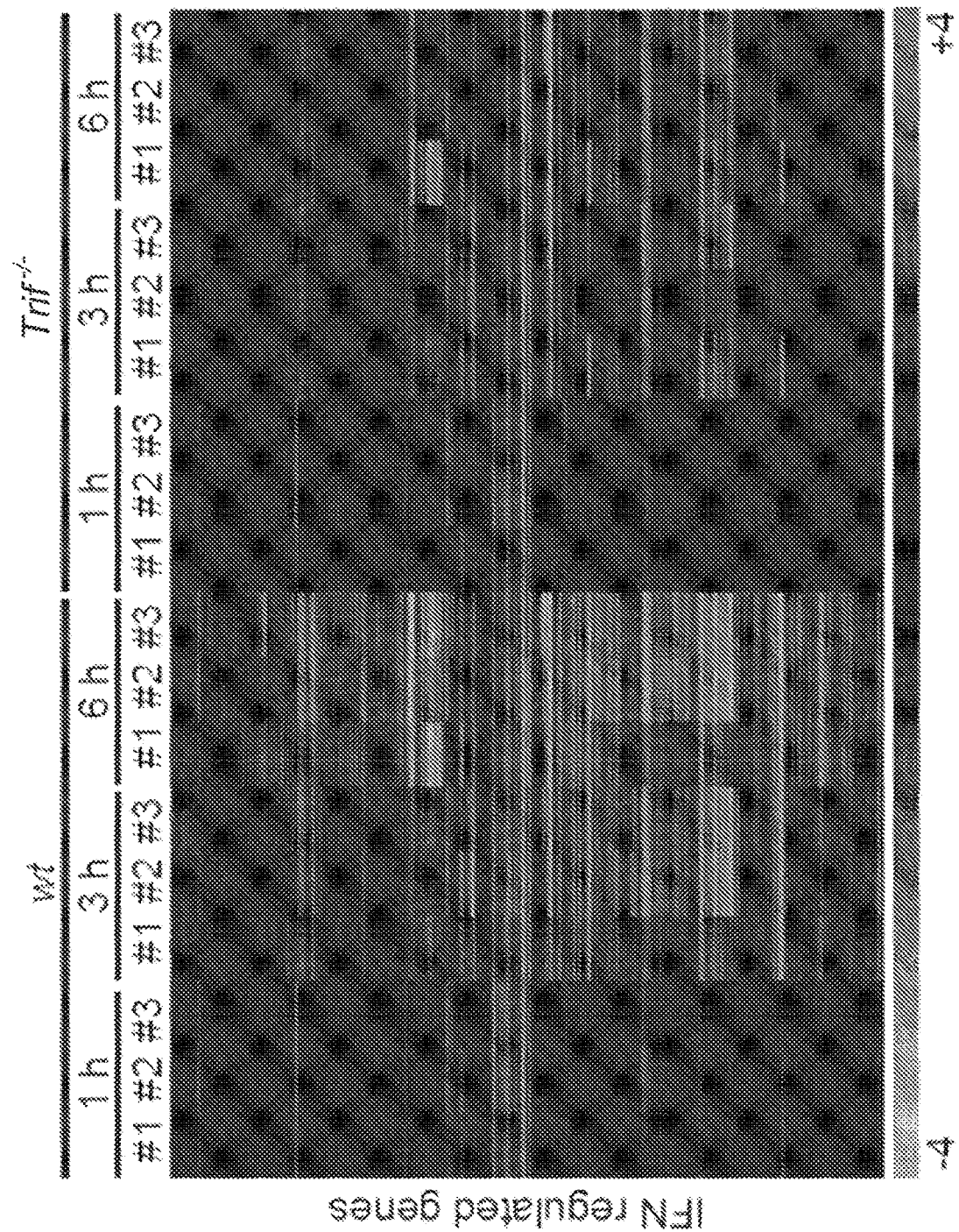
FIG. 16. Expression of IFN-regulated genes and Rel/NF-κB target genes in wt and Trif$^{-/-}$ BMM at various time points after phagocytosis of viable avirulent $E.$ $coli$. BMM derived from wt or Trif$^{-/-}$ mice were incubated with viable ThyA⁻ $E.$ $coli$ at a MOI of 20 for the indicated time points. RNA was extracted and subjected to transcriptional analysis by Affymetrix gene microarray. The results of three independent experiments numbered 1, 2 and 3 are shown. Heat maps of (a) IFN-regulated genes and (b) Rel/NF-κB target genes.
Figure 16:
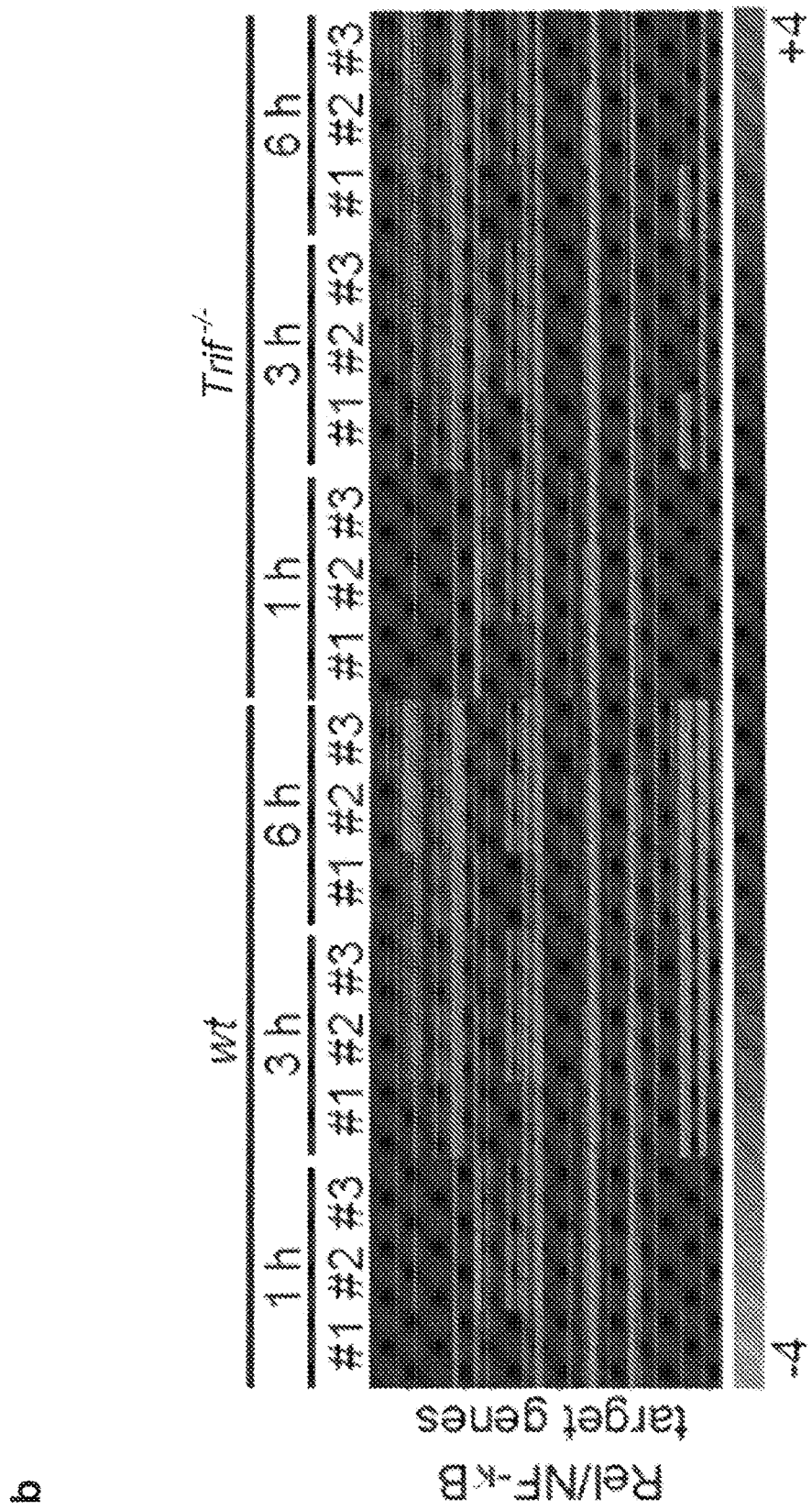
Figure 17:
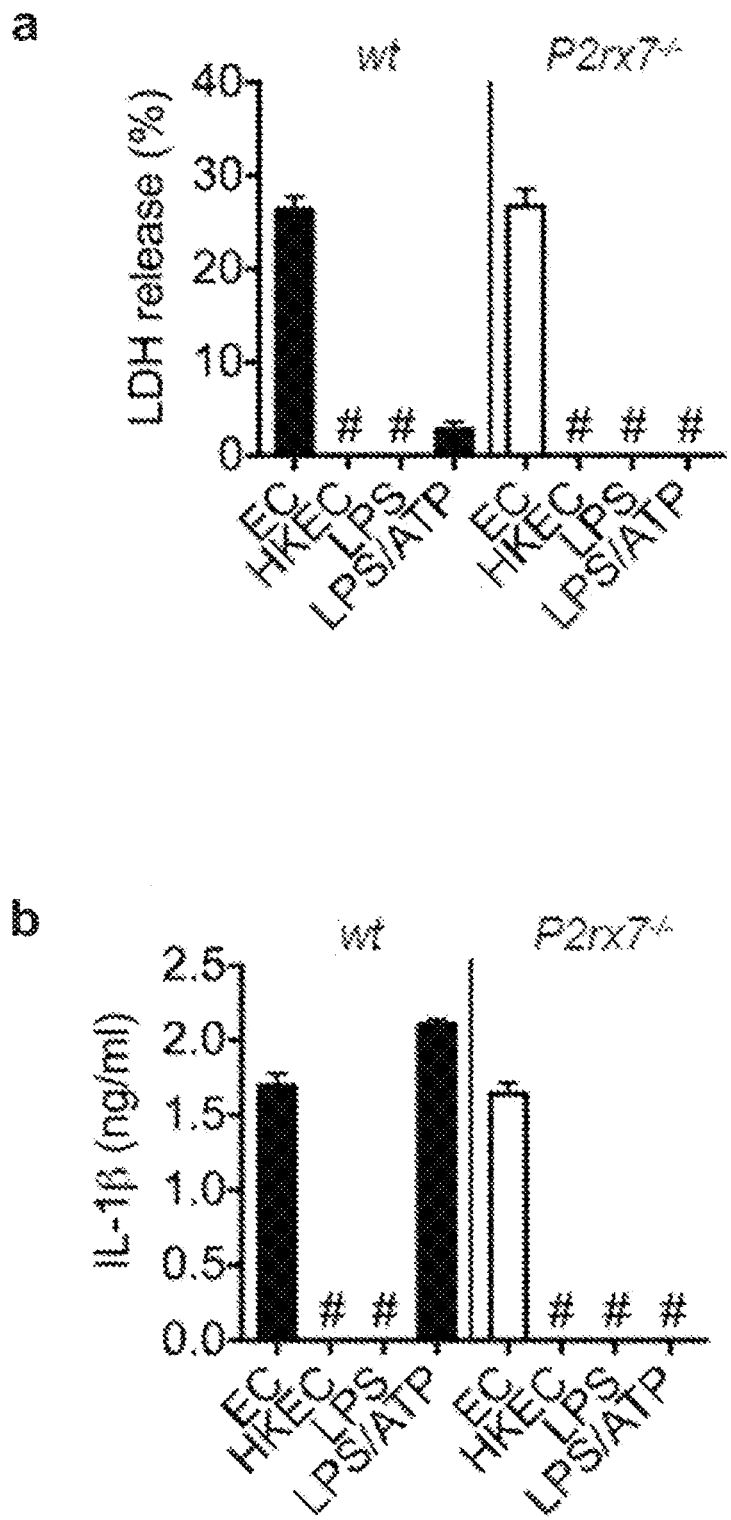
FIG. 17. Pyroptosis and IL-1β production induced by viable avirulent $E.$ $coli$ is independent of activation of the P2X7R, and TRIF is dispensable for ROS production. BMM derived from wt or P2rx7$^{-/-}$ mice were incubated with the indicated stimuli for 24 hours and pyroptosis (a) and IL-1β production (b) were measured. While viable ThyA$^-$ E. coli induce significant release of LDH and IL-1β in wt and P2rx7$^{-/-}$ cells, LPS+ATP-induced pyroptosis and IL-10 production are abrogated in P2rx7$^{-/-}$ BMM. (c) BMM derived from wt or Trif$^{-/-}$ mice were pulsed with the cell permeable ROS indicator H2DCFDA, washed and then incubated with the indicated stimuli for 1 hour and washed again. ROS production was measured by flow cytometry. #; 'not detected'.
Figure 17:
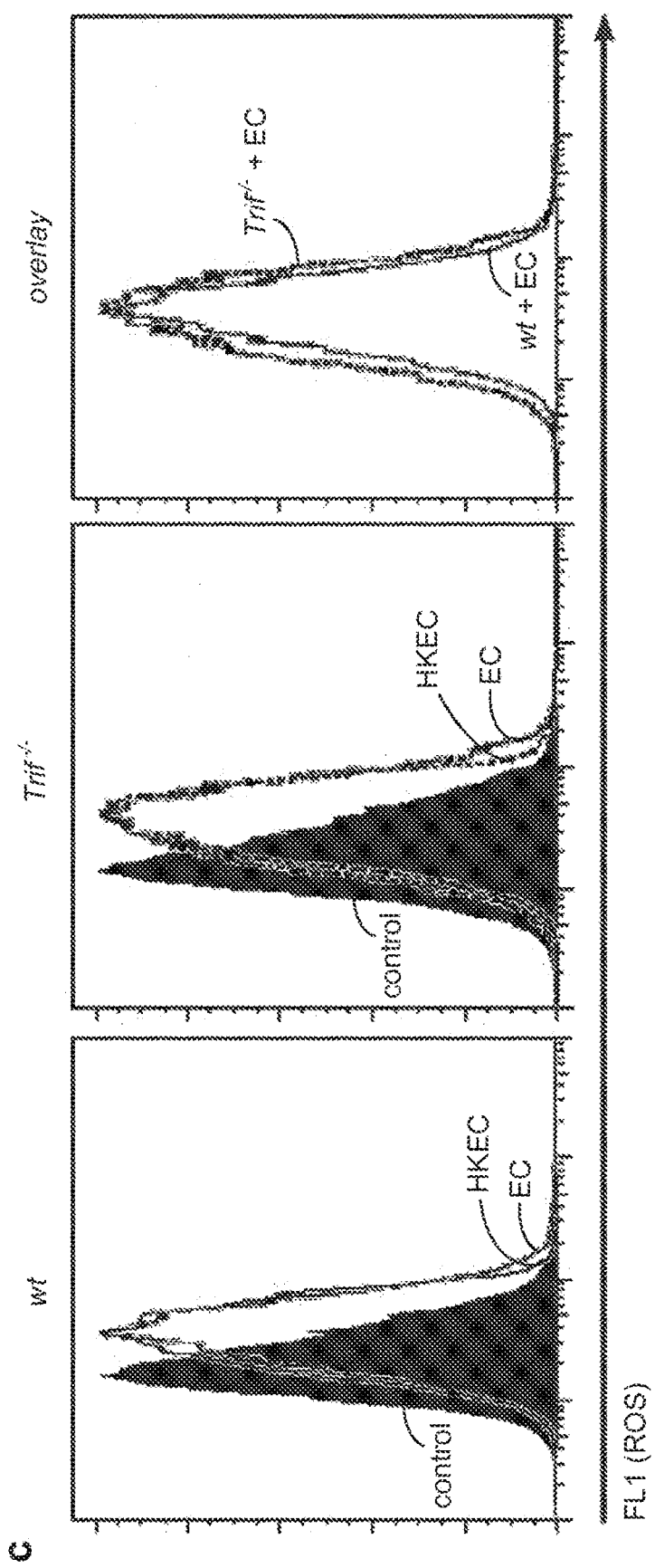

Genome-wide transcriptional analysis of wild type and Trif$^{-/-}$ macrophages before and after phagocytosis of viable ECThyA$^-$ showed differential regulation of several clusters of genes (FIG. 15) including IFN-regulated genes, as expected (Takeuchi et al., *Cell* 140: 805-820 (2010)) (FIGS. 2*a* and 2*b*; FIG. 16*a*), while most of Rel/NF-κB target genes were comparable (FIG. 16*b*). Nlrp3 expression was induced independently of TRIF (FIGS. 2*g* and 2*h*) and negative regulators of inflammasome activity such as those encoded by *Mediterranean fever* (Mefv), Nlrp10 and Casp12 genes were also unchanged or expressed at higher levels in wild type macrophages (FIG. 2*g*), possibly due to negative feedback. Thus, the role of TRIF in inflammasome activation upon phagocytosis of viable ECThyA$^-$ is not explained by transcriptional control of inflammasome components (so called priming (Schroder et al., *Cell* 140: 821-832 (2010)). Furthermore, ATP and reactive oxygen species (ROS) (Schroder et al., *Cell* 140: 821-832 (2010); Zhou et al., *Nature* 469: 221-225 (2011)), known activators of the NLRP3 inflammasome, were not involved, as deficiency for $P_2X_7R$, required for ATP-mediated NLRP3 activation, did not affect pyroptosis or IL-1β production (FIGS. 17*a* and 17*b*), and ROS accumulated equally in response to viable and HK ECThyA$^-$ independently of TRIF (FIG. 17*c*).

Figure 18:
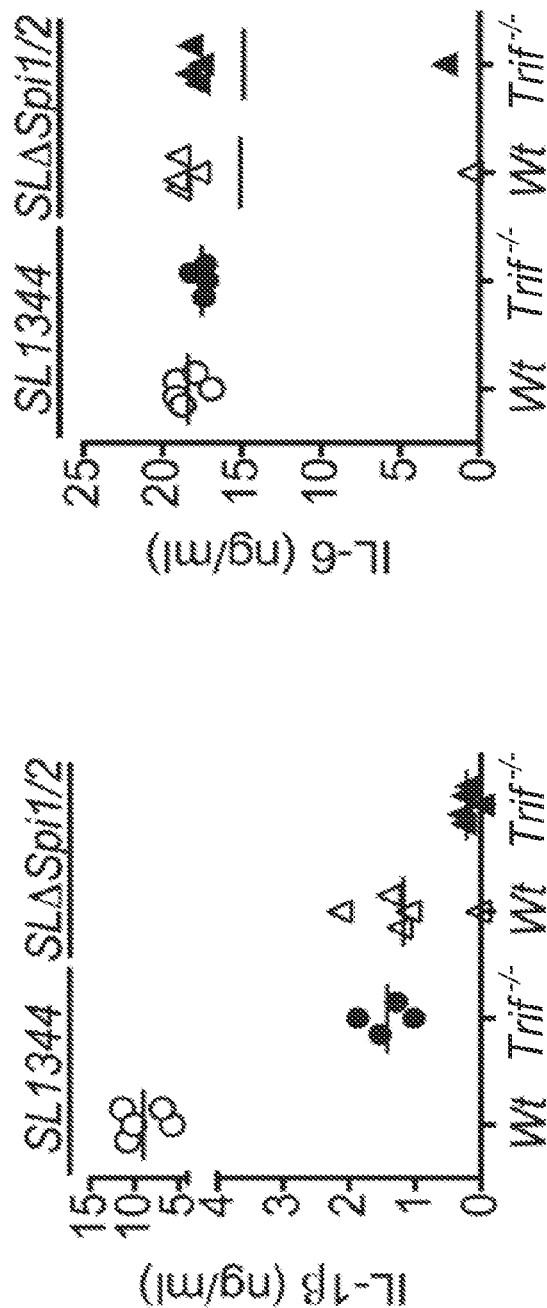
FIG. 18. TRIF deficiency strongly reduces IL-1β production in response to wt and attenuated Salmonella enterica serovar Typhimurium in vivo. Wt and Trif$^{-/-}$ mice were infected with 5×10$^8$ cfu wt (SL1344) or mutant Salmonella enterica serovar Typhimurium lacking Salmonella pathogenicity island (SPI) 1 and 2 (SLΔSpi1/2) by intraperitoneal injection. Serum levels of IL-10 and IL-6 after 6 hours were determined by ELISA.

Injection of viable and HK ECThyA$^-$ into mice induced similarly high serum levels of IL-6 (FIG. 2*i*). In contrast, circulating IL-1β was detected only in mice infected with viable bacteria (FIG. 2*i*), while IFN-β levels were undetectable in all groups (not shown). Confirming our results in vitro, production of IL-1β (but not IL-6) in vivo also required TRIF, ASC, and NLRP3 (FIG. 2*i*). Injection of non-pathogenic *S. typhimurium* induced serum IL-1β levels comparable to those elicited by ECThyA$^-$, which similarly depended on TRIF (FIG. 18). Although pathogenic *S. typhimurium* elicited higher levels of serum IL-1β than non-pathogenic *Salmonella*, this response was also severely reduced in Trif$^{-/-}$ mice, suggesting a previously unappreciated role for TRIF in *Salmonella* infection (FIG. 18). Importantly, deficiency in TRIF, ASC and NLRP3 impaired bacterial clearance during systemic infection with replication sufficient non-pathogenic *E. coli* (FIG. 2*j*). This failure was more dramatic in Trif$^{-/-}$ than in Asc$^{-/-}$ or Nlrp3$^{-/-}$ mice, possibly due to the central upstream role of TRIF in inflammasome activation and IFN-β production.

Figure 19:
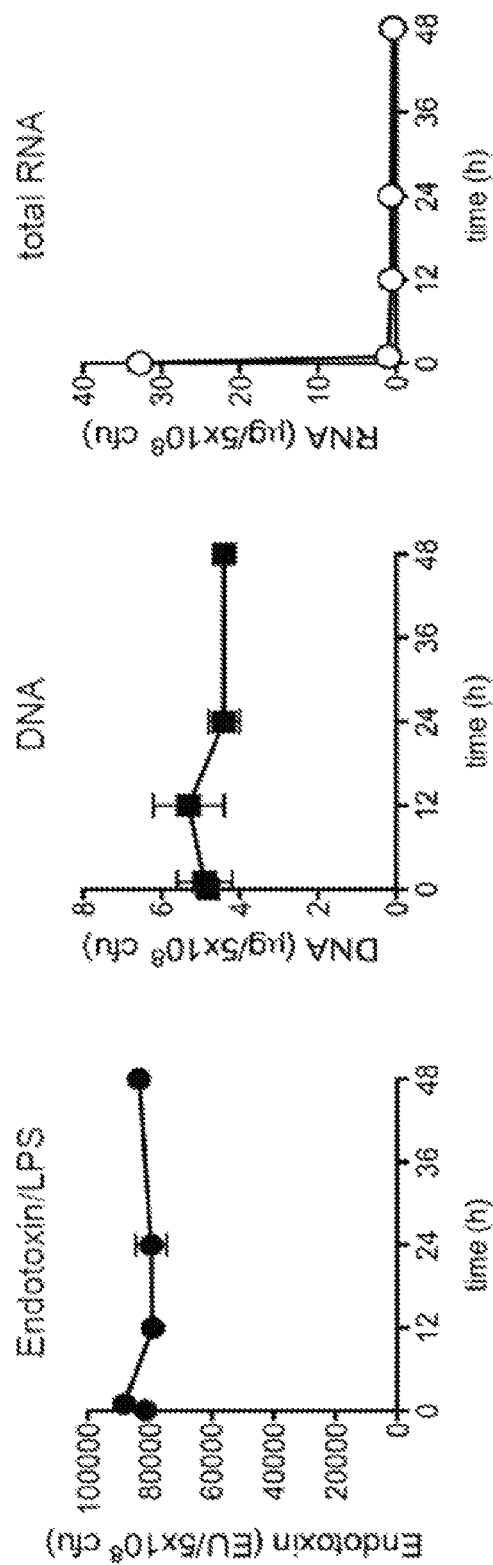
FIG. 19. Absolute quantifications of PAMP contents of viable and killed E. coli. ThyA E. coli were grown to log phase and either left untreated or subjected to heat killing. Heat killed ThyA$^-$ E. coli were stored at 4° C. for the times indicated and endotoxin/LPS, DNA and total RNA contents were measured. Endotoxin/LPS content was measured by Limulus Amebocyte Lysate (LAL) assay, DNA was extracted (DNeasy kit, Qiagen) and quantified using the optical density measured at 280/260 nm, RNA was extracted (e.z.n.a. Bacterial RNA Kit (Omega Bio-Tek)) quantified using the optical density measured at 280/260 nm.
Figure 20:
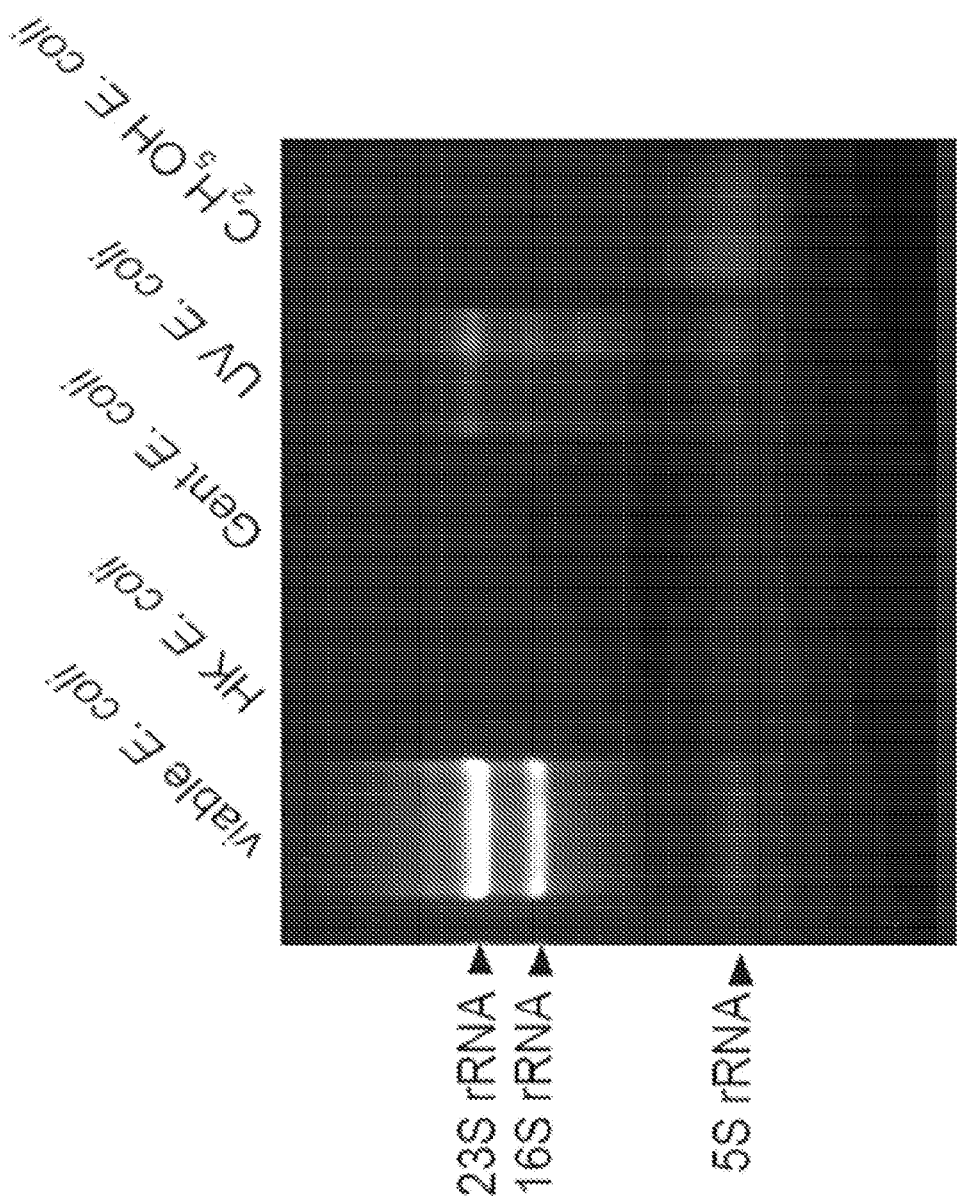
FIG. 20. Total RNA contents of viable and killed E. coli. ThyA$^-$ E. coli were grown to log phase and either left untreated or subjected to killing by the indicated method (HK; heat killing at 60° C. for 60 minutes, Gent; Gentamicin sulfate treatment for 12 hours, UV; UV irradiation for 10 minutes, C$_2$H$_5$OH; 70% Ethanol treatment for 10 minutes followed by washing). Total RNA was extracted from 5×10$^8$ bacteria in each case and visualized by 10% agarose gel electrophoresis.
Figure 21:
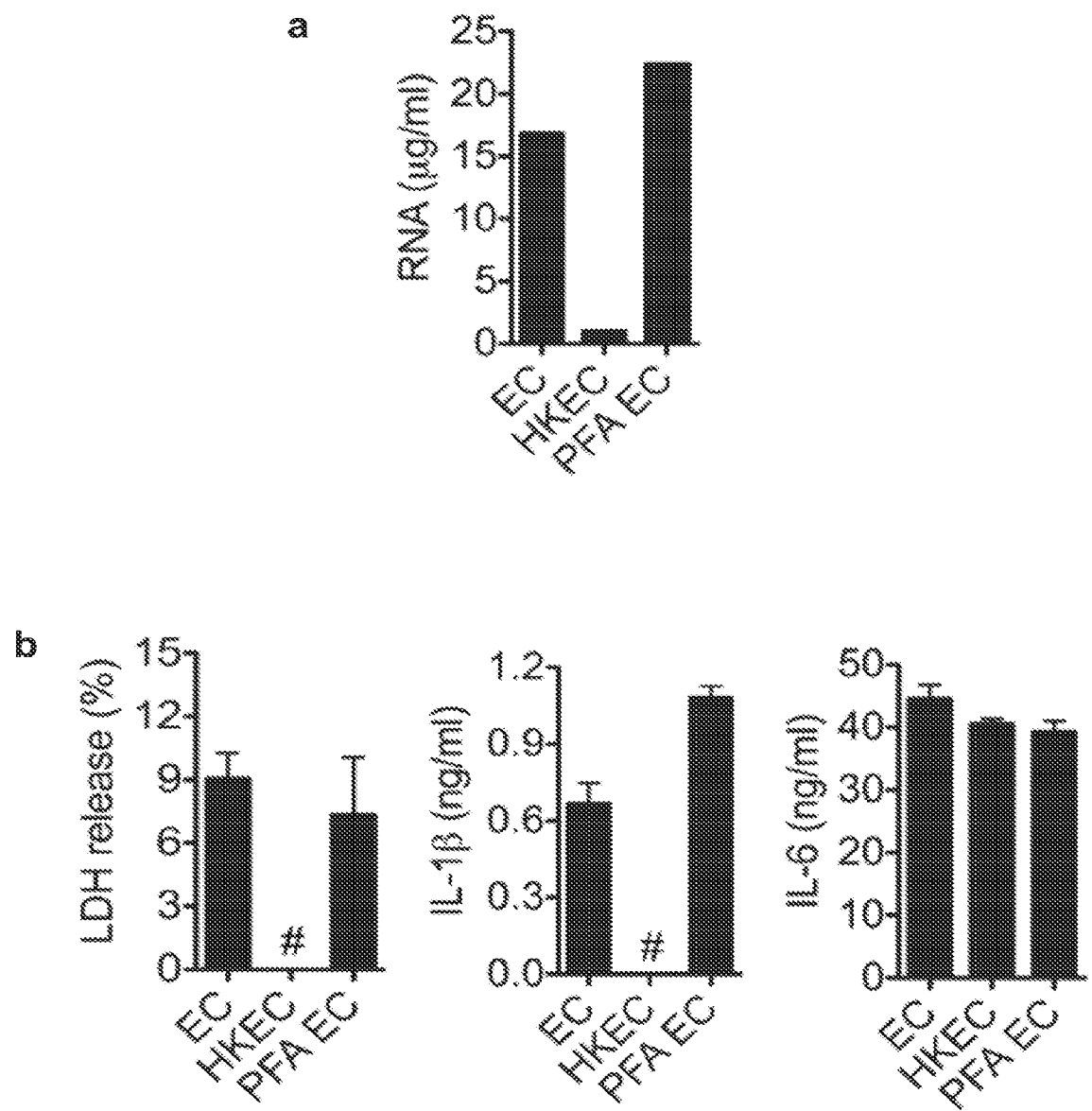
FIG. 21. Paraformaldehyde fixation preserves the bacterial RNA content and restores cellular responses. (a) ThyA$^-$ E. coli were grown to log phase and either left untreated or subjected to heat killing (HK) or paraformaldehyde (PFA) fixation. Total RNA yield extracted from 5×10$^8$ bacteria respectively was measured. (b) BMM were stimulated with viable, HK or PFA fixed ThyA$^-$ E. coli for 24 hours. LDH (left) and IL-1β (middle) and IL-6 (right) release were measured in the supernatants. #; 'not detected'.

The ability to sense microbial viability through pathways downstream of pattern recognition receptors suggests the existence of vita-PAMPs; PAMPs associated with viable but not dead bacteria. In contrast to LPS and genomic DNA that remained constant after killing ECThyA$^-$ with heat, total bacterial RNA was rapidly lost (FIGS. 3*a* and 3*b*; FIG. 19). Total RNA content was also lost with antibiotic treatment, and little ribosomal RNA (rRNA) remained after killing with UV and ethanol (FIG. 20). Only fixation with paraformaldehyde (PFA) efficiently killed the bacteria (not shown), but preserved total RNA content (FIG. 21*a*). Remarkably, unlike bacteria killed by other means, PFA-killed bacteria induced pyroptosis and IL-1β to levels similar to those induced by viable bacteria (FIG. 21*b*). Thus, the presence or absence of RNA correlated with the ability to activate pathways involved in sensing viability.

Figure 3:
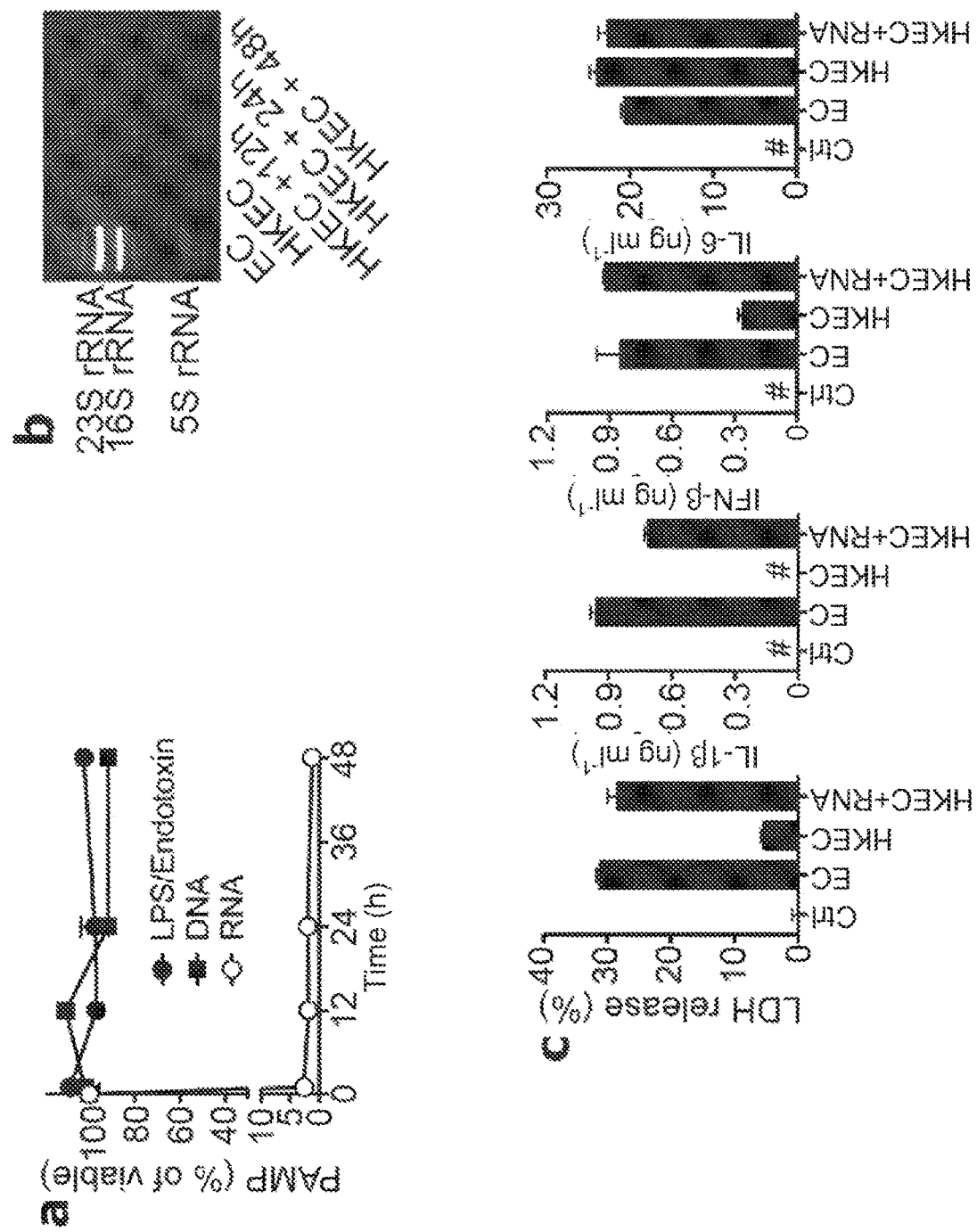
FIG. 3. Bacterial RNA is a vita-PAMP that accesses cytosolic receptors during phagocytosis, and in the absence of virulence factors. a. LPS/Endotoxin, genomic DNA and total RNA in EC before and at indicated times after heat killing. b. Agarose gel electrophoresis of EC total RNA before and after heat killing at 60° C. for 60 min followed by 4° C. incubation for indicated times. c,d. LDH, IL-1β, IFN-β and IL-6 at 24 h in response to viable and HKEC, or HKEC with 10 μg/ml total EC RNA (HKEC+RNA). # in c,d, 'Not detected'. (a)-(d), data by BMM and represent ≥5 experiments. (e) Representative ratiometric epifluorescence imaging of BMM at 8 h with Fdx alone (ctr 8 h), Fdx and viable EC (EC 8 h) or gentamicin-killed EC (Gent EC) (colour code indicates pH scale). Positive control: Ground silica (silica 1 h). (f) Quantification of cytosolic Fdx (% of total Fdx/cell). Each dot represents % released Fdx/individual cell. Grey bars represent mean Fdx release. *; p≤0.05, ; p≤0.01, *; p≤0.001. All bars represent mean s.e.m.
Figure 3:
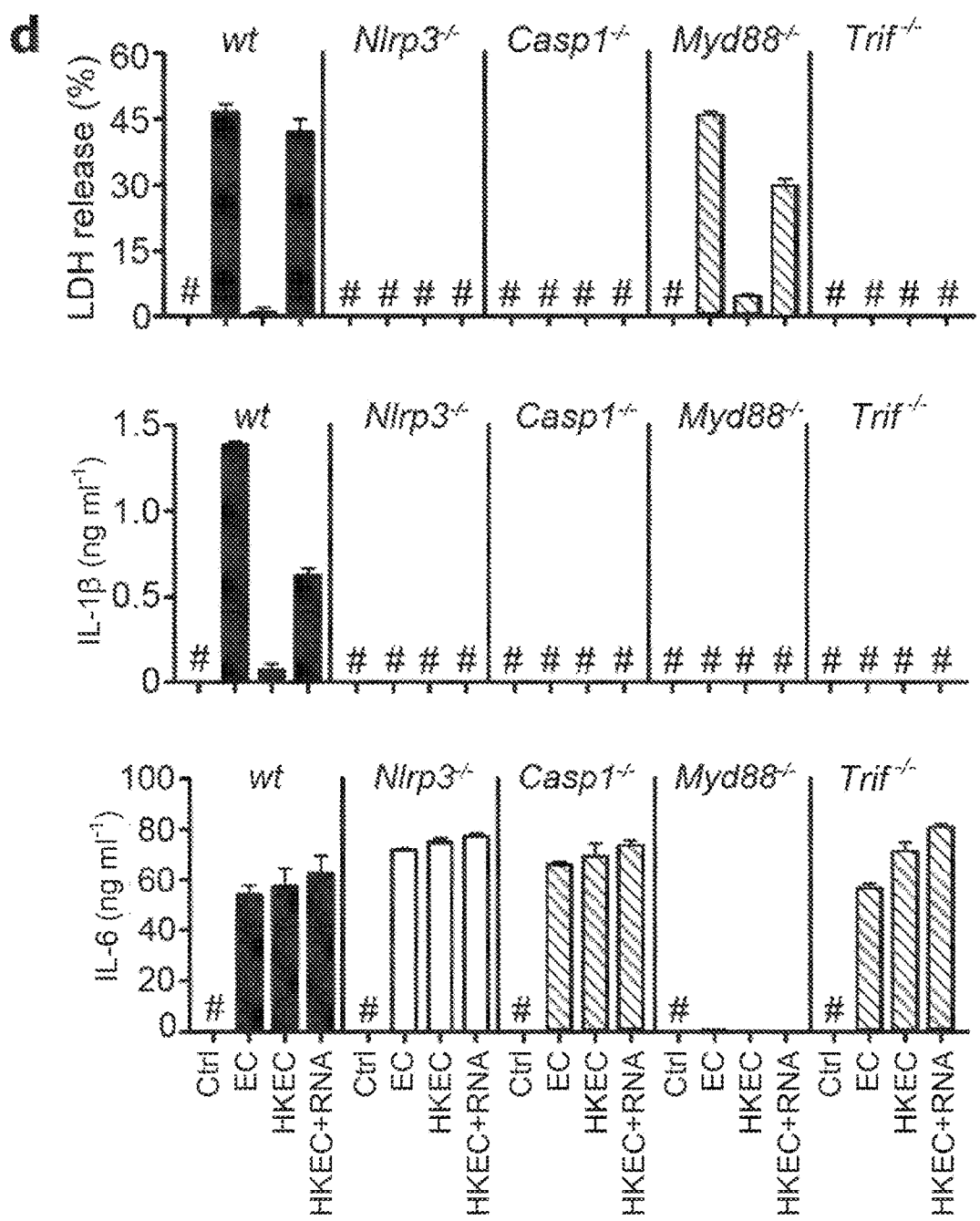
Figure 3:
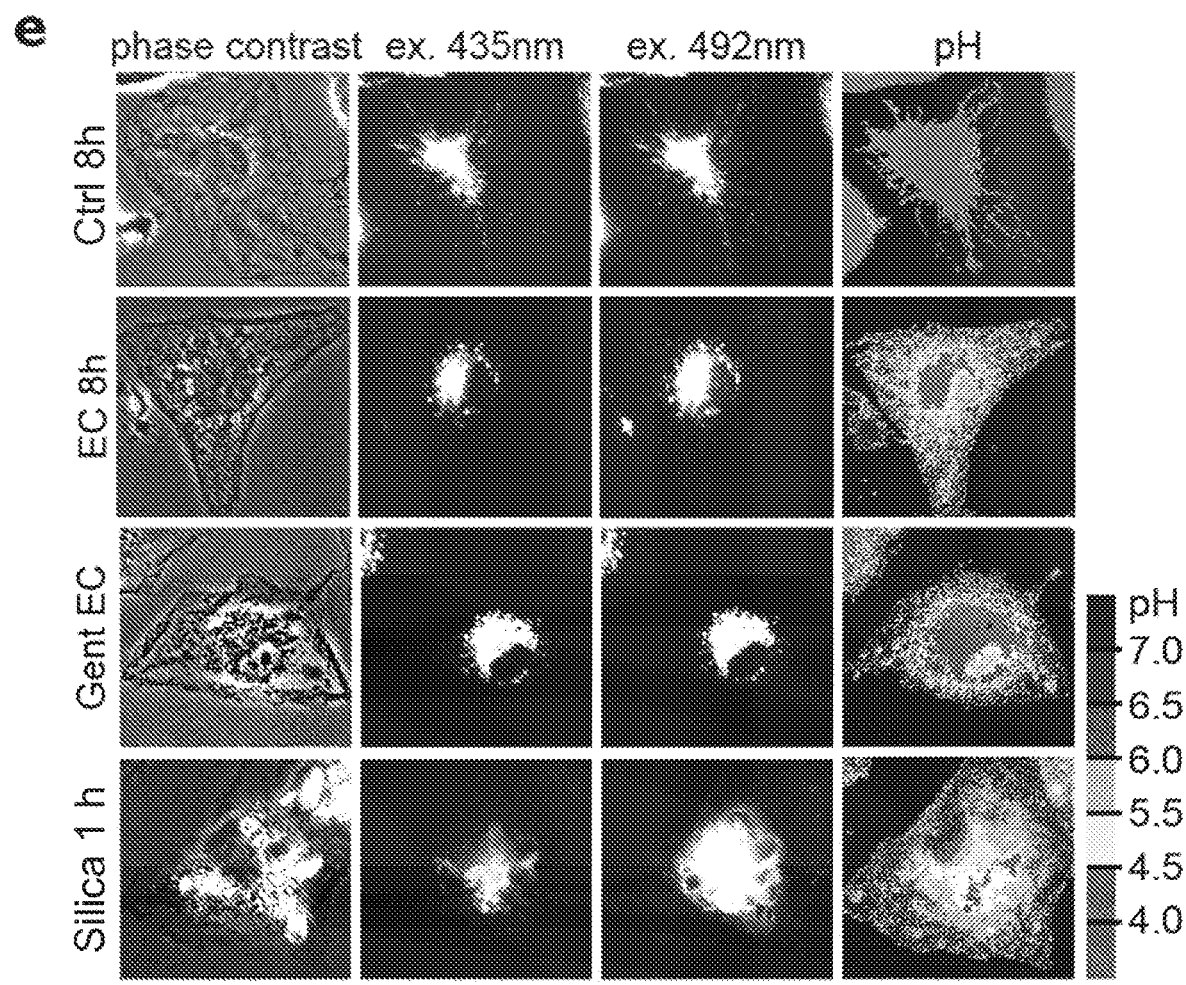
Figure 3:
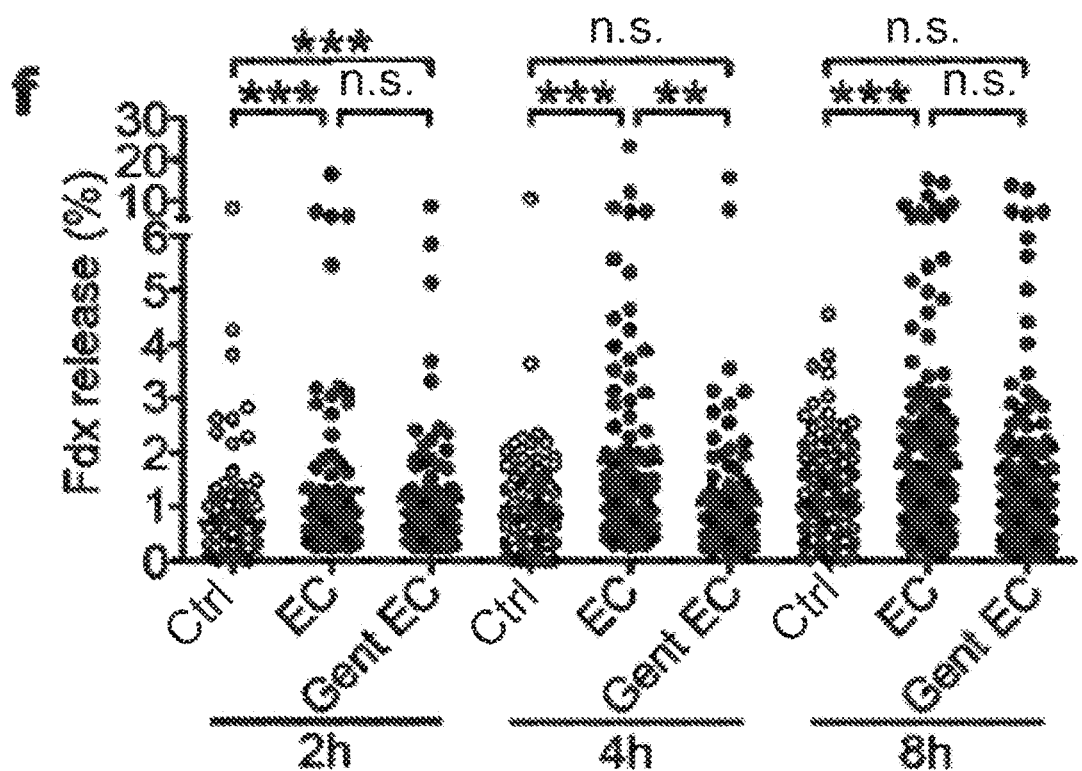
Figure 22:
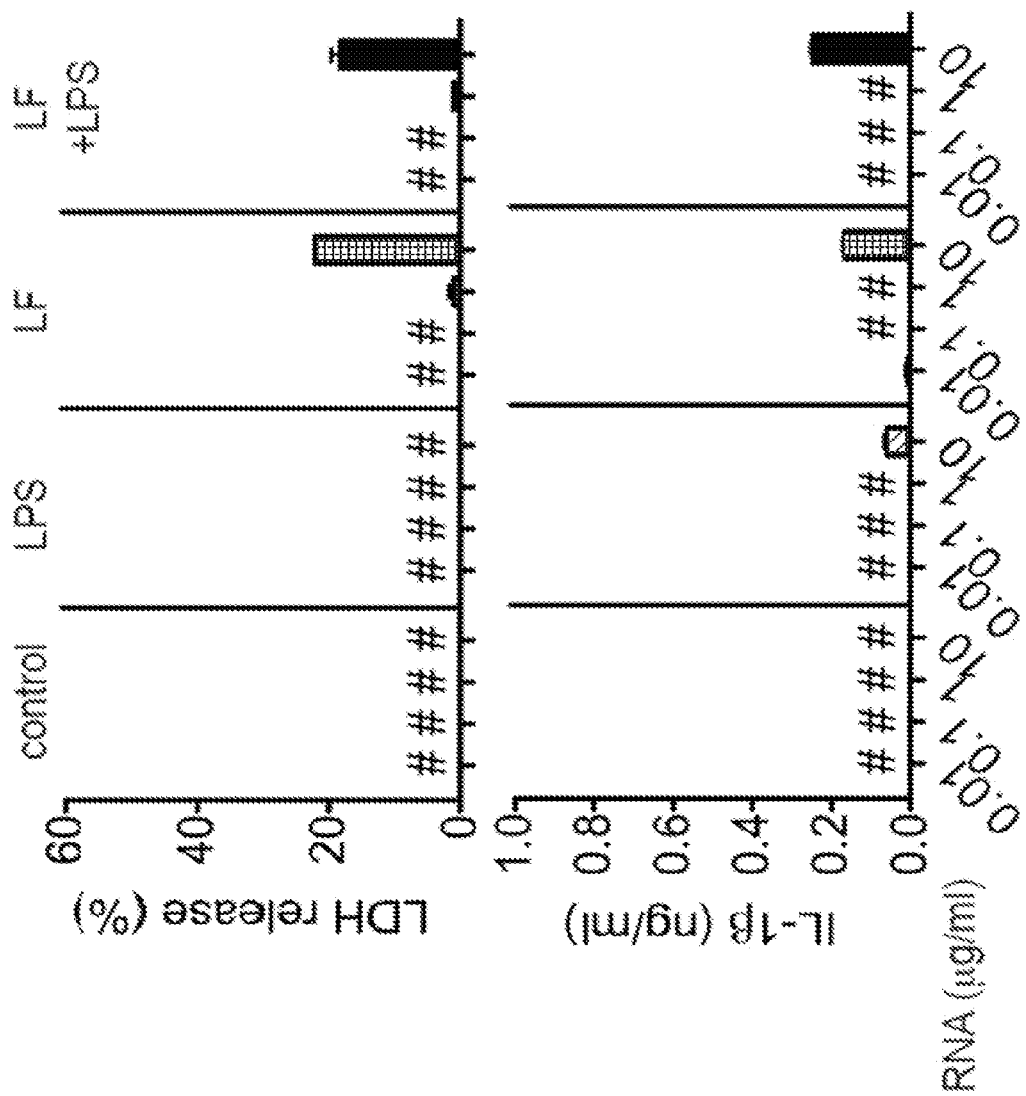
FIG. 22). Class-specific anti-*E. coli* antibody serum titers at 25 days. *; p≤0.05, ; p≤0.01, *; p≤0.001. All bars represent mean±s.e.m.

These results suggest that prokaryotic RNA represents a labile PAMP closely associated with bacterial viability, which might signify microbial life to the immune system. Indeed, addition of purified total bacterial RNA fully restored the ability of HK ECThyA$^-$ to induce pyroptosis, IL-1β and IFN-β production (FIG. 3*c*). These responses were dependent on TRIF, NLRP3 and caspase-1, just as those elicited by viable bacteria (FIG. 3*d* compared to FIGS. 1*j* and 2*a-f*). The NLRP3 inflammasome mediates recognition of viral RNA during Influenza A infection (Pang et al., *Trends Immunol* 32: 34-41 (2011)). Our results suggest a more general role for NLRP3 in responses to RNAs of microbial origin. RNA can activate the NLRP3 inflammasome when delivered into the cytosol (where NLRP3 resides) with transfection reagents (Kanneganti et al., *Nature* 440: 233-236 (2006)). In contrast, inflammasome activation by the combination of total bacterial RNA and dead ECThyA$^-$ did not require RNA transfection (FIGS. 3*c* and 3*d*). Administration of total *E. coli* RNA alone or in combination with LPS (to mimic an *E. coli*-derived PAMP+ RNA) had little effect on NLRP3 inflammasome activation unless the RNA was delivered to the cytosol using Lipofectamine (FIG. 22) or in combination with ATP. Thus, phagocytosis of viable bacteria is a natural context of bacterial RNA-mediated NLRP3 inflammasome activation.

Figure 23:
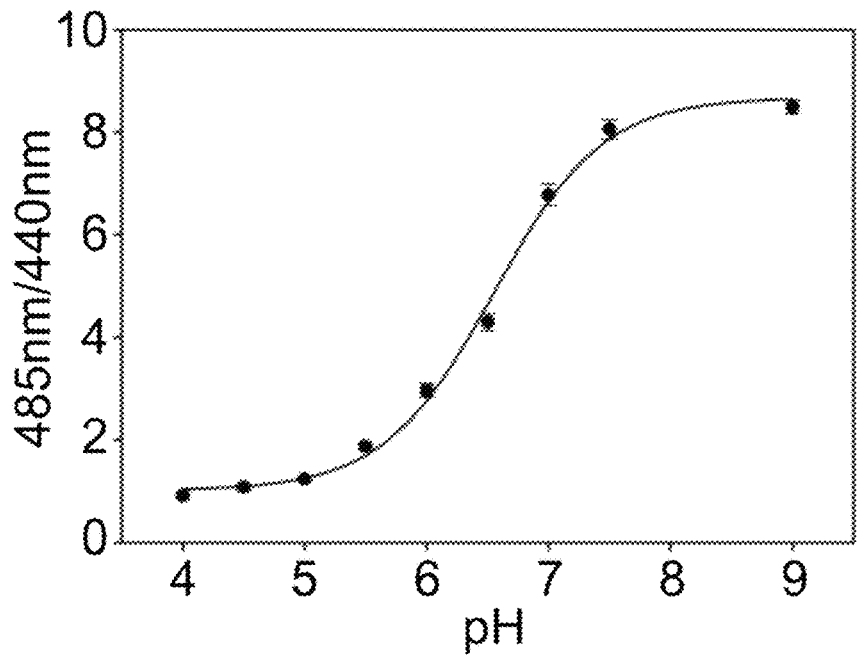
FIG. 23. Phagocytosis of E. coli induces low level leakage of phagolysosomal contents into the cytosol of BMM. (a) Epifluorescence images of fluorescein dextran (Fdx) loaded, permeabilized BMMs were taken at fixed pHs. The ex. 485 nm:ex. 440 ratios were measured and used to generate pH calibration curves (4 parameter sigmoid curve calculated by non-linear regression in sigmaplot). Error bars indicate standard deviations. (b) Mean Fdx released into pH neutral compartments relative to total cellular Fdx content was measured in BMMs at the indicated time points after incubation with either medium (Fdx) or viable (Fdx+EC) or gentamicin killed ThyA$^-$ E. coli (Fdx+Gent EC) and expressed as percent Fdx release. Mean was calculated from data shown in FIG. 3f.
Figure 23:
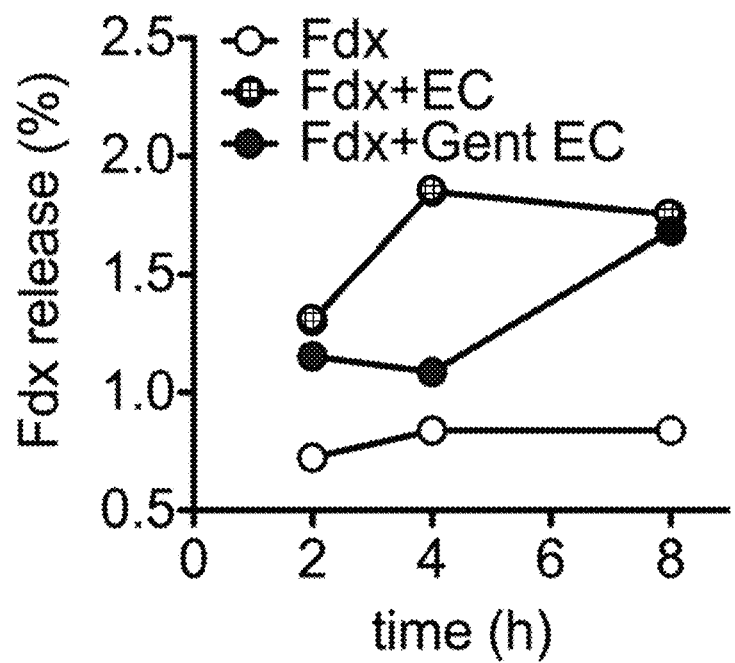

These findings raised the question as to how vita-PAMPs in phagolysosomes gain access to cytosolic receptors such as NLRP3 in the absence of invasion, auxiliary secretion systems or pore forming toxins. To address this question, we exploited the pH sensitive excitation spectrum of fluorescein: the acidic pH in phagolysosomes quenches fluorescence while release into the pH neutral cytosol allows a regain in fluorescence (Davis et al., *J Leukoc Biol:* 88, 813-822 (2010)). Phagocytosis of avirulent ECThyA$^-$ in the presence of fluorescein-conjugated dextran (Fdx), consistently induced low level release of Fdx into the cytosol of macrophages (FIGS. 3*e* and 3*f*; FIG. 23). This indicates that phagosomes carrying *E. coli* exhibit intrinsic leakiness, a property previously described for particles such as beads and crystals that induce phagolysosomal destabilization (Davis et al., *J Leukoc Biol* 88: 813-822 (2010); Hornung et al., *Nat Immunol* 9: 847-856 (2008)). Interestingly, killed *E. coli* also induced Fdx release, although to a slightly lower extent than viable *E. coli* (FIGS. 3*e* and 3*f*), demonstrating that phagosomal leakage occurs independently of bacterial viability. Therefore, RNA from viable bacteria could gain access to cytosolic receptors via intrinsic phagosomal leakage. These results may also explain the reported ability of phagosome-degraded mutants of *Listeria monocytogenes* or *Staphylococcus aureus* to induce a transcriptional response dependent on cytosolic NLRs (Herskovits et al., *PLoS Pathog* 3: e51 (2007); Shimada et al., *Cell Host Microbe* 7: 38-49 (2010)).

Figure 4:
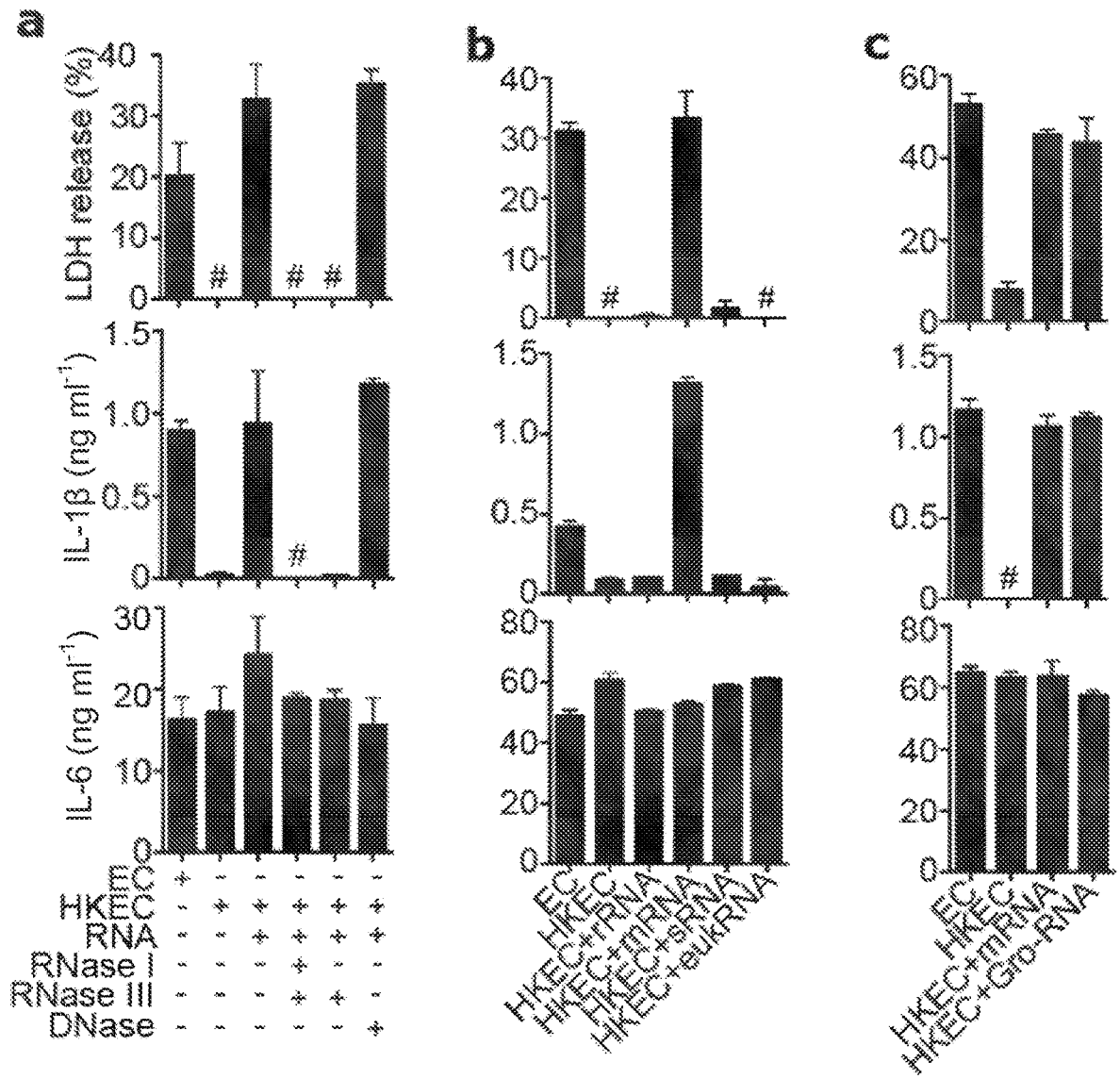
FIG. 4. Bacterial messenger RNA constitutes an active vita-PAMP. (a)-(c) and (e)-(g). LDH, IL-1β and IL-6 at 24 h. (a) Total EC RNA treated with RNAse I and RNAse III, RNAse III alone, or DNAse prior to stimulation of BMDC. (b) BMM treated with viable or HKEC, or HKEC with 0.1 μg/ml of different bacterial RNA; ribosomal (rRNA), messenger (mRNA), small (sRNA) or eukaryotic RNA (eukRNA). (c) BMDC responses. Gro-RNA; in vitro transcribed EC Gro-operon RNA. (d) Predicted secondary structure of Gro-RNA. Colour code indicates base pairing probability. (e) BMM treated with in vitro transcribed Gro-RNA or Gro dsRNA alone or with HKEC. (f) BMDC responses. Era-RNA and DNApol-RNA; in vitro transcribed EC Era-GTPase and DNA-polymerase-III RNA, respectively. (g) BMM treated with different doses of unmodified (control), or modified Gro-RNA with HKEC (5'cap, 5' m$^7$G capping; CIP, calf intestinal phosphatase; 3'poly(A), 3'-polyadenylation). (a)-(g), #, 'not detected', all RNA at 10 μg/ml except as noted, data represent ≥5 experiments. (h) Mice vaccinated and boosted twice with viable EC, HKEC or HKEC with 30 μg total purified bacterial RNA (HKEC+RNA) (vaccination regimen in suppl.
Figure 4:
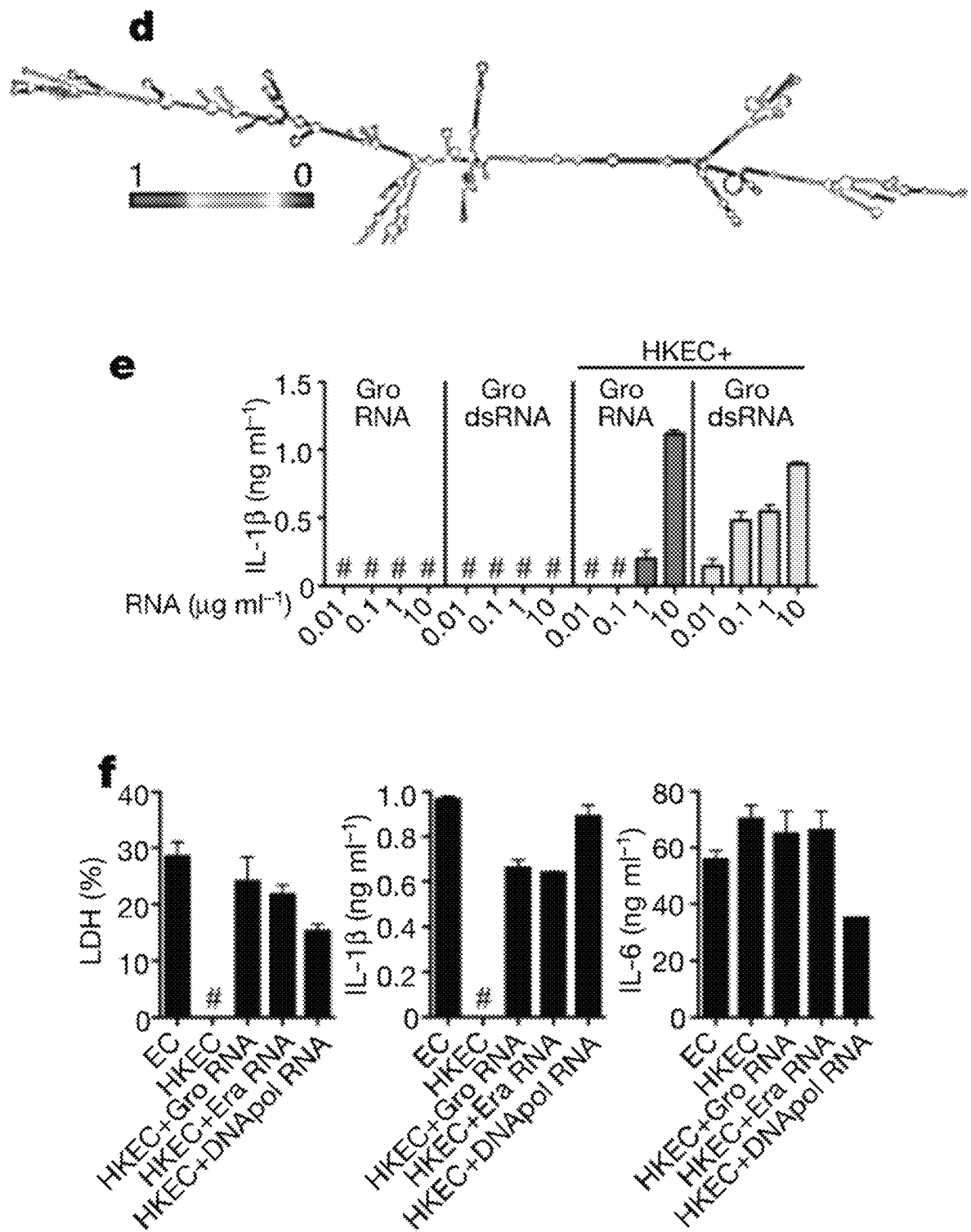
Figure 4:
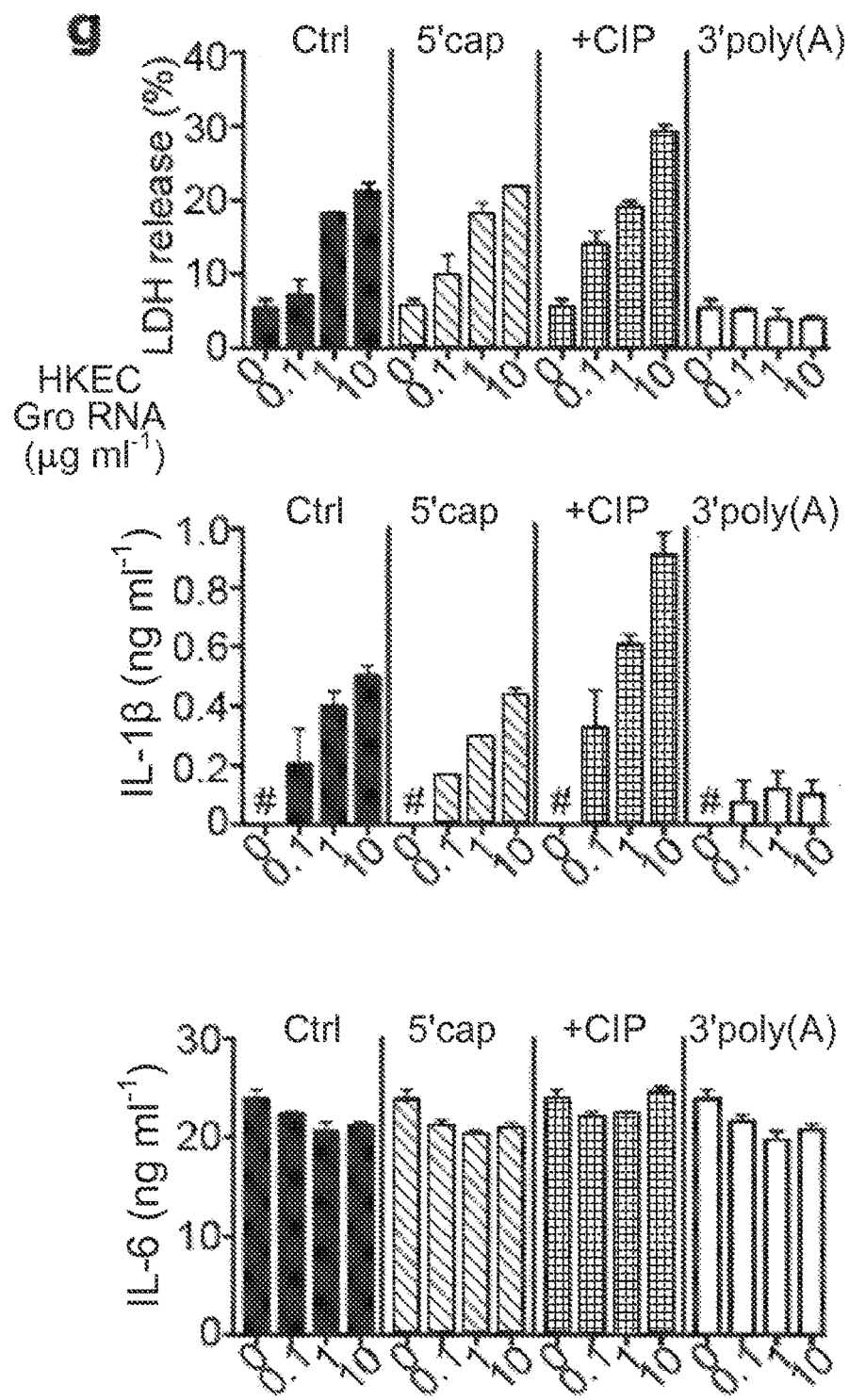
Figure 4:
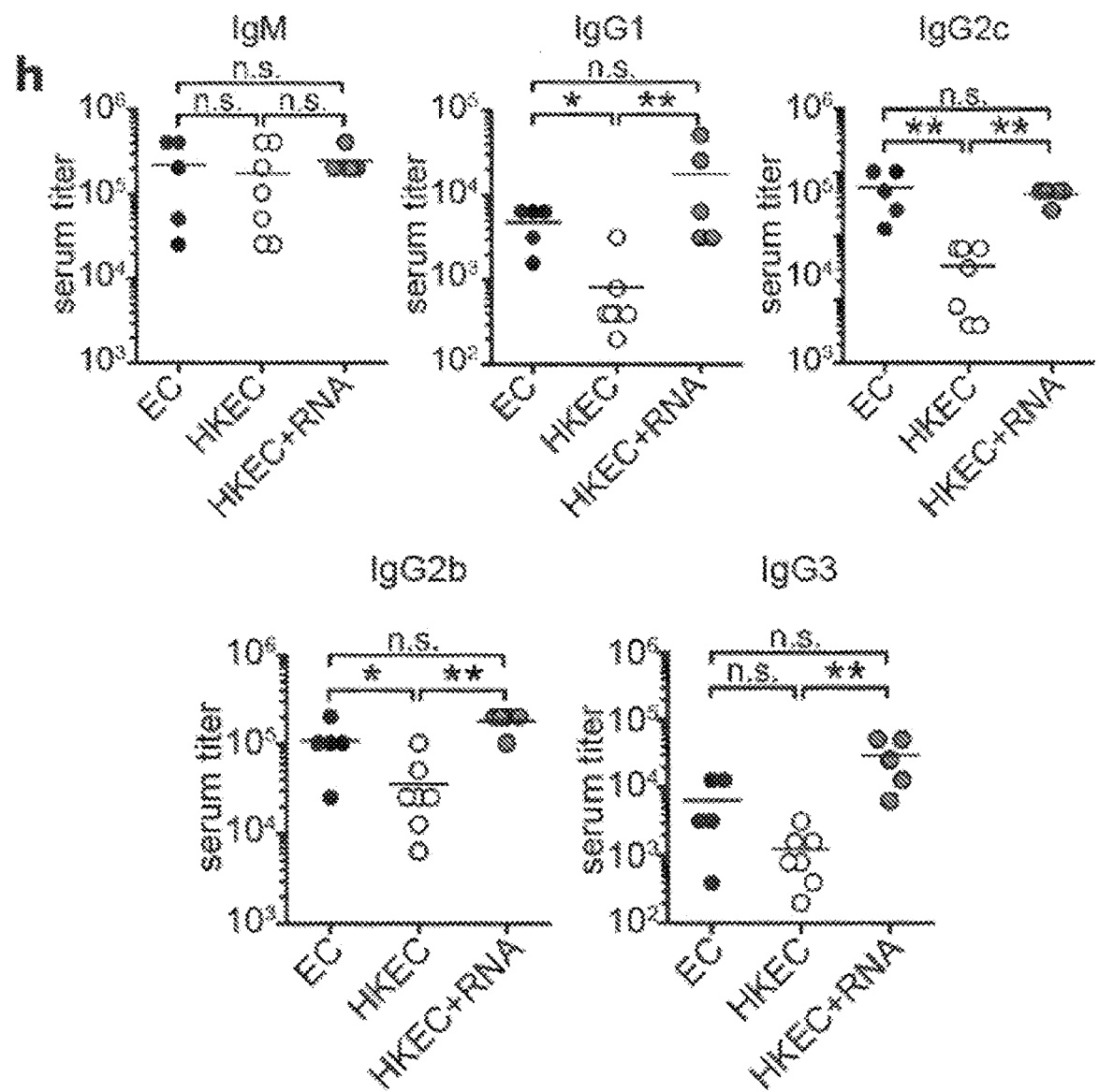
Figure 24:
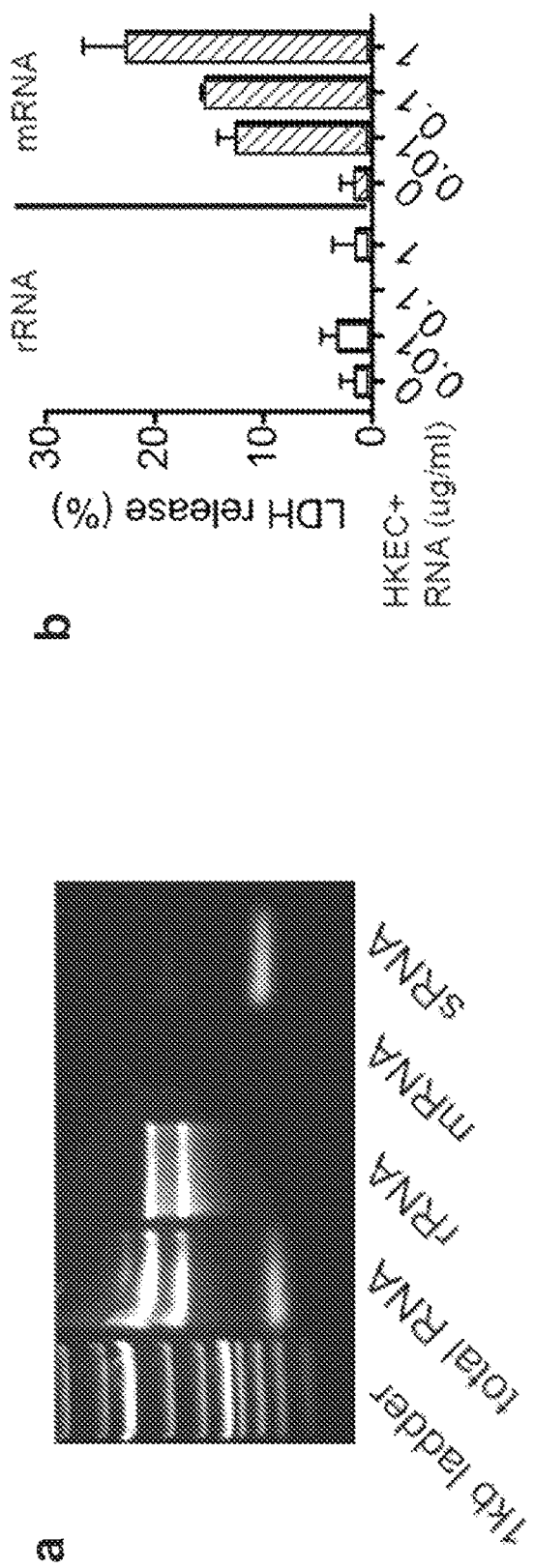
FIG. 24. Messenger RNA (mRNA), but not ribosomal RNA (rRNA), is sufficient to restore inflammasome activation and IFN-β production in response to heat killed E. coli. (a) Total RNA was extracted from ThyA$^-$ E. coli, fractionated into ribosomal rRNA, mRNA, and small RNA (sRNA), and subsequently visualized by 1% agarose gel electrophoresis. (b) BMM were incubated with heat killed (HK) ThyA$^-$ E. coli in combination with the indicated doses of purified E. coli rRNA (left) or mRNA (right). At 24 hours, pyroptosis was measured as LDH release. (c) BMM were incubated with HK ThyA$^-$ E. coli in combination with 0.1 μg/ml of the indicated RNA species isolated from ThyA$^-$ E. coli. At 24 hours, pyroptosis was measured as LDH release and IL-1β, IFN-β and IL-6 production were measured by ELISA. #; 'not detected'.
Figure 24:
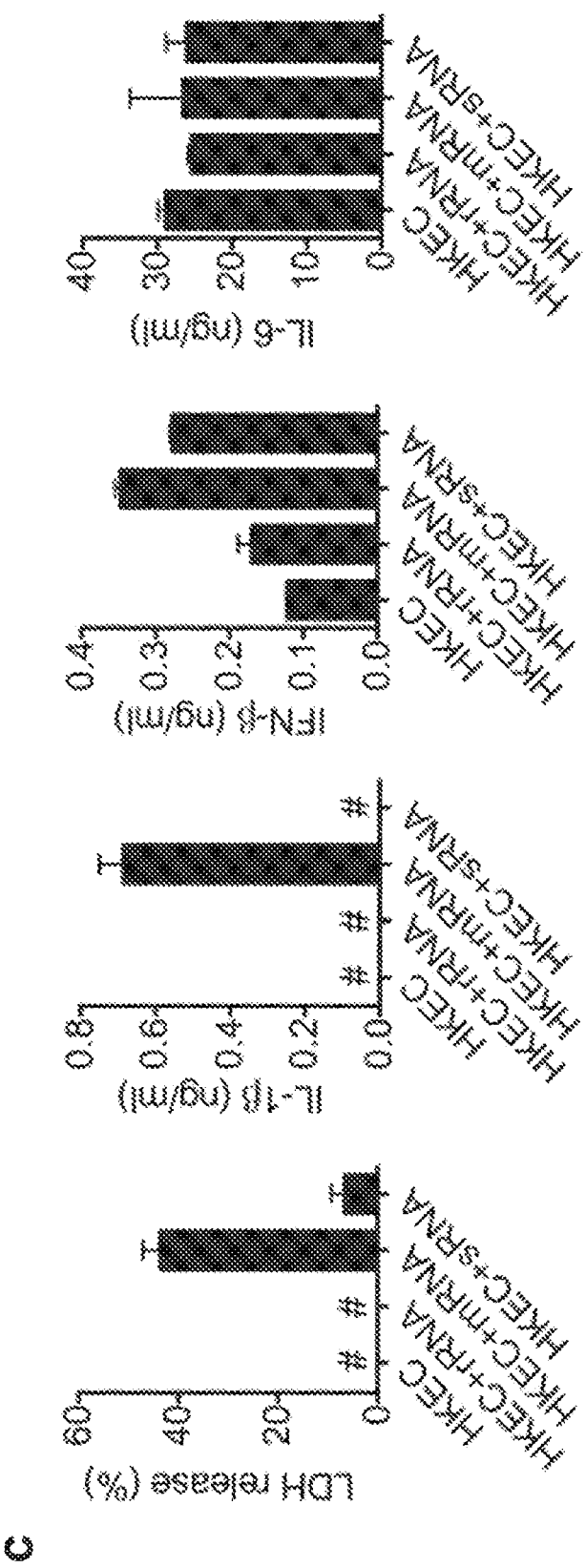

Digestion of total RNA from *E. coli* with exonuclease RNase I and double-stranded RNA (dsRNA)-specific endonuclease RNase III abrogated LDH and IL-1β release, while DNase treatment had no effect (FIG. 4*a*). Of *E. coli* RNA species, mRNA most potently induced pyroptosis as well as production of IL-1β and IFN-β. Small RNA (sRNA) or the most abundant RNA, ribosomal RNA (rRNA), had little or no detectable effects (FIG. 4*b*; FIG. 24). *E. coli* rRNA undergoes extensive modifications not found in mRNA (Piekna-Przybylska et al., *Nucleic Acids Res* 36: D178-183 (2008)), which may underlie the differential activity of these RNA species. The relative amount of mRNA was <1% of the total RNA and accordingly, mRNA was approximately 100-fold more effective than total RNA (FIGS. 3c, 4a and 4b, and 24).

Figure 6:
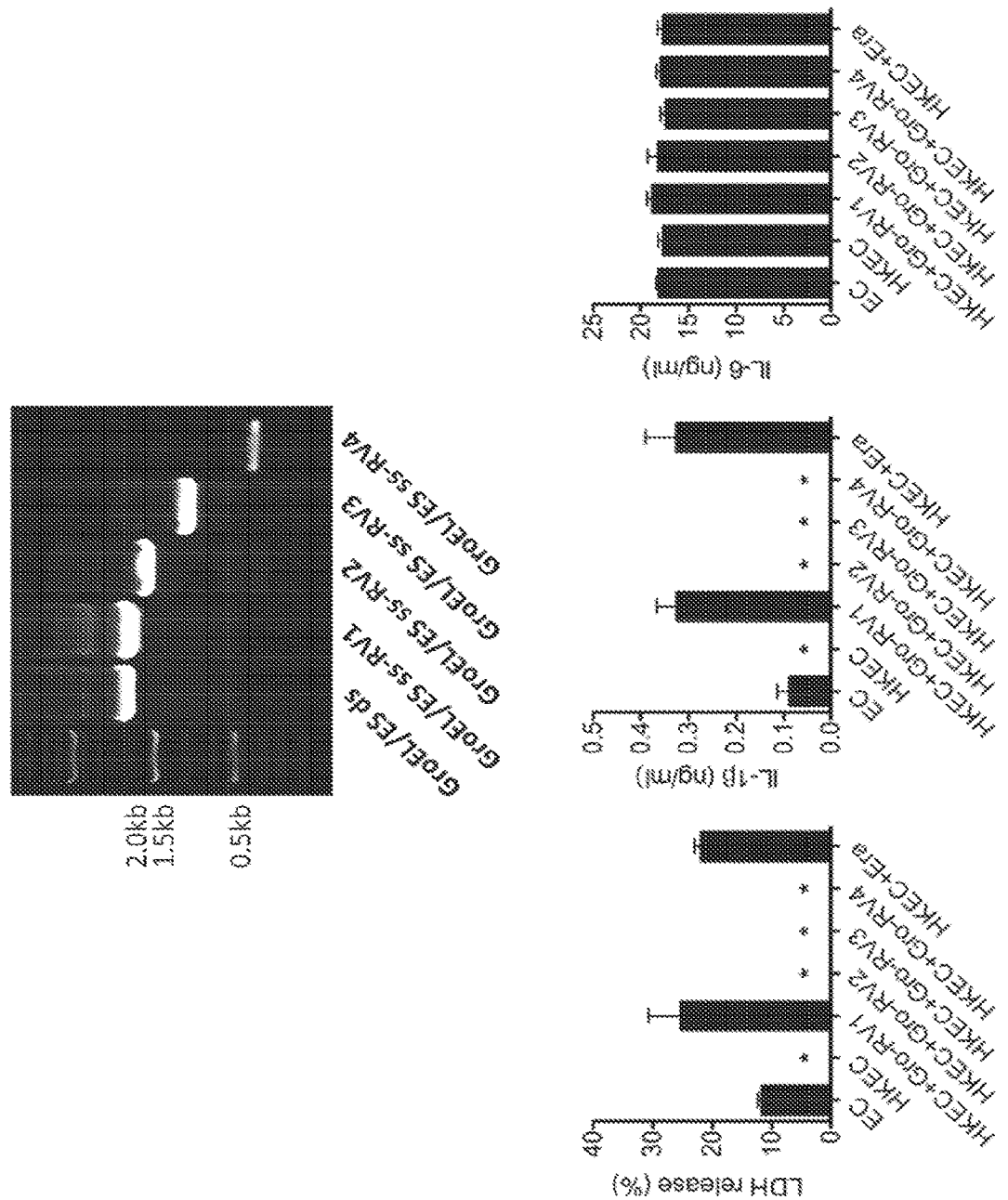
FIG. 6. Shortening of the GroEL/ES in vitro transcribed RNA or loss of the 3'-end structure results in diminished activity of the RNA. The photograph in the top panel shows a portion of the same DNA gel electrophoresis as FIG. 5. BMDC were treated with live $E.$ $coli$ (EC) or heat killed $E.$ $coli$ (HKEC), or HKEC in combination with various in vitro transcribed RNAs. After 24 hours, pyroptotic cell death was measured by LDH-release (LDH, left panel). IL-1β (middle) and IL-6 (right panel) were measured by ELISA. HKEC+in vitro transcribed full length GroEL/ES RNA (GroEL/ES-ss-RV1) induce similar responses as EC, whereas addition of GroEL/ES transcripts that are shortened from the 3'-end (thus lacking the original 3'-stem loop structure) lack this activity.
Figure 25:
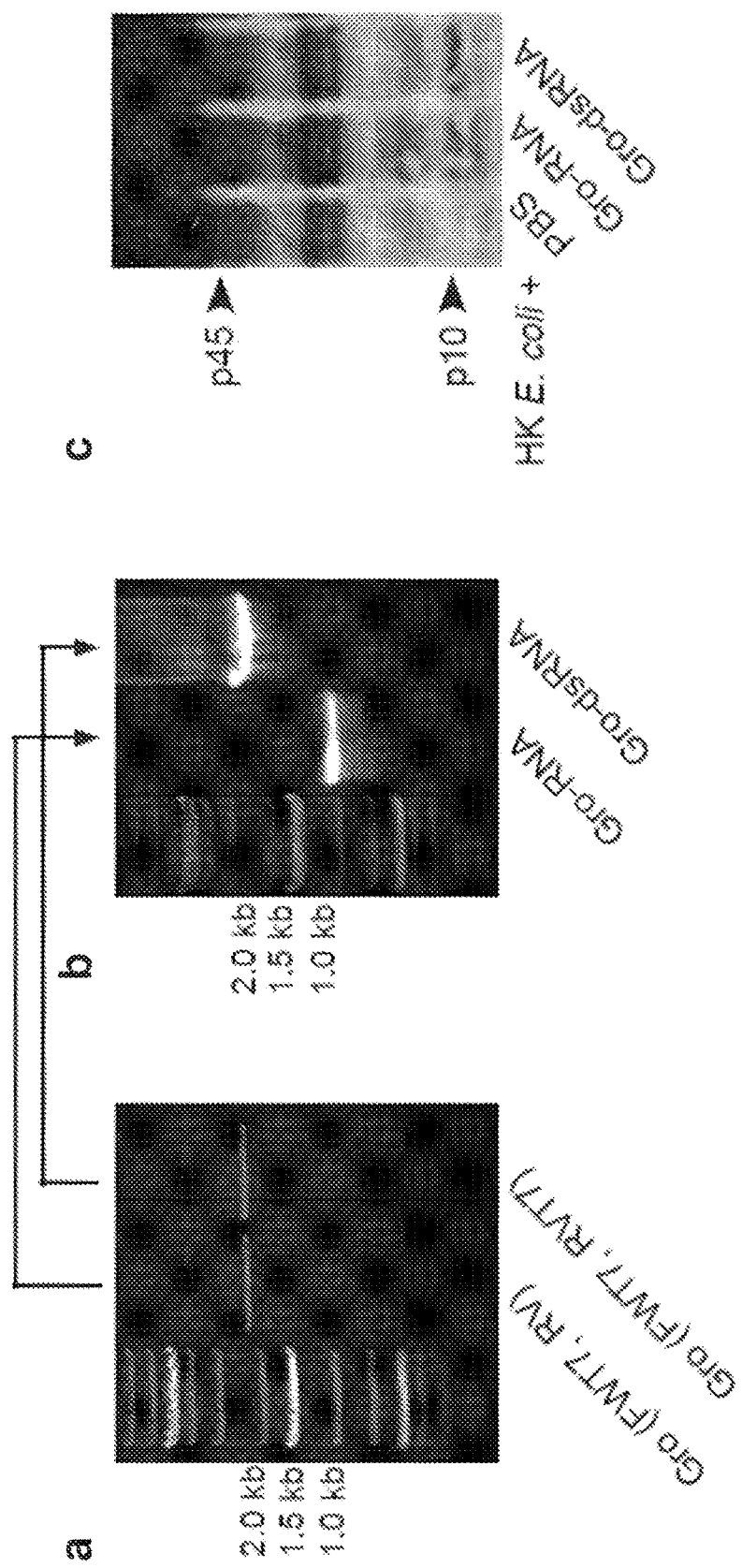
FIG. 25. In vitro transcribed E. coli Gro-mRNA activates the inflammasome only in combination with heat killed E. coli and independently of aberrant transcripts. (a) 1% Agarose gel electrophoresis of PCR amplified full-length E. coli Gro-operon, using genomic E. coli DNA as template, shows a product of 2.1 kb. A T7-promotor sequence was introduced in either the sense strand (Gro FWT7, RV) or both the sense and the anti-sense strand (FWT7, RVT7). (b) In vitro transcription of the PCR product Gro (FWT7, RV) using T7 polymerase yielded Gro-RNA that migrates at 0.95 kb, indicating extensive secondary structures resulting in shorter RNA fragments due to base pairing. In vitro transcription of Gro (FWT7, RVT7) yields two complementary strands that hybridize, thus do not allow formation of extensive secondary structures and therefore migrate at the predicted size of 2.1 kb. (c) BMM were incubated with heat killed (HK) ThyA$^-$ E. coli and the indicated stimuli for 24 hours. Cell lysates were immunoblotted and probed for caspase-1 p10. (d) BMM were incubated with increasing concentrations of Gro-RNA or Gro-dsRNA alone or in combination with HK ThyA$^-$ E. coli for 24 hours, and pyroptosis and IL-1β production (FIG. 4i) were measured. (e) In order to rule out the possibility that aberrant transcripts with 3' extensions, frequently observed with T7 polymerase (Cazenave and Uhlenbeck, Proc Natl Acad Sci USA 91:6972-6976 (1994)), were responsible for the activity of in vitro transcribed Gro-RNA, we excised and purified Gro-RNA from agarose gels and added it to BMM (at 10 μg/ml) in combination with HK E. coli, and measured IL-1β and IL-6 production after 24 hours by ELISA. We compared the activity of gel-extracted Gro-RNA (gel extr.) to regular Gro-RNA and to purified total E. coli RNA. #; 'not detected'.
Figure 25:
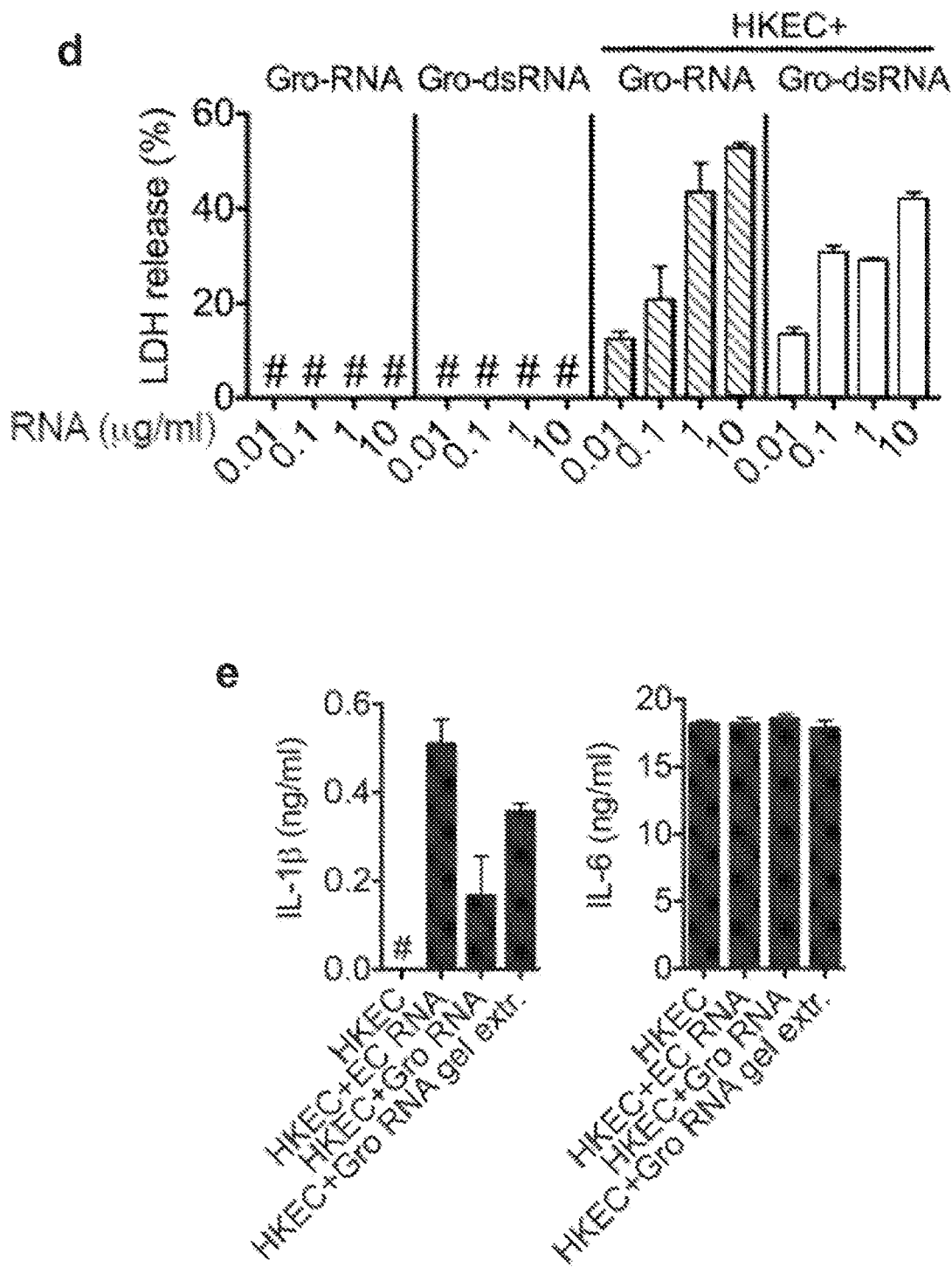

In vitro transcribed single-stranded mRNA of the E. coli Gro-operon (FIGS. 25a and 25b), which is strongly expressed upon phagocytosis of bacteria (Buchmeier et al., Science 248: 730-732 (1990)), induced caspase-1 cleavage and subsequent pyroptosis and IL-1β production when phagocytosed together with HK ECThyA⁻ (FIGS. 4c and 4e; FIG. 6; FIGS. 25c-e). The single-stranded Gro-mRNA sequence had a predicted secondary structure with regions of high probability for base pairing (FIG. 4d), consistent with susceptibility of the stimulatory activity to RNase III treatment (FIG. 4a). Indeed, fully dsGro-mRNA (FIG. 25b) induced similar responses as single-stranded Gro-mRNA of the appropriate length (FIG. 4e; FIG. 25d). Other transcripts also induced such responses, showing that the immunostimulatory property is independent of RNA sequence (FIG. 4f).

Figure 26:
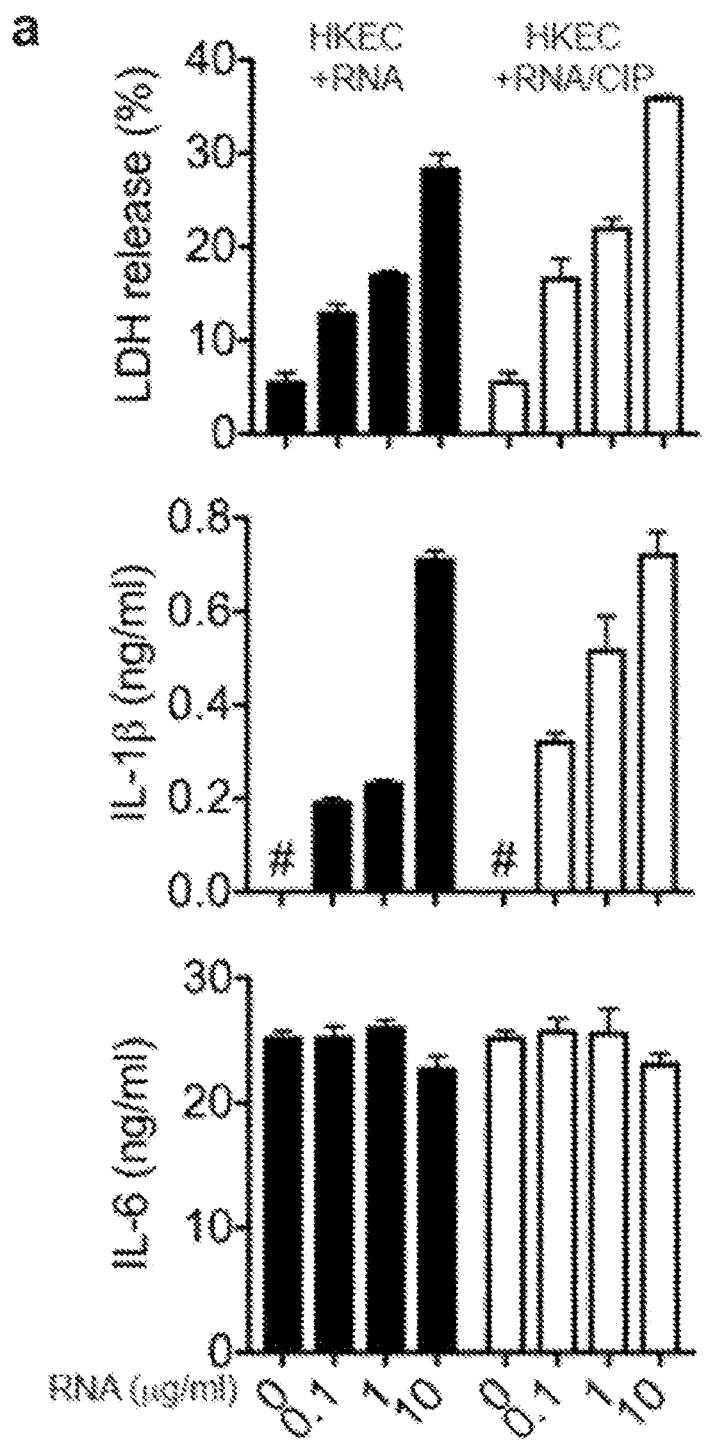
FIG. 26. Dephosphorylation of total E. coli RNA or purified E. coli mRNA does not affect inflammasome activation. (a) Total RNA was isolated from viable ThyA E. coli and BMM were stimulated with heat killed (HK) ThyA$^-$ E. coli in combination with E. coli RNA (HKEC+RNA) or dephosphorylated (CIP treated) E. coli RNA (HKEC+RNA/CIP) at the indicated concentrations. (b) BMM were stimulated with HK ThyA$^-$ E. coli (HKEC), HK ThyA$^-$ E. coli and 0.1 μg/ml of purified E. coli mRNA (HKEC+mRNA), HK ThyA$^-$ E. coli and 0.1 μg/ml of purified E. coli mRNA pre-treated with RNase III (HKEC+mRNA/RNaseIII), or HK ThyA⁻ E. coli and 0.1 μg/ml of dephosphorylated E. coli mRNA (HKEC+mRNA/CIP). After 24 hours, pyroptosis (LDH), IL-10 and IL-6 release were measured. #; 'not detected'. (c, d) Mouse embryonic fibroblasts derived from RIG-I$^{-/l}$ or RIG-I$^{-/-}$ mice were transfected with in vitro transcribed Gro-RNA at 0.1 g/ml (c) or 1 μg/ml (d). IFN-β gene expression 2 hours after transfection was measured by quantitative real time RT-PCR.
Figure 26:
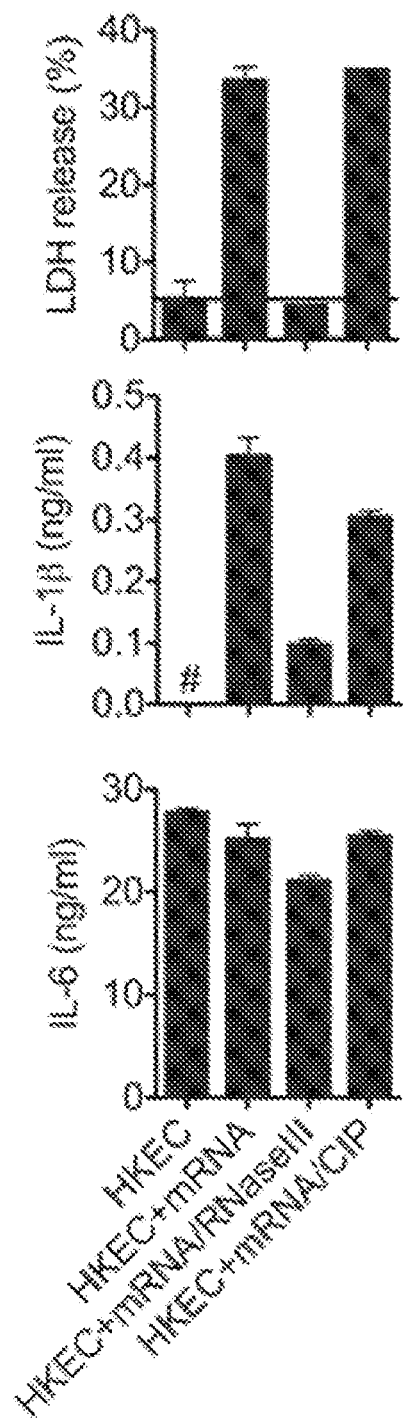
Figure 26:
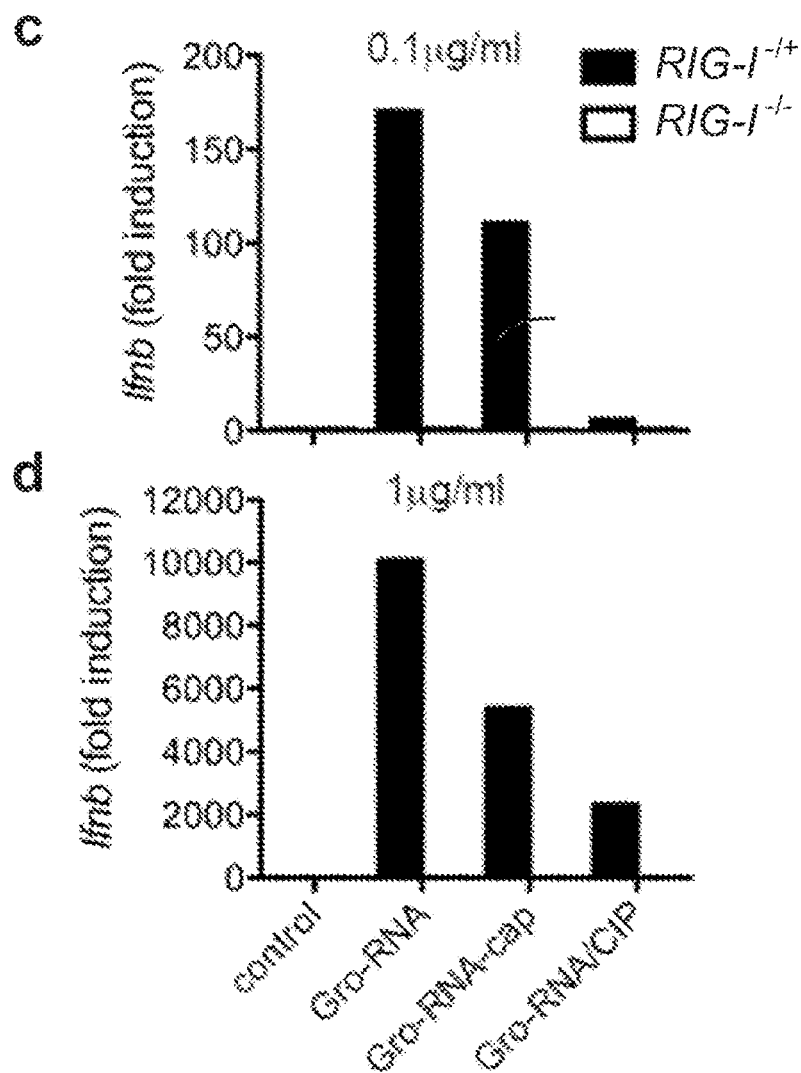
Figure 27:
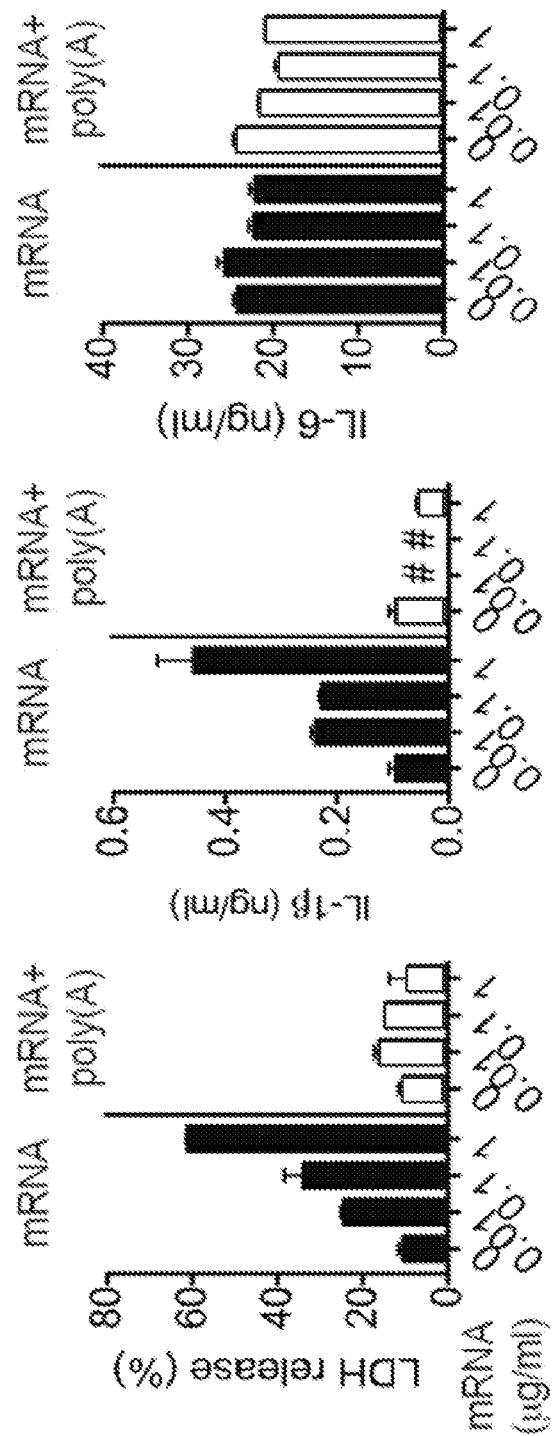
FIG. 27. Polyadenylation of E. coli mRNA impairs inflammasome activation. mRNA was isolated from total E. coli RNA and 3' polyadenylated using E. coli poly(A) polymerase (EPAP) (mRNA+poly(A)) or left untreated (mRNA). BMM were then stimulated with heat killed (HK) ThyA⁻ E. coli alone or in combination with the indicated concentrations of untreated or polyadenylated E. coli mRNA. After 24 hours, pyroptosis (LDH release), IL-1β and IL-6 production were measured. #: "not detected."

Eukaryotic RNA was unable to elicit the responses induced by E. coli mRNA (FIG. 4b; FIG. 6). Unlike eukaryotic mRNA, tri-phosphate moieties at the 5'end of bacterial mRNAs are not capped with 7-methyl-guanosine (7 m$^7$G) (Belasco, Nat Rev Mol Cell Biol 11: 467-478 (2010)), and might betray the prokaryotic origin of these transcripts (Rehwinkel et al., Science 327: 284-286 (2010)). However, neither treatment with calf intestinal phosphatase (CIP) nor capping affected the activity of Gro-mRNA during phagocytosis of HK ECThyA⁻ (FIG. 4g). The stimulatory activity of purified E. coli total RNA or mRNA was also unaltered by CIP treatment (FIGS. 26a and 26b), arguing against a role for the RNA helicase retinoic acid inducible gene-I (RIG-I), which can induce interferon and IL-1β production, but requires 5'-triphosphates for activation (FIG. 26c) (Rehwinkel et al., Science 327: 284-286 (2010)), as well as the interferon inducible protein kinase PKR, which can be activated by 5'-triphosphate bearing RNAs of viral or bacterial origin (Nallagatla et al., RNA Biol 5: 140-144 (2008)). Moreover, TRIF and NLRP3 are dispensable for RIG-I function, but required for the stimulatory activity of bacterial RNA (FIGS. 2a, 2b, and 3d). Interestingly, RNA can induce RIG-I-dependent IFN-β during infection with an invasive intracellular bacterium (Monroe, K. M., McWhirter, S. M. & Vance, R. E. PLoS Pathog 5, e1000665 (2009)), suggesting that the nature of microbial pathogenesis and cellular context in which bacterial RNA is recognized may determine the choice of innate sensors engaged. In contrast to 5'-triphosphate removal, adding polyadenylyl groups to the 3'end of Gro-mRNA or purified E. coli mRNA abrogated IL-1β secretion and pyroptosis (FIG. 4g; FIG. 27). Similar results were obtained when we used primary human monocytes isolated from peripheral blood. Human monocytes produced IL-1β only after stimulation with live ECThyA⁻, but not with HK ECThyA⁻ (unpublished data, not shown). In addition to E. coli, we also examined the responses to live and HK Acinetobacter baumanii, a pathogenic bacterium with low virulence in immunocompetent individuals, but high multi-drug resistance rates. Similar to ECThyA⁻, only live but not HK Acinetobacter baumanii induced IL-103 release from human monocytes, whereas no differences were observed for IL-6 production (unpublished data, not shown). Stimulation of human peripheral blood mononuclear cells (PBMC), containing monocytes and lymphocytes, with live ECThyA⁻ induced the production of IgG and IgA, which was not observed upon stimulation with HK ECThyA⁻ (unpublished data, not shown). These results demonstrate the cross-species relevance of our findings and have direct implications for the use of vita-PAMPs such as bacterial RNA as potent new vaccine adjuvants in humans. It also follows that the absence of 3'-polyadenylation (Belasco, Nat Rev Mol Cell Biol 11: 467-478 (2010)) may allow specific detection of prokaryotic mRNA during infection. Additional features may distinguish self from microbial RNAs such as internal naturally occurring nucleoside modifications in eukaryotic RNA (Nallagatla, supra; Kariko et al., Immunity 23: 165-175 (2005)).

To test the impact of vita-PAMPs on adaptive immunity, we immunized mice with either viable or dead ECThyA⁻, or a combination of dead ECThyA⁻ and purified total bacterial RNA (FIG. 28). While all three vaccines induced similar polyclonal anti-E. coli IgM responses, production of class-switched IgG subclasses was strongly enhanced in response to vaccination with viable compared to killed E. coli (FIG. 4h). Adding total bacterial RNA to killed ECThyA⁻ elevated IgG1, IgG2c, IgG2b and IgG3 antibody titers to or above the levels in mice immunized with viable ECThyA⁻. Thus, innate detection of bacterial viability leads to robust activation of a humoral adaptive response. These findings indicate that bacterial RNA can augment killed vaccines to perform as well as live ones.

Figure 29:
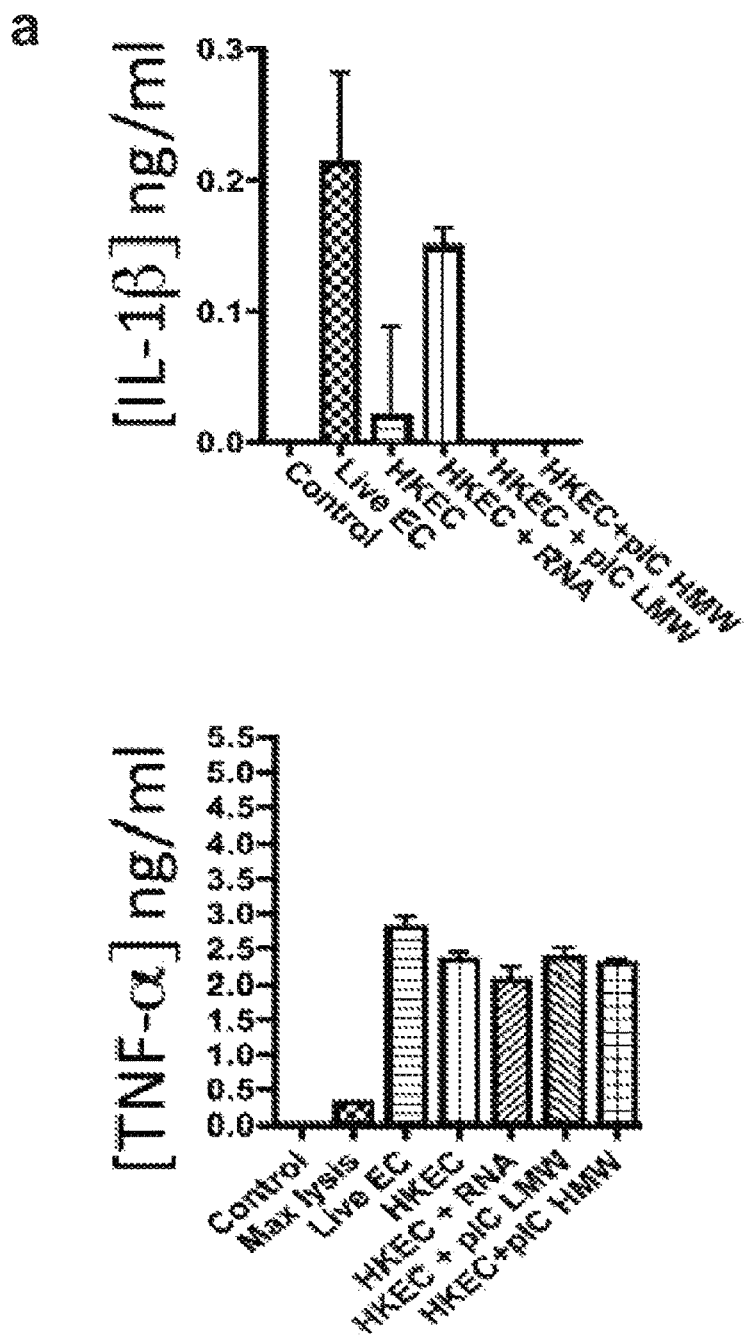
FIG. 29. Poly (I:C) RNA does not restore the immune responses associated with bacterial viability. BMDC were treated with viable E. coli, or HKEC, HKEC with 10 g/ml of total bacterial RNA, HKEC with 3 μg/ml low molecular weight (LMW) poly(I:C), HKEC with 3 μg/ml high molecular weight (HMW) poly(I:C), or HKEC with both LMW and HMW poly(T:C). IL-1β and TNF-α levels were measured by ELISA at 24 hours by ELISA, and are reported in ng/ml (a and b). LDH release from BMDC was measured at 24 hours by ELISA as a percent of maximal release as determined by total cell lysis (b). TNF-α ELISA optical density (O.D.) values measured by a spectrophotometer at 495 nm wavelength are also shown (b).
Figure 29:
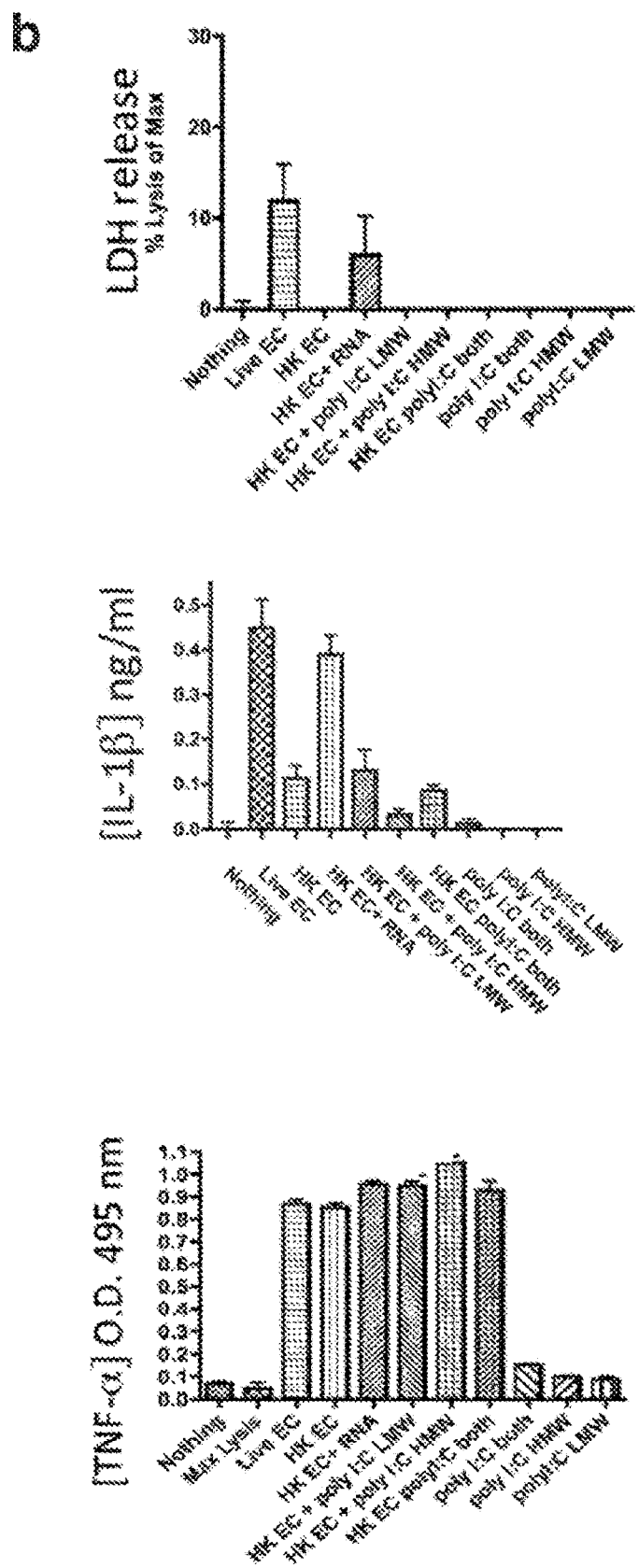

To test whether synthetic RNA can be used to mimic the effects of prokaryotic RNA on the immune response, we treated BMDC with Poly (I:C), the synthetic analog of double-stranded RNA. We found that unlike bacterial RNA, neither the low molecular weight (LMW) poly(I:C) nor the high molecular weight (HMW) poly(I:C) was capable of inducing IL-1β (FIG. 29a and FIG. 29b) or lactate dehydrogenase (LDH) release (FIG. 29b) from BMDC when combined with heat-killed E. coli. TNF-α production, which can be induced by both live and dead E. coli, was not affected by the addition of LMW and HMW forms of Poly(I:C) (FIGS. 29a and b). The LMW and HMW forms alone induced neither IL-1β nor TNF-α production (FIGS. 29a and b). These results demonstrate that poly(I:C) may not fully recapitulate the responses induced by bacterial RNAs, and that features unique to bacterial RNAs that are not reproduced in the synthetic poly(I:C) molecule are particularly efficient at inducing theses responses. Therefore, new synthetic RNAs that incorporate the key features describe herein (e.g., a 3' stem loop structure) would be superior to poly(I:C) in serving as an adjuvant that replicates the protective immunity elicited by live vaccines.

Our findings reveal an inherent ability of the immune system to distinguish viable from dead microorganisms. The presence of live bacteria in sterile tissues, regardless of whether these (still) express virulence factors, poses an acute threat that must be dealt with by an aggressive immune response. Dead bacteria, on the other hand, would signify a successful immune response that can now subside. Detection of vita-PAMPs within sterile tissues signifies microbial viability. Other vita-PAMPs may exist in the form of second messengers like cyclic di-adenosine or di-guanosine monophosphates (Vance, et al., Cell Host Microbe 6: 10-21 (2009); Woodward et al., Science 328: 1703-1705 (2010)) or quorum-sensing molecules (Vance et al., Cell Host Microbe 6: 10-21 (2009)). Given that bacteria tightly regulate their virulence via multiple mechanisms in response to different environmental signals and inside a host organism during infection (Gripenland et al., Nat Rev Microbiol 8: 857-866 (2010); Raskin et al., Cell 124: 703-714 (2006)), detection of invariant vita-PAMPs essential to bacterial survival may be a non-redundant fail-safe strategy for host protection.

What is claimed is:

1. A vaccine composition comprising a tumor antigen and an adjuvant, wherein said adjuvant comprises prokaryotic mRNA, wherein the prokaryotic mRNA has structural features comprising a 3' stem loop structure, intramolecular base-pairing, and no 3' poly(A) tail.

2. The composition of claim 1, wherein the tumor antigen is carried by a cell.

3. The composition of claim 2, wherein the prokaryotic mRNA is contained in the cell.

4. A vaccine composition comprising an immunogenic peptide of microbial or mammalian origin and an adjuvant, wherein said adjuvant comprises prokaryotic mRNA, wherein the prokaryotic mRNA has structural features comprising a 3' stem loop structure, intramolecular base-pairing, and no 3' poly(A) tail.

5. The composition of claim 4, wherein the immunogenic peptide is carried by a cell.

6. The composition of claim 5, wherein the prokaryotic mRNA is contained in the cell.

7. The composition of claim 1, wherein the mRNA has no 5' tri-phosphate group.

8. The composition of claim 1, wherein the mRNA contains nucleotide modifications.

9. A method of eliciting an immune response in a subject, comprising administering to the subject the composition of claim 1.

10. The method of claim 9, wherein the subject is human.

11. The method of claim 9, wherein the immune response protects the subject from developing a cancer, or treats a subject in need of cancer immunotherapy.

12. The method of claim 9, wherein the immune response comprises one or more of the following: IL-1β production, IFN-β production, increased IgG isotype levels, increased primary and secondary T cell responses, and death of infected cells.

13. A method of inducing IFN-β or IL-1β production in immune cells, comprising contacting the cells with the composition of claim 1.

14. A method of preparing a vaccine composition of claim 1, comprising mixing a tumor antigen with prokaryotic mRNA.

15. An immunization kit, comprising a vaccine composition comprising a tumor antigen, and an adjuvant composition comprising prokaryotic mRNA, wherein the prokaryotic mRNA has structural features comprising a 3' stem loop structure, intramolecular base-pairing, and no 3' poly(A) tail.

16. The composition of claim 1, wherein the vaccine further comprises a second adjuvant.

17. The composition of claim 16, wherein the second adjuvant is lipopolysaccharide.

18. The composition of claim 16, wherein the second adjuvant is monophosphoryl lipid A.

* * * * *

SEQUENCE LISTING

<160> NUMBER OF SEQ ID NOS: 21

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gaagtccctc accctcccaa                                                   20

<210> SEQ ID NO 2
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ggcatggacg cgacca                                                       16

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
aaagacggca cacccaccct gc                                                22

<210> SEQ ID NO 4
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
tgtcctgacc actgttgttt cccag                                             25

<210> SEQ ID NO 5
<211> LENGTH: 14
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gcactgggtg gaat                                                         14

<210> SEQ ID NO 6
<211> LENGTH: 14
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ttctgaggca tcaa                                                         14

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
cgagacctct gggaaaaagc t                                              21

<210> SEQ ID NO 8
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gcataccata gaggaatgtg atgtaca                                        27

<210> SEQ ID NO 9
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
taatacgact cactataggg caccagccgg gaaaccacg                           39

<210> SEQ ID NO 10
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
taatacgact cactatagga aaagaaaaac ccccagacat                          40

<210> SEQ ID NO 11
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
agatgaccaa aagaaaaacc cccagacatt                                     30

<210> SEQ ID NO 12
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
taatacgact cactataggg catatgagca tcgataaaag ttac                     44

```
<210> SEQ ID NO 13
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
tttaaagatc gtcaacgtaa ccgag                                          25

<210> SEQ ID NO 14
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
taatacgact cactataggg atgtctgaac cacgtttcgt                           40

<210> SEQ ID NO 15
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
agtcaaactc cagttccacc tgctccgaa                                      29

<210> SEQ ID NO 16
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Trp Glu His Asp
1

<210> SEQ ID NO 17
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Ile Glu Asp Thr
1

<210> SEQ ID NO 18
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Tyr Val Ala Asp
```

```
<210> SEQ ID NO 19
<211> LENGTH: 44
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 19
agaaauaaac aaaccccgg gcagaaaugu cuggggguuu uucu                        44

<210> SEQ ID NO 20
<211> LENGTH: 44
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 20
acgaucuccg uggccucauu gguucggagc agguggaacu ggag                       44

<210> SEQ ID NO 21
<211> LENGTH: 40
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 21
gccaacguuc ggacguccga cgauggcaau aaauccgcag                            40
```